(12) United States Patent
Metallinos

(10) Patent No.: US 7,982,064 B2
(45) Date of Patent: Jul. 19, 2011

(54) METHOD FOR PREPARING ORTHO-SUBSTITUTED AMINOFERROCENES

(75) Inventor: Costa Metallinos, St. Catharines (CA)

(73) Assignee: Brock University, St. Catharines, Ontario (CA)

(*) Notice: Subject to any disclaimer, the term of this patent is extended or adjusted under 35 U.S.C. 154(b) by 0 days.

(21) Appl. No.: 12/624,916

(22) Filed: Nov. 24, 2009

(65) Prior Publication Data

US 2010/0137588 A1 Jun. 3, 2010

Related U.S. Application Data

(60) Provisional application No. 61/117,400, filed on Nov. 24, 2008.

(51) Int. Cl.
*C07F 15/00* (2006.01)

(52) U.S. Cl. ............... 556/145; 556/7; 556/11; 556/20; 556/28; 548/402

(58) Field of Classification Search ........ 556/7, 11, 556/20, 28, 145; 548/402; 544/175
See application file for complete search history.

(56) References Cited

FOREIGN PATENT DOCUMENTS
| | | |
|---|---|---|
| CA | 2656444 | 5/2010 |
| CA | 2686357 | 8/2010 |
| WO | WO/2007/020221 | 2/2007 |

OTHER PUBLICATIONS

Metallinos et al., Organic Letters, vol. 10, No. 16, pp. 3527-3530 (published on the Web Jul. 17, 2008).*
Lai et al., "Intra- and Intermolecular Hydroamination of Alkynes Catalyzed by ortho-Metalated Iridium Complexes", Organometallics, 2007, pp. 1062-1068, vol. 26(4), American Chemical Society.
Metallinos et al., "Palladium(II), Platinum(II), and Iridium(I) Complexes of 2-Phosphino-1-dimethylaminoferrocenes: A Survey of Structure and Catalysis", Organometallics, 2009, pp. 4534-4543, vol. (28 (15), American Chemical Society.
Metallinos et al., "Aminoferrocene Lithiation by Boron Trifluoride Activation", Organic Letters, 2008, pp. 3527-3530, vol. 10(16), American Chemical Society.
2009 CSC Abstract, "Synthesis of 2-Substituted P,N Ligands from Dimethylaminoferrocene: A Survey of Coordination Chemistry, Structure and Catalysis", 2009.
STN Registry TM Search Results. Nov. 23, 2009.
Togni, A. Angew. Chem., Int. Ed. 1996, 35, 1475.
Richards, C. J.; Locke, A. J. Tetrahedron: Asymmetry 1998, 9, 2377.
Arraya's, R. G.; Adrio, J.; Carretero, J. C. Angew. Chem.,Int. Ed. 2006, 45, 7674.
Dai, L.-X.; Tu, T.; You, S.-L.; Deng, W.-P.; Hou, X.-L. Acc. Chem. Res. 2003, 36, 659.
Colacot, T. J. Chem. ReV. 2003, 103, 3101.
Miyake, Y.; Nishibayashi, Y.; Uemura, S. Synlett 2008, n/a, 1747.
Kundig, E. P.; Garcia, A. E.; Lomberget, T.; Bernardinelli, G. Angew. Chem., Int. Ed. 2006, 45, 98.
Marquarding, D.; Klusacek, H.; Gokel, G.; Hoffmann, P.; Ugi, I. J. Am. Chem. Soc. 1970, 92, 5389.

(Continued)

*Primary Examiner* — Porfirio Nazario Gonzalez
(74) *Attorney, Agent, or Firm* — Bereskin & Parr LLP/S.E.N.C.R.L., s.r.l; Patricia Folkins

(57) ABSTRACT

The present disclosure relates to a method for preparing an ortho-substituted aminoferrocene comprising reacting an aminoferrocene with a Lewis acid and a lithiating reagent in the presence of an electrophile to form the ortho-substituted aminoferrocene.

33 Claims, 3 Drawing Sheets

OTHER PUBLICATIONS

Richards, C. J.; Damalidis, T.; Hibbs, D. E.; Hursthouse, M. B. Synlett 1995, n/a, 74.
Uemura, S.; Nishibayashi, Y. Synlett 1995, n/a, 79.
Sammakia, T.; Lathman, H. A.; Schad, D. R. J. Org. Chem. 1995, 60, 10.
Riant, O.; Samuel, O.; Kagan, H. B. J. Am. Chem. Soc. 1993, 115, 5835.
Enders, D.; Peters, R.; Lochtman, R.; Runsink, J. Synlett 1997, n/a, 1462.
Tsukazaki, M.; Tinkl, M.; Roglans, A.; Chapell, B. J.; Taylor, N. J.; Snieckus, V. J. Am. Chem. Soc. 1996, 118, 685.
Taherpour, A. A.; Mansuri, H. R. Turk. J. Chem. 2005, 29, 317.
Rebiere, F.; Riant, O.; Ricard, L; Kagan, H. B. Angew. Chem., Int. Ed. 1993, 32, 568.
Riant, O.; Argouarch, G.; Guillaneux, D.; Samuel, O.; Kagan, H. B. J. Org. Chem. 1998, 63, 3511.
Bolm, C.; Kesselgruber, M.; Muñiz, K.; Raabe, G. Organometallics 2000, 19, 1648.
He'rault, D.; Aelvoet, K.; Blatch, A. J.; Al-Majid, A.; Smethurst, C. A.; Whiting, A. J. Org. Chem. 2007, 72, 71.
Priego, J.; Mancheno, O. G.; Cabrera, S.; Carretero, J. C. J. Org. Chem. 2002, 67, 1346. For a related process starting from a ferrocenyl oxazoline, see: Salter, R.; Pickett, T. E.; Richards, C. J. Tetrahedron:Asymmetry 1998, 9, 4239.
Bertogg, A.; Camponovo, F.; Togni, A. Eur. J. Inorg. Chem. 2005, n/a, 347.
Bertogg, A.; Togni, A. Organometallics 2006, 25, 622.
Buszek, K. R.; Brown, N. J. Org. Chem. 2007, 72, 3125.
Samec, J. S. M.; Backvall, J. E. Chem. Eur. J. 2002, 8, 2955.
Britton, W. E.; Kashyap, R.; El-Hashash, M.; El-Kady, M.; Herberhold, M. Organometallics 1986, 5, 1029.
Sato, M.; Ebine, S. Synthesis 1981, n/a, 472.
Pearson, M. S.; Jensky, B. J.; Greer, F. X.; Hagstrom, J. P.; Wells, N. M.; J. Org. Chem. 1978, 43, 4617.
Fanta, P. E. Synthesis 1974, n/a, 9.
Storer, R. I.; Carrera, D. E.; Ni, Y.; MacMillan, D. W. C. J. Am. Chem. Soc. 2006, 128, 84.
Nishibayashi, Y.; Arikawa, Y.; Ohe, K.; Uemura, S. J. Org. Chem. 1996, 61, 1172.
Stead, D.; O'Brien, P.; Sanderson, A. Org. Lett. 2008, 10, 1409.
Cabello, N.; Kizirian, J.-C.; Gille, S.; Alexakis, A.; Bernardinelli, G.; Pinchard, L.; Caille, J.-C. Eur. J. Org. Chem. 2005, n/a, 483.
Fox, D. J.; Pedersen, D. S.; Warren, S. Org. Biomol. Chem. 2006, 4, 3102.
Mealey, M. J.; Luderer, M. R.; Bailey, W. F.; Sommer, M. B. J. Org. Chem. 2004, 69, 6042.
O'Brien, P. Chem. Commun. 2008, 655.
Black, P.J.; Edwards, M.G.; Williams, J. M. J. Eur. J. Org. Chem. 2006, 19, 4367.
Metallinos, C. et al., "Asymmetric Lithiation of Boron Trifluoride-Activated Amino-ferrocenes: An Experimental and Computational Investigation" Adv Synth Catal. 2010, 352, 1967-1982.
Metallinos, C et al., "Asymmetric hydrogenation of alkene with planar chiral 2-phosphino-1-aminoferrocene-iridium(I) complexes", Journal of Organometallic Chemistry 696 (2011) 141-149.
He, J.; Zheng, J.; Liu, J.; She, X.; Pan, X. Org. Lett. 2006, 8, 4637.
Hareau, G. P. J.; Koiwa, M.; Hikichi, S.; Sato, F. J. Am. Chem. Soc. 1999, 121, 3640.

* cited by examiner

METHOD FOR PREPARING ORTHO-SUBSTITUTED AMINOFERROCENES

FIELD OF THE DISCLOSURE

The present disclosure relates to a method for preparing ortho-substituted aminoferrocenes comprising reacting a lithiated aminoferrocene in the presence of an electrophile to form the ortho-substituted aminoferrocene.

BACKGROUND OF THE DISCLOSURE

The lithiation of monosubstituted ferrocenes bearing chiral or achiral directing groups[1,2] is a key method for the preparation of planar chiral reagents with applications in catalysis[3] and materials science.[4] Carbon-based directing groups that have been developed for this purpose include (dialkylaminomethyl)ferrocenes[5] (e.g., 1), oxazolines[6] (2), acetals[7] (3), hydrazones[5] (4), and carboxamides[9] (5), which impart planar chirality by diastereoselective or enantioselective deprotonation (Scheme 1).[1,2,10] The most commonly employed heteroatom-based directing groups are chiral sulfoxides 6 (R=p-Tol, t-Bu)[11] and related sulfoximines,[12] derivatives of which have been applied in asymmetric synthesis.[3a] More recently, nonstereoselective lithiation of ferrocenyl benzimidazoles (7) has also been reported.[13]

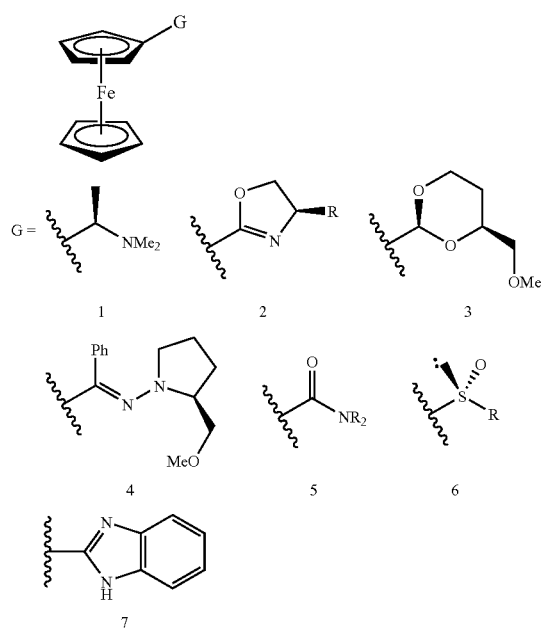

A rekindling of interest in aminoferrocenes in recent years has resulted in planar chiral ligands such as aminosulfoxide 8 (Scheme 2), which is prepared by "E+" electrophile quench of the 2-lithio derivative of sulfoxide 6.[14] In contrast, ferrocenyl N-heterocyclic carbenes[15] (9) and aminophosphines[16] (10) have been prepared by more circuitous routes involving Curtius rearrangement of ferrocene-2-carboxylic acids derived from 3 and 1.

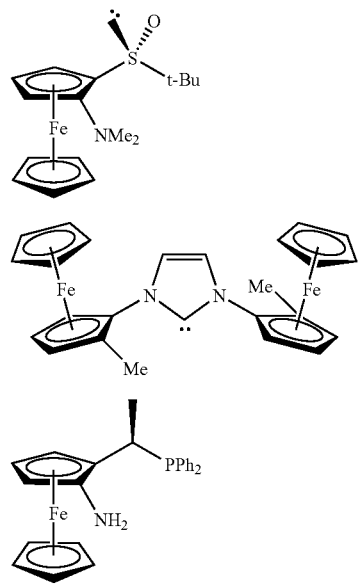

SUMMARY OF THE DISCLOSURE

It has now been determined that the lithiation of aminoferrocenes in the presence of a Lewis acid is directed to the ortho-position of the aminoferrocene. Subsequent reaction of the lithiated aminoferrocene with an electrophile results in an ortho-substituted aminoferrocene.

Accordingly, the present disclosure provides a method for preparing an ortho-substituted aminoferrocene comprising:
(i) reacting an aminoferrocene with a suitable Lewis acid and a lithiating reagent in the presence of an electrophile under suitable conditions to produce the ortho-substituted aminoferrocene; or
(ii) reacting an aminoferrocene with a suitable Lewis acid and a lithiating reagent under suitable conditions to produce a lithiated aminoferrocene and subsequently reacting the lithiated aminoferrocene with an electrophile under suitable conditions to produce the ortho-substituted aminoferrocene.

In an embodiment of the disclosure, the aminoferrocene is a compound of the formula (I):

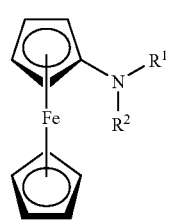

(I)

wherein,
$R^1$ and $R^2$ are simultaneously or independently selected from $C_{1-10}$alkyl and $C_{3-10}$cycloalkenyl, the latter 2 groups being optionally substituted, or $R^1$ and $R^2$ are linked together to form an optionally substituted monocyclic or bicyclic, saturated ring having 4 or more atoms, including the nitrogen atom to which said groups are bonded;

the cyclopentadienyl ring of the ferrocene that does not contain the amino group is optionally substituted; and the optional substituents are selected from one or more of fluoro, chloro, $C_{1-6}$alkyl and fluorosubstituted $C_{1-6}$alkyl.

In a further embodiment, $R^1$ and $R^2$ are simultaneously or independently $C_{1-6}$alkyl. In another embodiment of the disclosure, $R^1$ and $R^2$ are methyl.

In a further embodiment, $R^1$ and $R^2$ are linked together to form an optionally substituted 5-membered ring, including the nitrogen atom to which $R^1$ and $R^2$ are bonded. In another embodiment, $R^1$ and $R^2$ are linked together along with the nitrogen atom to which they are bonded to form a pyrrolidinyl group.

In a further embodiment, the cyclopentadienyl ring of the ferrocene that does not contain the amino group is unsubstituted In another embodiment of the disclosure, the Lewis acid is selected from $BX_3$ and $AlX_3$, wherein X is halo. In a further embodiment, the Lewis acid is $BF_3$ or $BCl_3$. In another embodiment, the Lewis acid is $BF_3$.

In an embodiment of the disclosure, the lithiating reagent is an alkyl lithiating reagent. In a further embodiment, the alkyl lithiating reagent is n-butyl lithium, s-butyl lithium, cyclopentyl lithium, t-butyl lithium or iso-propyl lithium. In a further embodiment, the alkyl lithiating reagent is n-butyl lithium or iso-propyl lithium.

In another embodiment of the disclosure, the electrophile is a carbon electrophile. In another embodiment, the carbon electrophile is a ketone, an amide or an isocyanate. In another embodiment, the electrophile is a heteroatom electrophile. In another embodiment, the heteroatom electrophile is a silane, a borate, a phosphine, a sulfide, a stannane or a halide.

In an embodiment of the disclosure, when the electrophile is a phosphine, it is a compound of the formula (II):

$$R^3R^4\text{—P-LG} \qquad (II)$$

wherein, $R^3$ and $R^4$ are simultaneously or independently selected from $C_{1-20}$alkyl, $C_{3-20}$cycloalkyl, $C_{6-14}$aryl and heteroaryl, the latter three groups being optionally substituted, or $R^3$ and $R^4$ are linked together to form an optionally substituted monocyclic or polycyclic, saturated, unsaturated and/or aromatic ring system having 4 or more atoms, including the phosphorous atom to which said groups are bonded, and in which one or more carbon atoms in said monocyclic or polycyclic ring system is optionally replaced with a heteromoiety selected from O, N, NH and N—$C_{1-6}$alkyl;

LG is any suitable leaving group; and the optional substituents are selected from one or more of halo, $C_{1-6}$alkyl, fluoro-substituted $C_{1-6}$alkyl, $C_{3-6}$cycloalkyl and $C_{6-14}$aryl.

In an embodiment, $R^3$ and $R^4$ are simultaneously or independently selected from phenyl and $C_{1-6}$alkyl. In another embodiment, $R^3$ and $R^4$ are simultaneously or independently selected from phenyl, methyl, ethyl, n-propyl, iso-propyl, sec-butyl, tert-butyl and n-butyl.

In another embodiment, LG is halo, triflate, mesylate or tosylate. In a further embodiment, LG is chloro.

In another embodiment of the disclosure, the compound of formula (II) is

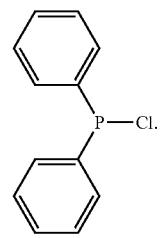

In another embodiment of the disclosure, there is also included ortho-substituted aminoferrocenes having the following formula (A) that are useful as ligands for metal-based catalysts:

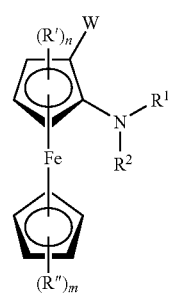

(A)

wherein $R^1$ and $R^2$ are simultaneously or independently selected from $C_{1-10}$alkyl and $C_{3-10}$cycloalkenyl, the latter 2 groups being optionally substituted, or $R^1$ and $R^2$ are linked together to form an optionally substituted monocyclic or bicyclic, saturated ring having 4 or more atoms, including the nitrogen atom to which said groups are bonded;

wherein each R' and R" is independently or simultaneously selected from H, fluoro, chloro, ($C_1$-$C_6$)-alkyl or fluoro-substituted-($C_1$-$C_6$)-alkyl;

n is 1, 2 or 3;

m is 1, 2, 3, 4 or 5;

W is $PR^3R^4$, $P(Y)R^3R^4$, $SiR^5R^6R^7$, $SnR^5R^6R^7$, halo, S—$R^8$, borate esters, $CH_2$heteroaryl, $CH_2OR^9$, $C_{6-10}$aryl, $C_{6-10}$aryl substituted with one to three halo, $C_{1-10}$alkyl, $OR^3$, $PR^3R^4$ and/or $NR^5R^6$, C(O)H, C(OH)$R^5R^6$, $OR^9$, C(O)$NR^9R^{10}$ or $CH_2NR^9R^{10}$;

$R^3$ and $R^4$ are simultaneously or independently selected from $C_{1-20}$alkyl, $C_{3-20}$cycloalkyl, $C_{6-14}$aryl and heteroaryl, the latter three groups being optionally substituted, or $R^3$ and $R^4$ are linked together to form an optionally substituted monocyclic or polycyclic, saturated, unsaturated and/or aromatic ring system having 4 or more atoms, including the phosphorous atom to which said groups are bonded, and in which one or more carbon atoms in said monocyclic or polycyclic ring system is optionally replaced with a heteromoiety selected from O, N, NH and N—$C_{1-6}$alkyl; $R^5$, $R^6$, $R^7$ and $R^8$ are simultaneously or independently selected from $C_{1-10}$alkyl, $C_{2-10}$alkenyl, $C_{3-10}$cycloalkyl and $C_{6-10}$aryl, each being optionally substituted with one to four optional substituents selected from halo, $C_{1-6}$alkyl, fluoro-substituted $C_{1-6}$alkyl, $C_{3-6}$cycloalkyl and phenyl;

$R^5$, $R^6$, $R^7$ and $R^8$ are simultaneously or independently selected from $C_{1-10}$alkyl, $C_{2-10}$alkenyl, $C_{3-10}$cycloalkyl and $C_{6-10}$aryl, each being optionally substituted with one to four substituents independently selected from halo, $C_{1-6}$alkyl, fluoro-substituted $C_{1-6}$alkyl, $C_{3-6}$cycloalkyl and phenyl, $R^9$ and $R^{10}$ are simultaneously or independently selected from H, $C(O)R^8$, $C_{1-10}$alkyl, $C_{2-10}$alkenyl, $C_{3-10}$cycloalkyl and $C_{6-10}$aryl, each being optionally substituted with one to four substituents independently selected from halo, $C_{1-6}$alkyl, fluoro-substituted $C_{1-6}$alkyl, $C_{3-6}$cycloalkyl and phenyl;

Y is S or O; and heteroaryl is a 5- or 6-membered ring containing 1 to 5 heteromoieties selected from S, O, N, NH and N—$C_{1-6}$alkyl, or any stereoisomer and/or enantiomer thereof, with the proviso that $R^9$ and $R^{10}$ are not simulataneously $C_{1-10}$alkyl.

In another embodiment of the disclosure, there is also included di-ortho-substituted aminoferrocenes having the following formula (B):

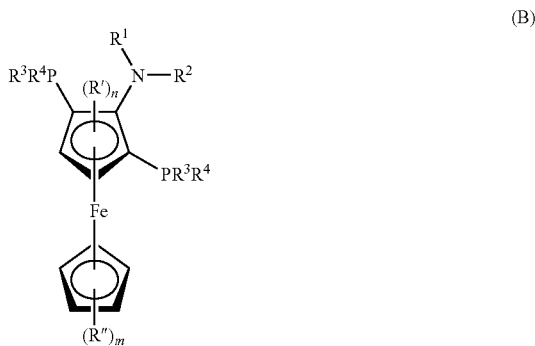

(B)

wherein $R^1$-$R^4$, R' and R" are defined as above, and any stereoisomer and/or enantiomer thereof.

In another embodiment, the ortho-substituted aminoferrocenes of the present disclosure are used as ligands for metal catalysts for synthetic organic reactions. Accordingly, the present disclosure also includes a method of performing a metal-catalyzed synthetic organic reaction comprising contacting suitable starting materials for the synthetic organic reaction with a metal catalyst comprising a ligand of the formula I as defined herein and reacting the starting materials and catalyst under suitable conditions to form the desired product.

In an embodiment, synthetic organic reactions are selected from hydrogenation, transfer hydrogenation, hydroformylation, hydrosilylation, hydroboration, hydroamination, hydrovinylation, hydroarylation, hydration, oxidation, epoxidation, reduction, C—C and C—X bond formation, functional group interconversion, kinetic resolution, dynamic kinetic resolution, cycloaddition, Diels-Alder, retro-Diels-Alder, sigmatropic rearrangement, electrocyclic reactions, ring-opening and/or ring-closing olefin metathesis, carbonylation and aziridination. In another embodiment, the C—C and C—X bond formation reaction is selected from Heck, Suzuki-Miyaura, Negishi, Buchwald-Hartwig Amination, α-Ketone Arylation, N-Aryl Amination, Murahashi, Kumada, Negishi and Stille reactions.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The application will now be described in greater detail with reference to the drawings in which.

Figure 1:
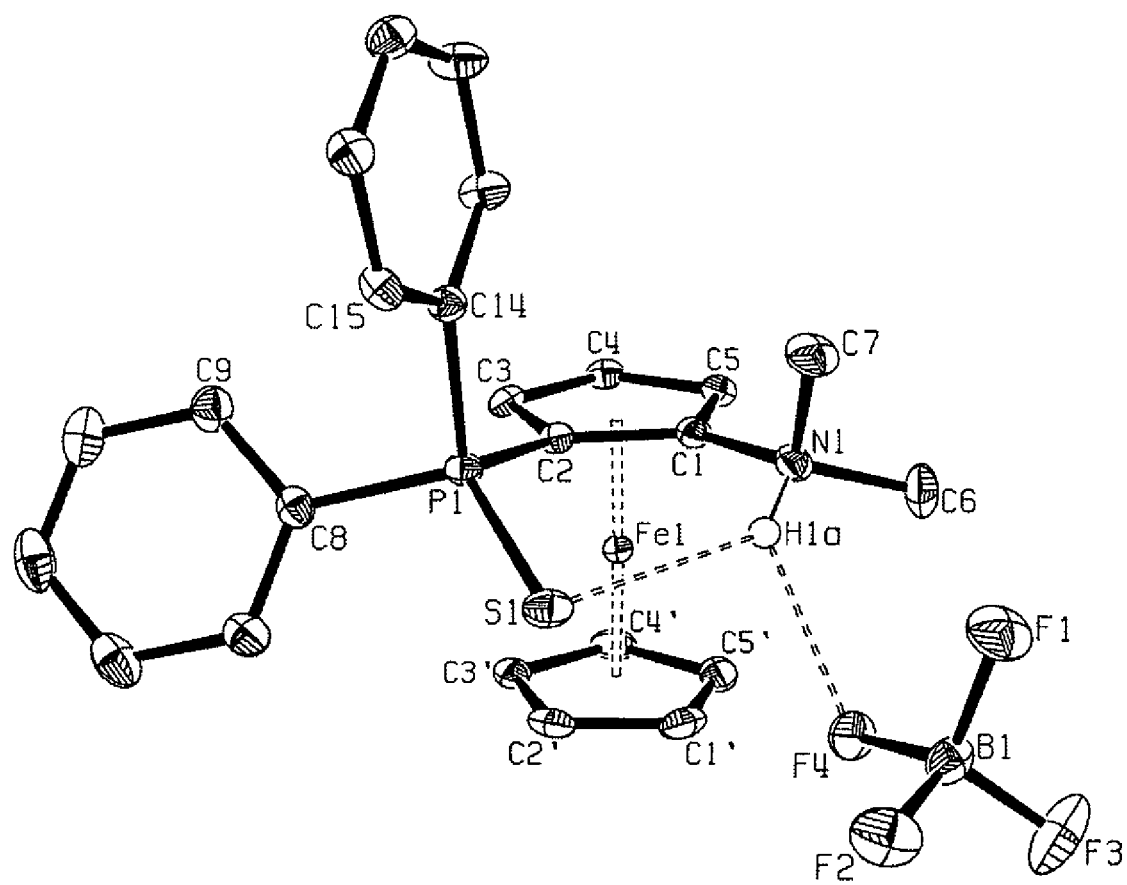
FIG. 1 is an ORTEP plot of (S)-24 with all hydrogen atoms except H1a omitted for clarity.

DETAILED DESCRIPTION OF THE DISCLOSURE (I) Definitions

The term "$C_{1-n}$alkyl" as used herein means straight and/or branched chain, saturated alkyl groups containing from one to "n" carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl group.

The term "$C_{3-n}$cycloalkyl" as used herein means a monocyclic or polycyclic saturated carbocylic group containing from three to n carbon atoms and includes (depending on the identity of n), cyclopropyl, cyclobutyl, cyclopentyl, cyclodecyl, bicyclo[2.2.2]octane, bicyclo[3.1.1]heptane and the like, where the variable n is an integer representing the largest number of carbon atoms in the cycloalkyl group.

The term "$C_{6-n}$aryl" as used herein means a monocyclic or polycyclic carbocyclic ring system containing from 6 to n carbon atoms, at least one aromatic ring and optionally a metal and includes, depending on the identity of n, phenyl, naphthyl, anthracenyl, 1,2-dihydronaphthyl, 1,2,3,4-tetrahydronaphthyl, fluorenyl, indanyl, indenyl, ferrocenyl, and the like, where the variable n is an integer representing the largest number of carbon atoms in the aryl group.

The term "electrophile" as used herein means any compound that can accept a pair of electrons in an electrophilic addition reaction, and include, but not limited to, compounds such as silanes (e.g. trimethylsilyl chloride), ketones (e.g. benzophenone), isocyanates (e.g. phenyl isocyanate), amides (e.g. dimethylformamide), borates (e.g. triethoxyborate), phosphines e.g. chlorodiphenylphosphine), sulfanes (e.g. diphenyldisulfane), stannanes (e.g. chlorotrimethyl tin), halides (e.g. $(ICH_2)_2$) and alkyl halides (e.g. ethyl iodide) and the like.

The term "halo" as used herein means a halogen atom, such as fluorine, chlorine, bromine or iodine.

The term "heteroaryl" unless otherwise specified as used herein means a monocyclic or polycyclic ring system containing one or two aromatic rings and from 5 to 14 heteromoieties of which, unless otherwise specified, one, two, three, four or five are independently selected from O, S, N, NH, $NC_{1-6}$alkyl, N(O), SiH, $SiC_{1-6}$alkyl and $Si(C_{1-6}$alkyl$)_2$ and includes thienyl, furyl, pyrrolyl, pyrididyl, indolyl, quinolyl, isoquinolyl, tetrahydroquinolyl, benzofuryl, benzothienyl and the like.

The term "suitable leaving group" as used herein means any group attached to an electrophilic atom that can be displaced by the lithiated aminoferrocene in an electrophilic addition reaction. Suitable examples of leaving groups include, but are not limited to, halides, including chloro, bromo and iodo, and acetates, tosylates, mesylates and triflates and the like.

The term "lithiating reagent" as used herein means any compound that is able to abstract a hydrogen atom from the ortho-position of the aminoferrocene, and replace the hydrogen atom with a lithium atom. The lithiating reagents as used in the method of the present disclosure include alkyl lithium reagents, such as n-butyl lithium, s-butyl lithium, cyclo-pentyl lithium, t-butyl lithium or iso-propyl lithium.

The term "ortho-substituted" means substitution at a position adjacent to a specified group, for example, ortho-substituted aminoferrocene means a compound that is substituted at the positions adjacent to the amino group of the aminoferrocene.

The term "borate esters" as used herein means a group of the formula —B(OR)$_2$, where each R is the same or different alkyl or aryl group or are combined to form, together with the oxygen and boron atoms, a ring.

The term "ring system" as used herein refers to a carbon-containing ring system, that includes monocycles and polycyclic rings. Where specified, the carbons in the rings may be substituted or replaced with heteroatoms. Ring systems include saturated, unsaturated or aromatic rings, or combinations thereof.

The term "polycyclic" as used herein means groups that contain more than one ring linked together and includes, for example, groups that contain two (bicyclic), three (tricyclic) or four (quadracyclic) rings. The rings may be linked through a single bond, a single atom (spirocyclic) or through two atoms (fused and bridged).

The term "optically pure" as used herein means that the compound exists in one optical isomeric form and comprises less than 5%, suitably less than 1% of alternate optical isomeric forms.

The term "suitable", as in for example, "suitable leaving group", "suitable starting materials" or "suitable conditions" means that the selection of the particular group, compound(s) or conditions would depend on the specific synthetic manipulation to be performed and the identity of the molecule but the selection would be well within the skill of a person trained in the art. All process steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In some cases the chemistries outlined herein may have to be modified, for instance by use of protecting groups, to prevent side reactions of reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 3$^{rd}$ Edition, 1999.

The terms "protective group" or "protecting group" or "PG" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not destroy or decompose the molecule. Many conventional protecting groups are known in the art, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 3$^{rd}$ Edition, 1999.

Unless otherwise indicated, the definitions and embodiments described in this and other sections are intended to be applicable to all embodiments and aspects of the disclosure herein described for which they are suitable as would be understood by a person skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(II) Method of the Disclosure

It has now been determined that that the lithiation of aminoferrocenes in the presence of a Lewis acid is directed to the ortho-position of the aminoferrocene. Subsequent reaction of the lithiated aminoferrocene with an electrophile results in an ortho-substituted aminoferrocene.

Accordingly, the present disclosure provides a method for preparing an ortho-substituted aminoferrocene comprising:
(i) reacting an aminoferrocene with a suitable Lewis acid and a lithiating reagent in the presence of an electrophile under suitable conditions to produce the ortho-substituted aminoferrocene; or
(ii) reacting an aminoferrocene with a suitable Lewis acid and a lithiating reagent under suitable conditions to produce a lithiated aminoferrocene and subsequently reacting the lithiated aminoferrocene with an electrophile under suitable conditions to produce the ortho-substituted aminoferrocene.

In an embodiment of the disclosure, the aminoferrocene is a compound of the formula (I):

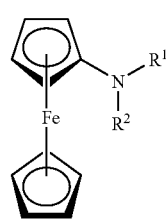

(I)

wherein,
$R^1$ and $R^2$ are simultaneously or independently selected from $C_{1-10}$alkyl and $C_{3-10}$cycloalkenyl, the latter 2 groups being optionally substituted, or $R^1$ and $R^2$ are linked together to form an optionally substituted monocyclic or bicyclic, saturated ring having 4 or more atoms, including the nitrogen atom to which said groups are bonded;
the cyclopentadienyl ring of the ferrocene that does not contain the amino group is optionally substituted; and
the optional substituents are selected from one or more of fluoro, chloro, $C_{1-6}$alkyl and fluorosubstituted $C_{1-6}$alkyl.

In a further embodiment, $R^1$ and $R^2$ are simultaneously or independently $C_{1-6}$alkyl. In another embodiment of the disclosure, $R^1$ and $R^2$ are methyl.

In a further embodiment, $R^1$ and $R^2$ are linked together to form an optionally substituted 5-membered ring, including the nitrogen atom to which $R^1$ and $R^2$ are bonded. In another embodiment, $R^1$ and $R^2$ are linked together along with the nitrogen atom to which they are bonded to form a pyrrolidinyl group.

In a further embodiment, the cyclopentadienyl ring of the ferrocene that does not contain the amino group is unsubstituted It will be understood by those skilled in the art that Lewis acids are electron pair acceptors, and as such, when an aminoferrocene of formula (I) is reacted with a Lewis acid, such as $BF_3$, the lone pair of electrons on the nitrogen atom of the amino group on the aminoferrocene, would act as a Lewis base, and donate the electron pair. Without being limited by theory, when a Lewis acid, such as $BF_3$, is reacted with an aminoferrocene of the formula (I), a zwitterion forms between the Lewis acid ($BF_3$) and Lewis base ($—NR^1R^2$) (Scheme 3).

Scheme 3

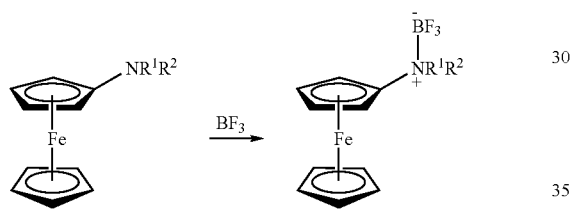

Accordingly, it will be understood by those skilled in the art that the suitable Lewis acid is any Lewis acid that is able to accept electrons from the amino group of the aminoferrocene. In another embodiment, the suitable Lewis acid is any Lewis acid able to form a zwitterion with the aminoferrocene. In another embodiment, the suitable Lewis acid is selected from $BX_3$ and $AlX_3$, wherein X is halo. In a further embodiment, the suitable Lewis acid is $BF_3$ or $BCl_3$. In another embodiment, the Lewis acid is $BF_3$ Again without being bound by theory, the zwitterion as shown in Scheme 3, directs the lithiating reagent to the ortho-position of the aminoferrocene. Accordingly, when the zwitterion shown in Scheme 3 is reacted with a lithiating reagent, the corresponding 2-lithioferrocene is obtained (Scheme 4).

Scheme 4

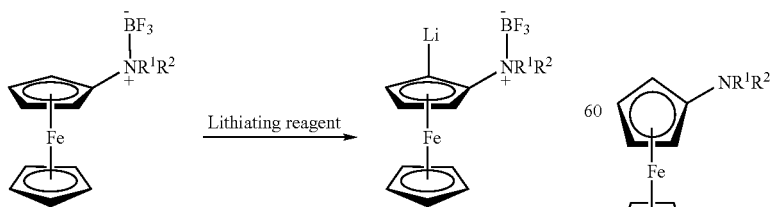

Accordingly, it will be understood by those skilled in the art that the lithiating reagent is any reagent which is able to abstract a hydrogen from the ortho-position of the aminoferrocene and replace the hydrogen atom with lithium. In an embodiment of the disclosure, the lithiating reagent is an alkyl lithiating reagent. In a further embodiment, the alkyl lithiating reagent is n-butyl lithium, s-butyl lithium, cyclopentyl lithium, t-butyl lithium or iso-propyl lithium. In a further embodiment, the alkyl lithiating reagent is n-butyl lithium or iso-propyl lithium.

In another embodiment of the disclosure, the lithiated aminoferrocene as shown in Scheme 4 participates in an electrophilic addition reaction in the presence of an electrophile. It will be understood by those skilled in the art that carbon atom of the carbon-lithium bond will be nucleophilic and will therefore react with electrophiles, resulting in the ortho-substituted aminoferrocenes. In an embodiment, the electrophile is a carbon electrophile, for example, a ketone, an isocyanate or an amide. In another embodiment, the electrophile is a heteroatom electrophile, for example, a silane, a borate, a phosphine, a sulfane, a stannane or a halide. It will be appreciated by a person skilled in the art that a wide variety of electrophiles are capable of participating in a reaction with the lithiated aminoferrocene and such a person would be able to identify and select such suitable electrophilic reagents.

In another embodiment of the disclosure, an ortho-substituted aminoferrocene as obtained from the process of the present disclosure, is subjected again to the process of the disclosure to form a 1,2,3-trisubstituted aminoferrocene. In an embodiment, an ortho-substituted aminoferrocene is reacted with a Lewis acid and a lithiating reagent in the presence of an electrophile, or alternatively, the electrophile is reacted with a pre-formed ortho-lithiated aminoferrocene, to form the 1,2,3-trisubstituted aminoferrocene (Scheme 5).

Scheme 5

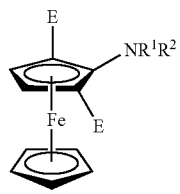

In another embodiment of the disclosure, as seen in Scheme 6, the ortho lithiation of an aminoferrocene and subsequent quenching with an electrophile also results in the lithiation and substitution of the ring that does not contain the amine group. Accordingly, in addition to the ortho-substituted aminoferrocene, a 1,2,1'-trisubstituted aminoferrocene is also obtained.

Scheme 6

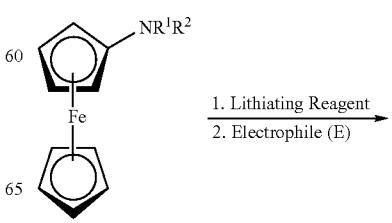

-continued

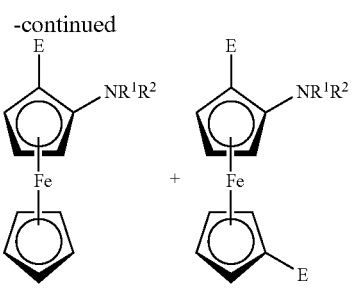

In another embodiment of the disclosure, a chiral ligand is added with the lithiating reagent for an asymmetric lithiation of the aminoferrocene. In an embodiment, the chiral ligand is a chiral diamine. In another embodiment, the chiral ligand is (−)-sparteine, (S,S)—N,N,N',N'-tetramethylcyclohexane-1,2-diamine or

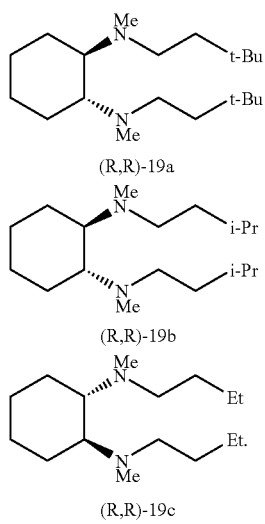

Without being bound by theory, as the lithiation of the aminoferrocene occurs at the ortho-position, the regioselectivity of this reaction implies an organized transition state involving complexation of the lithiating reagent with the zwitterion (Scheme 1) during the abstraction of the hydrogen atom. Accordingly, in an embodiment, the addition of a chiral ligand during the ortho-lithiation of the zwitterion promotes the asymmetric abstraction of the hydrogen atom.

In an embodiment of the disclosure, the electrophile is a phosphine of the formula (II):

$$R^3R^4\text{—P-LG} \qquad (II)$$

$R^3$ and $R^4$ are simultaneously or independently selected from $C_{1-20}$alkyl, $C_{3-20}$cycloalkyl, $C_{6-14}$aryl and heteroaryl, the latter three groups being optionally substituted, or $R^3$ and $R^4$ are linked together to form an optionally substituted monocyclic or polycyclic, saturated, unsaturated and/or aromatic ring system having 4 or more atoms, including the phosphorous atom to which said groups are bonded, and in which one or more carbon atoms in said monocyclic or polycyclic ring system is optionally replaced with a heteromoiety selected from O, N, NH and N—$C_{1-6}$alkyl;
LG is any suitable leaving group; and
the optional substituents are selected from one or more of halo, $C_{1-6}$alkyl, fluoro-substituted $C_{1-6}$alkyl, $C_{3-6}$cycloalkyl and $C_{6-14}$aryl.

In an embodiment, $R^3$ and $R^4$ are simultaneously or independently selected from phenyl and $C_{1-6}$alkyl. In another embodiment, $R^3$ and $R^4$ are simultaneously or independently selected from phenyl, methyl, ethyl, n-propyl, iso-propyl, sec-butyl, tert-butyl and n-butyl.

In another embodiment, LG is halo, triflate, mesylate or tosylate. In a further embodiment, LG is chloro.

In another embodiment of the disclosure, the compound of formula (II) is

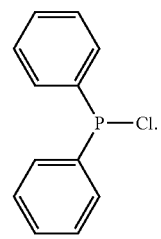

In another embodiment of the disclosure, the method is carried out sequentially, such that the aminoferrocene is first reacted with the Lewis acid, and subsequently, the lithiating reagent is then added to form the lithiated aminoferrocene. The electrophile is then added which reacts with the lithiated aminoferrocene to form the ortho-substituted aminoferrocene.

In an embodiment, the suitable conditions to produce the lithiated aminoferrocene comprise adding the Lewis acid to the aminoferrocene in a suitable solvent, such as tetrahydrofuran, toluene, diethyl ether, t-butyl methyl ether or the like, at a temperature of about −20° C. to about 20° C., suitably about 0° C. In an embodiment, the solvent is t-butyl methyl ether. In a further embodiment, this solution is stirred for about 10 minutes to 1 hour, suitably about 15 minutes. In a further embodiment, the lithiating reagent is added directly to the solution at a temperature of less than about 0° C., optionally less than −50° C., suitably −78° C. In another embodiment, after addition of the lithiating reagent, the solution is warmed to a temperature of about −60° C. to about 0° C., suitably about −40° C. In another embodiment, this solution is stirred for about 0.5 h to about 2 hours, suitably about 1 hour. In another embodiment, the suitable conditions to produce the ortho-substituted aminoferrocene using a sequential addition comprise cooling the solution comprising the lithiated aminoferrocene to a temperature of about −78° C. and adding the desired electrophile, and the solution is then warmed to a temperature of about 0° C. to about 30° C., suitably about 20° C.

In another embodiment, the suitable conditions to produce the ortho-substituted aminoferrocene comprise adding the Lewis base to the aminoferrocene in a suitable solvent, such as tetrahydrofuran, toluene, diethyl ether, t-butyl methyl ether or the like, at a temperature of about −20° C. to about 20° C., suitably about 0° C. In an embodiment, the solvent is t-butyl methyl ether. In a further embodiment, this solution is stirred for about 10 minutes to 1 hour, suitably about 15 minutes. In a further embodiment, the lithiating reagent and the electrophile are added simultaneously to the solution at a temperature of less than about 0° C., optionally less than −50° C., suitably −78° C. In another embodiment, the Lewis base, lithiating reagent and electrophile are all added simultaneously. In another embodiment, after addition of the lithiating reagent and the electrophile, the solution is warmed to a temperature of about −60° C. to about 30° C., suitably between about −40° C. and about 20° C. In another embodiment, this solution is stirred for about 0.5 h to about 2 hours, suitably about 1 hour.

In another embodiment of the disclosure, the ortho-substituted aminoferrocenes of the present disclosure are used as ligands for metal catalysts in synthetic organic reactions. Accordingly, the present disclosure also includes a method of performing a metal-catalyzed synthetic organic reaction comprising contacting suitable starting materials for the synthetic organic reaction with a metal catalyst comprising a ligand of the formula I as defined herein and reacting the starting materials and catalyst under conditions to form the desired product.

In another embodiment of the disclosure, there is also included ortho-substituted aminoferrocenes having the following formula (A) useful as ligands for metal catalysts:

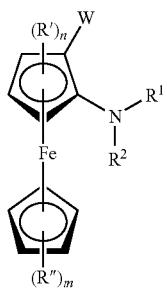

(A)

wherein $R^1$ and $R^2$ are simultaneously or independently selected from $C_{1-10}$alkyl and $C_{3-10}$cycloalkenyl, the latter 2 groups being optionally substituted, or $R^1$ and $R^2$ are linked together to form an optionally substituted monocyclic or bicyclic, saturated ring having 4 or more atoms, including the nitrogen atom to which said groups are bonded;
wherein each R' and R" is independently or simultaneously selected from H, fluoro, chloro, $(C_1$-$C_6)$-alkyl or fluoro-substituted-$(C_1$-$C_6)$-alkyl;
n is 1, 2 or 3;
m is 1, 2, 3, 4 or 5;
W is $PR^3R^4$, $P(Y)R^3R^4$, $SiR^5R^6R^7$, $SnR^5R^6R^7$, halo, S—$R^8$, borate esters, $CH_2$heteroaryl, $CH_2OR^9$, $C_{6-10}$aryl, $C_{6-10}$aryl substituted with one to three halo, $C_{1-10}$alkyl, $OR^3$, $PR^3R^4$ and/or $NR^5R^6$, C(O)H, C(OH)$R^5R^6$, $OR^9$, C(O)$NR^9R^{10}$ or $CH_2NR^9R^{10}$;
$R^3$ and $R^4$ are simultaneously or independently selected from $C_{1-20}$alkyl, $C_{3-20}$cycloalkyl, $C_{6-14}$aryl and heteroaryl, the latter three groups being optionally substituted, or $R^3$ and $R^4$ are linked together to form an optionally substituted monocyclic or polycyclic, saturated, unsaturated and/or aromatic ring system having 4 or more atoms, including the phosphorous atom to which said groups are bonded, and in which one or more carbon atoms in said monocyclic or polycyclic ring system is optionally replaced with a heteromoiety selected from O, N, NH and N—$C_{1-6}$alkyl; $R^5$, $R^6$, $R^7$ and $R^8$ are simultaneously or independently selected from $C_{1-10}$alkyl, $C_{2-10}$alkenyl, $C_{3-10}$cycloalkyl and $C_{6-10}$aryl, each being optionally substituted with one to four optional substituents selected from halo, $C_{1-6}$alkyl, fluoro-substituted $C_{1-6}$alkyl, $C_{3-6}$cycloalkyl and phenyl;
$R^5$, $R^6$, $R^7$ and $R^8$ are simultaneously or independently selected from $C_{1-10}$alkyl, $C_{2-10}$alkenyl, $C_{3-10}$cycloalkyl and $C_{6-10}$aryl, each being optionally substituted with one to four substituents independently selected from halo, $C_{1-6}$alkyl, fluoro-substituted $C_{1-6}$alkyl, $C_{3-6}$cycloalkyl and phenyl, $R^9$ and $R^{10}$ are simultaneously or independently selected from H, C(O)$R^8$, $C_{1-10}$alkyl, $C_{2-10}$alkenyl, $C_{3-10}$cycloalkyl and $C_{6-10}$aryl, each being optionally substituted with one to four substituents independently selected from halo, $C_{1-6}$alkyl, fluoro-substituted $C_{1-6}$alkyl, $C_{3-6}$cycloalkyl and phenyl;
Y is S or O; and
heteroaryl is a 5- or 6-membered ring containing 1 to 5 heteromoieties selected from S, O, N, NH and N—$C_{1-6}$alkyl;
or any stereoisomer and/or enantiomer thereof,
with the proviso that $R^9$ and $R^{19}$ are not simulataneously $C_{1-10}$alkyl.

In an embodiment, $R^3$ and $R^4$ are simultaneously or independently selected from phenyl, $C_{1-6}$alkyl and $C_{3-6}$cycloalkyl, each optionally substituted. In another embodiment, $R^3$ and $R^4$ are simultaneously or independently selected from phenyl, methyl, ethyl, n-propyl, iso-propyl, sec-butyl, tert-butyl, n-butyl and cyclohexyl, each optionally substituted.

In another embodiment, $R^5$, $R^6$, $R^7$ and $R^8$ are simultaneously or independently selected from phenyl, $C_{1-6}$alkyl, $C_{2-6}$alkenyl and $C_{3-6}$cycloalkyl, each optionally substituted. In another embodiment, $R^5$, $R^6$, $R^7$ and $R^8$ are simultaneously or independently selected from phenyl, phenyl, methyl, ethyl, n-propyl, iso-propyl, sec-butyl, tert-butyl, n-butyl and cyclohexyl, each optionally substituted.

In another embodiment of the disclosure, there is also included di-ortho-substituted aminoferrocenes having the following formula (B):

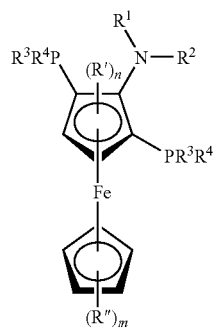

(B)

wherein $R^1$-$R^4$, R' and R" are defined as above, and any stereoisomer and/or enantiomer thereof.

In an embodiment, the synthetic organic reactions are selected from hydrogenation, transfer hydrogenation, hydroformylation, hydrosilylation, hydroboration, hydroamination, hydrovinylation, hydroarylation, hydration, oxidation, epoxidation, reduction, C—C and C—X bond formation, functional group interconversion, kinetic resolution, dynamic kinetic resolution, cycloaddition, Diels-Alder, retro-Diels-Alder, sigmatropic rearrangement, electrocyclic reactions, ring-opening and/or ring-closing olefin metathesis, carbonylation and aziridination. In another embodiment, the C—C and C—X bond formation reaction is selected from Heck, Suzuki-Miyaura, Negishi, Buchwald-Hartwig Amination, α-Ketone Arylation, N-Aryl Amination, Murahashi, Kumada, Negishi and Stille reactions.

In a further embodiment, ortho-phosphine-substituted aminoferrocenes are used as ligands for metal catalysts synthetic organic reactions.

The following non-limiting examples are illustrative of the present disclosure:

EXAMPLES

Materials and Methods

All reagents were purchased from Aldrich, Fisher Scientific, Acros or Strem and used as received unless otherwise indicated. Tetrahydrofuran (THF) was freshly dried and distilled over sodium/benzophenone ketyl under an atmosphere of nitrogen. Diethyl ether and MTBE were distilled over LiAlH$_4$ under an argon atmosphere. Toluene was distilled over sodium under nitrogen. Dichloromethane was distilled over CaH$_2$ under nitrogen. Isopropyllithium was prepared according to a reported procedure (see European Patent 0525881). Alkyllithium reagents were titrated against N-benzylbenzamide to a blue endpoint (see Burchat, A. F.; Chong, J. M.; Nielsen, N. *J. Organomet. Chem.* 1997, 542, 281). All reactions were performed under argon in flame- or oven-dried glassware using syringe-septum cap techniques unless otherwise indicated. Column chromatography was performed on silica gel 60 (70-230 mesh). NMR spectra were obtained on Bruker Avance 300 or Avance 600 instruments and are referenced to TMS or to the residual proton signal of the deuterated solvent for $^1$H spectra, and to the carbon multiplet of the deuterated solvent for $^{13}$C spectra according to values given in *Spectrometric Identification of Organic Compounds, Seventh Edition*, p. 200 and p. 240. FTIR spectra were recorded on an ATI Mattson Research Series spectrometer. Low and high-resolution mass spectral data were obtained on a Kratos Concept 1S Double Focusing spectrometer. Enantiomeric ratios were determined on an Agilent 1100 HPLC system using Chiralpak AS-H, Chiralcel OD-H or Chiralcel-OB-H columns, or on a Hewlett-Packard 6890 GC with a Chirasil DEX-CB column, and were compared against racemic material; for HPLC measurements, samples were detected 254 nm unless otherwise indicated. Optical rotations were measured on a Rudolph Research Autopol III automatic polarimeter. Elemental analyses were performed by Atlantic Microlab, Inc., Norcross, Ga., USA. Melting points were determined on a Kofler hot-stage apparatus and are uncorrected.

Example 1

Preparation of N,N-Dimethylaminoferrocene (11)[19,20]

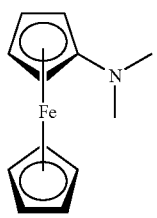

(11)

A solution of aminoferrocene (1.07 g, 5.32 mmol) in acetic acid (15 mL) under argon was treated with paraformaldehyde (1.59 g, 53.2 mmol) and NaBH$_3$CN (1.67 g, 26.6 mmol) and stirred at room temperature for 16 h. The reaction mixture was brought to pH 12 by addition of 6 M aqueous NaOH solution, and extracted with hexanes (3×20 mL). The combined organic extract was washed with water and brine, dried over anhydrous Na$_2$SO$_4$, filtered and concentrated to approx. 5% of its original volume under reduced pressure. The solution was filtered through basic alumina (20 mL) with hexanes, concentrated back to its pre-filtration volume and left to crystallize in a freezer to give N,N-dimethylaminoferrocene (11) (1.11 g, 91%) as orange flakes; mp 69-70° C. (hexanes); IR (KBr) v$_{max}$ 3106, 2981, 2952, 2857, 2827, 2782, 1508 cm$^{-1}$, $^1$H NMR (300 MHz, CDCl$_3$) 4.25 (s, 5H), 3.93 (s, 2H), 3.78 (s, 2H), 2.59 (s, 6H); $^{13}$C NMR (75.5 MHz, acetone-d$_6$) 115.8, 66.5, 63.0, 54.6, 41.5; EIMS [m/z(%)] 229 (M+, 100), 186 (18), 121 (17); HRMS (EI) calcd for C$_{12}$H$_{16}$N$^{56}$Fe: 229.0554. Found 229.0553. Anal. Calcd for C$_{12}$H$_{16}$N$^{56}$Fe: C, 62.91; H, 6.60. Found: C, 62.95; H, 6.60.

Example 2

General Procedure for Lithiation-Electrophile Addition of Dimethylaminoferrocene (11)

To a solution of dimethylaminoferrocene (11) (1 equiv) in THF (0.10 M) at 0° C. under argon was added BF$_3$.OEt$_2$ (1.05 equiv.). After stirring for 15 min, the yellow solution was cooled to −78° C., treated with n-BuLi (1.10 equiv., solution in hexanes), and warmed to −40° C. A distinct color change from yellow to orange-red was observed over a period of 1 h. The reaction mixture was then cooled back to −78° C., quenched with the desired electrophile (1.20 equiv.) and allowed to warm slowly to room temperature. Standard Workup: The reaction mixture was diluted with Et$_2$O and a saturated solution of aq. NaHCO3 was added. The phases were separated and the aqueous layer was extracted once with additional Et$_2$O. The combined organic extract was washed with water and brine, dried over anhydrous Na$_2$SO$_4$, and concentrated on a rotary evaporator under reduced pressure. The crude product was purified by chromatography or recrystallized to give the desired 2-substituted product.

(2a) 2-Trimethylsilyl-1-dimethylaminoferrocene (12a)

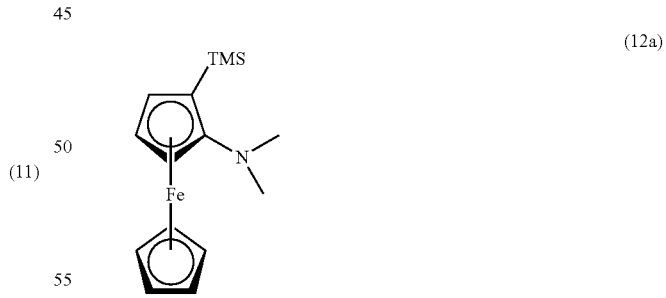

A solution of 11 (229 mg, 1.0 mmol) in THF (10 mL) was sequentially treated with BF$_3$.OEt$_2$ (0.13 mL, 1.05 mmol), n-BuLi (0.48 mL, 2.30 M, 1.10 mmol) and TMSCl (0.15 mL, 1.20 mmol). Standard workup followed by column chromatography (silica gel, 7:3 hexanes/Et$_2$O, R$_f$=0.68) gave 12a (279 mg, 93%) as an orange oil; IR (KBr, neat) max 3096, 2952, 2818, 2774, 1247 cm$^{-1}$; $^1$H NMR (300 MHz, CDCl$_3$) 4.16 (s, 5H), 4.13 (t, 1H, J=2.7 Hz), 4.10 (m, 1H), 3.86 (m, 1H), 2.57 (s, 6H), 0.33 (s, 9H) ppm; $^{13}$C NMR (75.5 MHz, CDCl$_3$) 120.1, 70.6, 68.5, 66.2, 65.9, 58.0, 46.1, 0.5 ppm;

EIMS [m/z(%)] 301 (M+, 100); HRMS (EI) calcd for $C_{15}H_{23}N_{2}Si_{56}Fe$: 301.0949. Found 301.0945.

(2b) 2-[(Diphenylhydroxy)methyl]-1-dimethylaminoferrocene (12b)

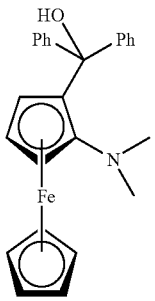

(12b)

A solution of 11 (229 mg, 1.00 mmol) in THF (10 mL) was sequentially treated with $BF_3 \cdot OEt_2$ (0.13 mL, 1.05 mmol), n-BuLi (0.59 mL, 1.86 M, 1.10 mmol) and a solution of benzophenone (218 mg, 1.20 mmol) in THF (8 mL). Standard workup and filtration through a plug of silica gel, eluting with $Et_2O$, gave an orange oil that solidified on standing. Recrystallization from $Et_2O$/hexanes afforded 12b (358 mg, 87%) as a crystalline orange solid; mp 189-190° C. ($Et_2O$/hexanes); IR (KBr) $v_{max}$ 3237, 3081, 2955, 2780 cm$^{-1}$; $^1$H NMR (300 MHz, CDCl$_3$) 8.10 (s, 1H), 7.64-7.62 (m, 2H), 7.38-7.10 (m, 8H), 4.18 (m, 1H), 4.08 (m, 1H), 4.06 (s, 5H), 3.93 (m, 1H), 2.35 (s, 6H) ppm; $^{13}$C NMR (75.5 MHz, CDCl$_3$) 150.0, 146.1, 127.5, 127.2, 127.0, 126.9, 126.4, 126.2, 109.5, 91.8, 78.0, 69.8, 65.9, 63.8, 57.4, 46.7 ppm; EIMS [m/z(%)] 411 (M+, 51), 273 (100); HRMS (EI) calcd for $C_{25}H_{25}NO^{56}Fe$: 411.1285. Found 411.1282. Anal. Calcd for $C_{25}H_{25}NO^{56}Fe$: C, 73.00; H, 6.13. Found: C, 73.05; H, 6.15.

(2c)
2-Dimethylamino-1-(N-phenylferrocenecarboxamide) (12c)

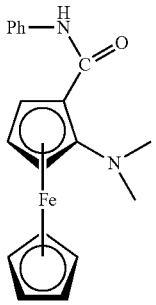

(12c)

A solution of 11 (115 mg, 0.50 mmol) in THF (5 mL) was sequentially treated with $BF_3 \cdot OEt_2$ (66 µL, 0.53 mmol), n-BuLi (0.23 mL, 2.45 M, 0.55 mmol) and phenyl isocyanate (65 µL, 0.60 mmol). Standard workup followed by column chromatography (silica gel, 7:3 hexanes/$Et_2O$, $R_f$=0.15) gave 12c (162 mg, 93%) as an orange oil; IR (KBr, neat) $v_{max}$ 3236, 3179, 3096, 3023, 3003, 2951, 2848, 2786, 1674, 1596, 1550 cm$^{-1}$; $^1$H NMR (300 MHz, CDCl$_3$) 10.88 (b, 1H), 7.65 (d, 2H, J=7.8 Hz), 7.36 (t, 2H, J=7.5 Hz), 7.09 (t, 1H, J=7.5 Hz), 4.89 (m, 1H), 4.31 (m, 1H), 4.28 (t, 1H, J=2.7 Hz), 4.22 (s, 5H), 2.75 (s, 6H); $^{13}$C NMR (75.5 MHz, CDCl$_3$) 168.7, 139.2, 129.0, 123.2, 119.5, 112.5, 70.6, 69.2, 66.8, 66.1, 59.3, 46.8 ppm; EIMS [m/z (%)] 348 (M+, 88), 43 (100); HRMS (EI) calcd for $C_{19}H_{20}N_{2}O^{56}Fe$: 348.0925. Found 348.0931.

(2d) 2-Formyl-1-dimethylaminoferrocene (12d)

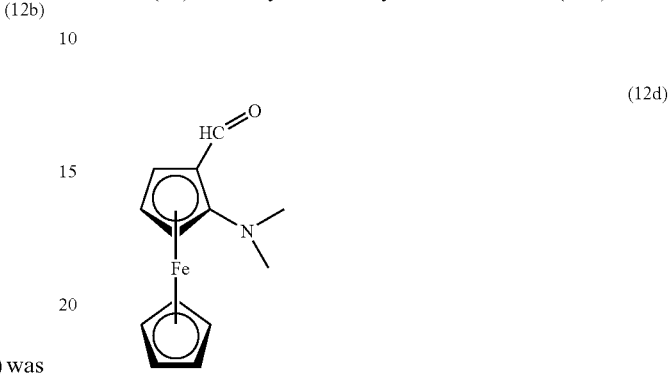

(12d)

A solution of 11 (100 mg, 0.44 mmol) in THF (5 mL) was sequentially treated with $BF_3 \cdot OEt_2$ (58 µL, 0.46 mmol), n-BuLi (0.51 mL, 1.70 M, 0.87 mmol) and DMF (0.17 mL, 2.18 mmol). Standard workup followed by gradient column chromatography (silica gel, 94:5:1 hexanes/$Et_2O$/$Et_3N$, then 84:15:1 hexanes/$Et_2O$/$Et_3N$) gave 12d (85 mg, 76%) as a red-orange oil; IR (KBr, neat) $v_{max}$ 3097, 2943, 2851, 2826, 2785, 1667 cm$^{-1}$, $^1$H NMR (300 MHz, CDCl$_3$) 10.13 (s, 1H), 4.61 (m, 1H), 4.40 (t, 1H, J=2.7 Hz), 4.29 (m, 1H), 4.27 (s, 5H), 2.70 (s, 6H) ppm; $^{13}$C NMR (75.5 MHz, CDCl$_3$) 192.8, 117.5, 71.8, 69.5, 67.7, 66.2, 60.2, 45.6 ppm; EIMS [m/z (%)] 257 (M+, 100), 229 (13), 119 (54), 44 (66); HRMS (EI) calcd for $C_{13}H_{15}NO^{56}Fe$: 257.0503. Found 257.0504.

(2e) Dimethyl-2-(4,4,5,5-tetramethyl-[1,3,2]dioxaborolan-2-yl)-1-aminoferrocene (12e)

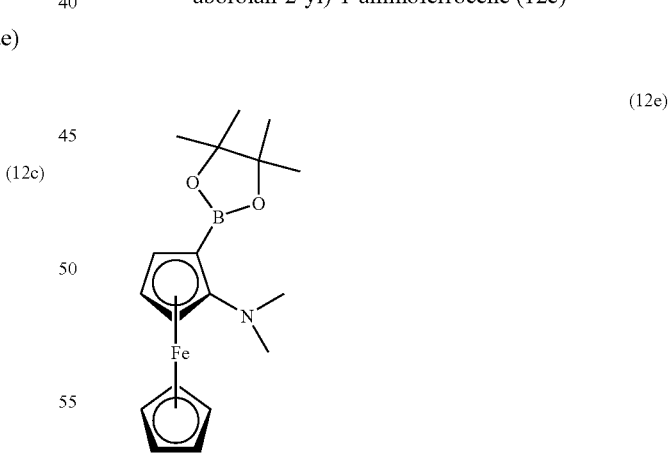

(12e)

A solution of 11 (229 mg, 1.0 mmol) in THF (10 mL) was sequentially treated with $BF_3 \cdot OEt_2$ (0.13 mL, 1.05 mmol), n-BuLi (0.55 mL, 2.00 M, 1.10 mmol) and B(OEt)$_3$ (0.20 mL, 1.20 mmol). Standard workup gave the extract, to which was added pinacol (138 mg, 1.10 mmol) and stirred at room temperature for 5 min. Concentration of the mixture under reduced pressure and column chromatography (basic alumina, hexanes) gave 12e (298 mg, 84%) as an orange oil that solidified on standing; mp 75-76° C. (pentane); IR (KBr) $v_{max}$ 3090, 2978, 2833, 2785, 1141, 1077 cm⁻¹; ¹H NMR (300 MHz, acetone-$d_6$) 4.18 (s, 5H), 4.16 (s, 1H), 4.08 (s, 2H), 2.65 (s, 6H), 1.32 (s, 12H) ppm; ¹³C NMR (75.5 MHz, acetone-$d_6$) 119.6, 82.7, 71.9, 68.3, 67.5, 66.0, 60.1, 43.7, 24.4, 24.1 ppm; EIMS [m/z (%)] 355 (M⁺, 100), 255 (15), 121 (20); HRMS (EI) calcd for $C_{18}H_{26}BNO_2{}^{56}Fe$: 355.1406. Found 355.1411. Anal. Calcd for $C_{18}H_{26}BNO_2Fe$: C, 60.89; H, 7.38. Found: C, 60.96; H, 7.48.

(2f) 2-Diphenylphosphino-dimethylaminoferrocene (12f)

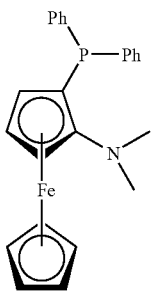

(12f)

A solution of 11 (229 mg, 1.00 mmol) in THF (10 mL) was sequentially treated with $BF_3 \cdot OEt_2$ (0.13 mL, 1.05 mmol), n-BuLi (0.45 mL, 2.45 M, 1.10 mmol) and $Ph_2PCl$ (0.22 mL, 1.20 mmol). Standard workup followed by column chromatography of the pre-adsorbed product (silica gel, $Et_2O$) gave an orange solid. Recrystallization from $Et_2O$ afforded 12f (317 mg, 77%) as orange needles in two crops; mp 146-148° C. ($Et_2O$); IR (KBr) $v_{max}$ 3090, 3050, 2952, 2840, 2780, 1494 cm⁻¹; ³¹P NMR (121.5 MHz, $CDCl_3$) –20.37; ¹H NMR (600 MHz, $CDCl_3$) 7.55-7.52 (m, 2H), 7.39 (m, 3H), 7.28 (m, 5H), 4.20 (s, 1H), 4.13 (s, 5H), 4.10 (t, 1H, J=2.4 Hz), 3.50 (s, 1H), 2.69 (s, 6H) ppm; ¹³C NMR (150.9 MHz, $CDCl_3$) 139.8 (d, J=11.0 Hz), 137.9 (d, J=10.6 Hz), 135.3 (d, J=22.6 Hz), 132.4 (d, J=18.1 Hz), 129.0, 128.1 (d), 128.0 (d), 127.8 (d, J=18.1 Hz), 68.7, 68.5 (d, J=3.0 Hz), 65.9 (d, J=10.6 Hz), 65.2, 60.1, 45.5 ppm; EIMS [m/z (%)] 413 (M⁺, 100); HRMS (EI) calcd for $C_{24}H_{24}NP{}^{56}Fe$: 413.0995. Found 413.0991. Anal. Calcd for $C_{24}H_{24}NPFe$: C, 69.75; H, 5.85. Found: C, 69.87; H, 5.94.

(2g) 2-Thiophenyl-dimethylaminoferrocene (12g)

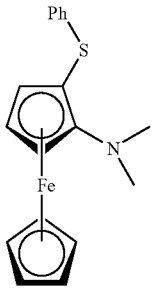

(12g)

A solution of 11 (229 mg, 1.00 mmol) in THF (10 mL) was sequentially treated with $BF_3 \cdot OEt_2$ (0.13 mL, 1.05 mmol), n-BuLi (0.51 mL, 2.15 M, 1.10 mmol) and a solution of $(PhS)_2$ (262 mg, 1.20 mmol) in THF (2 mL). Standard workup followed by gradient column chromatography (silica gel, 99:1 hexanes/$Et_3N$, then 97:2:1 hexanes/$Et_2O$/$Et_3N$) gave 12g (278 mg, 82%) as an orange oil that solidified on standing; mp 79-80° C. (pentane); IR (neat) $v_{max}$ 3098, 3087, 3055, 2967, 2847, 2785, 1498, 1002 cm⁻¹; ¹H NMR (300 MHz, $CDCl_3$) 7.20-7.15 (m, 2H), 7.08-7.01 (m, 3H), 4.32 (s, 5H), 4.22 (m, 1H), 4.16-4.12 (m, 2H), 2.66 (m, 6H) ppm; ¹³C NMR (75.5 MHz, $CDCl_3$) 140.8, 128.6, 125.3, 124.5, 115.9, 73.0, 69.2, 65.9, 64.5, 58.5, 44.4 ppm; EIMS [m/z (%)] 337 (M⁺, 51), 229 (100); HRMS (EI) calcd for $C_{18}H_{19}NS{}^{56}Fe$: 337.0587. Found 337.0588. Anal. Calcd for $C_{18}H_{19}NSFe$: C, 64.10; H, 5.68. Found: C, 64.08; H, 5.61.

(2h) 2-Trimethylstannyl-dimethylaminoferrocene (12h)

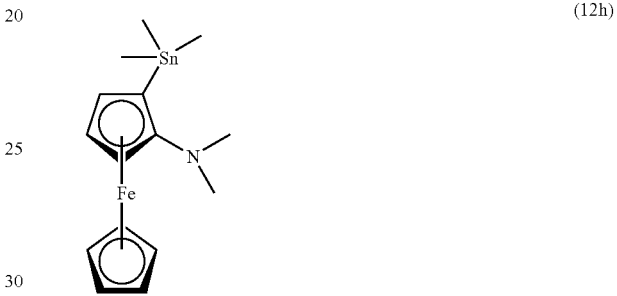

A solution of 11 (300 mg, 1.31 mmol) in THF (13 mL) was sequentially treated with $BF_3 \cdot OEt_2$ (0.17 mL, 1.37 mmol), n-BuLi (0.59 mL, 2.45 M, 1.44 mmol) and $Me_3SnCl$ (1.57 mL, 1.57 mmol). Standard workup followed by column chromatography (basic alumina, hexanes) gave 12h (466 mg, 91%) as an orange oil; IR (KBr, neat) $v_{max}$ 3093, 2980, 2940, 2910, 2825, 2775 cm⁻¹; ¹H NMR (300 MHz, $CDCl_3$) 4.16 (s, 6H), 4.06 (m, 1H), 3.81 (m, 1H), 2.59 (s, 6H), 0.32 (s, 9H) ppm; ¹³C NMR (75.5 MHz, $CDCl_3$) 120.2, 70.9, 67.8, 66.4, 60.4, 58.0, 45.1, –7.6 ppm; EIMS [m/z (%)] 393 (M⁺, 100), 348 (88); HRMS (EI) calcd for $C_{15}H_{23}N{}^{118}Sn{}^{56}Fe$: 391.0198. Found 391.0194.

(2i) 2-Iodo-dimethylaminoferrocene (12i)

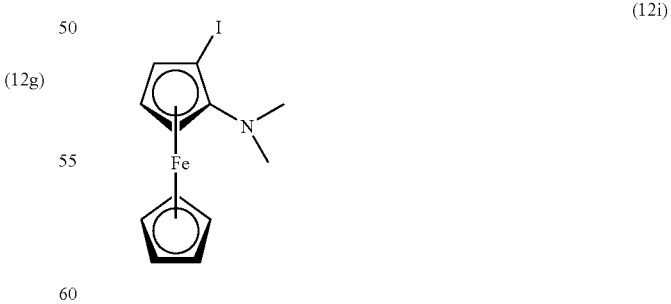

A solution of 11 (250 mg, 1.09 mmol) in THF (10 mL) was sequentially treated with $BF_3 \cdot OEt_2$ (0.14 mL, 1.15 mmol), n-BuLi (0.49 mL, 2.45 M, 1.20 mmol) and a solution of $(ICH_2)_2$ (369 mg, 1.31 mmol) in THF (2 mL). Standard workup including an additional washing with sat. aq. $Na_2S_2O_3$ solution and column chromatography (basic alumina, hexanes) gave 12i (334 mg, 94%) as a light-sensitive orange oil; IR (neat) $v_{max}$ 3087, 2948, 2777, 1486 cm$^{-1}$; $^1$H NMR (300 MHz, CDCl$_3$) 4.28 (m, 1H), 4.21 (s, 5H), 4.05 (t, 1H, J=2.7 Hz), 4.02 (m, 1H), 2.69 (s, 6H) ppm; $^{13}$C NMR (75.5 MHz, CDCl$_3$) 113.4, 71.9, 71.1, 64.8, 56.3, 45.5, 38.7 ppm; EIMS [m/z (%)] 355 (M$^+$, 100), 290 (24); HRMS (EI) calcd for C$_{12}$H$_{14}$NI$^{56}$Fe: 354.9520. Found 354.9517.

(2j)
2-Dicyclohexylphosphino-1-dimethylaminoferrocene (12j)

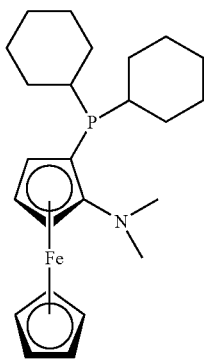

In a dry round bottom flask under argon, an ice-cold solution of dimethylaminoferrocene 11 (229 mg, 1.00 mmol) in THF (10 mL) was treated with BF$_3$·OEt$_2$ (0.13 mL, 1.05 mmol). After 15 min, the yellow solution was cooled to −40° C. and n-BuLi (0.46 mL of 2.40 M solution in hexanes, 1.10 mmol) was added by syringe to give an orange-red solution that was stirred for 1 h before ClPCy$_2$ (0.24 mL, 1.10 mmol) was added and the mixture was allowed to warm to room temperature. The reaction mixture was diluted with Et$_2$O (10 mL) and worked up with saturated aqueous NaHCO$_3$ solution (10 mL). The organic layer was washed with H$_2$O (1×10 mL), brine (1×10 mL), dried over anhydrous Na$_2$SO$_4$ and concentrated to dryness. The residue was redissolved in pentane and chromatographed on silica gel (25 mL), eluting with 95:5 pentane/Et$_2$O to give 397 mg (77%) of the desired aminophosphine 12j as a moderately air-sensitive viscous orange oil. R$_f$ (SiO$_2$, 9:1 hex/EtOAc) 0.50; IR (CHCl$_3$): $v_{max}$ 2920, 2848, 1489, 1446 cm$^{-1}$, $^{31}$P NMR (121 MHz, acetone-d$_6$): δ −12.3; $^1$H NMR (300 MHz, acetone-d$_6$): δ 4.22 (s, 5H), 4.15 (t, 1H, J=1.1 Hz), 4.04 (t, 1H, J=2.3 Hz), 3.92 (t, 1H, J=1.7 Hz), 2.75 (s, 6H), 2.49-2.41 (m, 1H), 2.00-1.93 (m, 1H), 1.92-1.81 (m, 3H), 1.77-1.67 (m, 2H), 1.67-1.61 (m, 1H), 1.61-1.52 (m, 3H), 1.50-1.20 (m, 7H), 1.20-1.06 (m, 2H), 1.06-0.97 (m, 1H), 0.90-0.79 (m, 1H); $^{13}$C NMR (75.5 MHz, acetone-d$_6$) δ 118.0 (d, $J^{13}_{C-}{}^{31}_P$=14.0 Hz), 67.5, 66.6 (d, $J^{13}_{C-}{}^{31}_P$=3.4 Hz), 63.3 (d, $J^{13}_{C-}{}^{31}_P$=25.3 Hz), 63.2, 61.3 (d, $J^{13}_{C-}{}^{31}_P$=1.5 Hz), 43.9 (d, $J^{13}_{C-}{}^{31}_P$=13.2 Hz), 35.0 (d, $J^{13}_{C-}{}^{31}_P$=15.9 Hz), 33.2 (d, $J^{13}_{C-}{}^{31}_P$=13.2 Hz), 32.2 (d, $J^{13}_{C-}{}^{31}_P$=20.6 Hz), 30.2 (d, $J^{13}_{C-}{}^{31}_P$=15.9 Hz), 29.5 (d, $J^{13}_{C-}{}^{31}_P$=10.8 Hz), 29.0, 27.3 (d, $J^{13}_{C-}{}^{31}_P$=11.8 Hz), 27.2 (d, $J^{13}_{C-}{}^{31}_P$=6.5 Hz), 27.0 (d, $J^{13}_{C-}{}^{31}_P$=12.8 Hz), 26.8 (d, $J^{13}_{C-}{}^{31}_P$=8.3 Hz), 26.3 (d, $J^{13}_{C-}{}^{31}_P$=15.5 Hz). EIMS (m/z (%)): 425 (M$^+$, 87), 130 (62), 55 (100), 41 (94); HRMS (EI; m/z): calcd for C$_{24}$H$_{36}$NP$^{56}$Fe 425.1936. Found 425.1934.

Example 3

Preparation of N,N,N"N"-Tetramethyl-2,2"-diamino-1,1"-biferrocene (13) from (12i)[21]

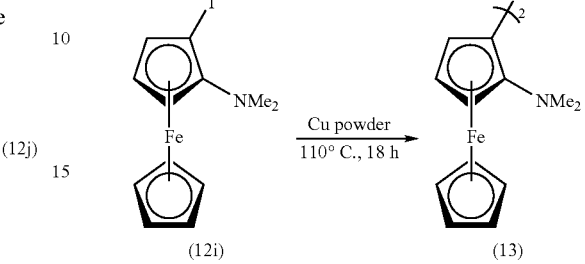

A mixture of 12i (88 mg, 0.25 mmol), dichloromethane (5 mL) and purified Cu powder (787 mg, 12.4 mmol) was concentrated to dryness under reduced pressure. The resulting solid mass was heated under argon at 110° C. for 18 h. After cooling to room temperature, the solid mass was taken up in dichloromethane (20 mL) and filtered through Celite in a sintered funnel. Concentration of the filtrate under reduced pressure and gradient column chromatography (neutral alumina, 98:2 to 95:5 hexanes/Et$_2$O) gave, sequentially, meso-13 (14 mg, 26%) as an orange solid, and rac-13 (15 mg, 26%) as an orange solid. meso-13. mp 198-200° C. (abs. EtOH); IR (KBr) $v_{max}$ 3088, 3073, 2999, 2940, 2822, 2780, 1472, 1411 cm$^{-1}$; $^1$H NMR (300 MHz, CDCl$_3$) 4.88-4.86 (m, 2H), 4.14-4.13 (m, 2H), 4.05 (s, 10H), 3.99 (t, 2H, J=2.7 Hz), 2.73 (s, 12H) ppm; $^{13}$C NMR (75.5 MHz, CDCl$_3$) 112.0, 76.4, 69.2, 66.4, 62.5, 57.7, 46.2 ppm; EIMS [m/z (%)] 456 (M$^+$, 100); HRMS (EI) calcd for C$_{24}$H$_{28}$N$_2$$^{56}$Fe$_2$: 456.0949. Found 456.0950. rac-13. $^1$H NMR (300 MHz, CDCl$_3$) 4.38-4.37 (m, 2H), 4.32 (s, 10H), 3.93-3.92 (m, 4H), 2.38 (s, 12H) ppm; EIMS [m/z (%)] 456 (M$^+$, 100); HRMS (EI) calcd for C$_{24}$H$_{28}$N$_2$$^{56}$Fe$_2$: 456.0949. Found 456.0941.

Example 4

Preparation of 2-Acetoxy-dimethylaminoferrocene (14) from (12i)[22]

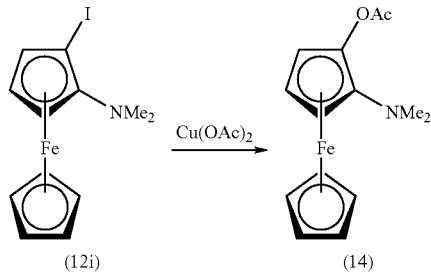

A solution of 12i (144 mg, 0.41 mmol) in absolute EtOH (3 mL) was treated with Cu(OAc)$_2$·H$_2$O (95 mg, 0.50 mmol) and heated to reflux for 60 min to give a dark mixture. After cooling to room temperature, the mixture was concentrated under reduced pressure. The residue was dissolved in Et$_2$O and filtered through Celite in a sintered funnel to give 14 (99 mg, 86%) as an orange oil that solidified on standing; mp 52-54° C. (pentane); IR (KBr, neat) $v_{max}$ 3103, 2974, 2851, 2793, 1752, 1210 cm$^{-1}$; $^1$H NMR (300 MHz, acetone-d$_6$) 4.29, 4.17 (dd, 1H, J=2.4, 1.5 Hz), 3.78 (dd, 1H, J=2.7, 0.9 Hz), 3.68 (t, 1H, J=2.7 Hz), 2.61 (s, 6H), 2.15 (s, 3H) ppm; $^{13}$C NMR (75.5 MHz, acetone-d$_6$) 169.8, 106.4, 69.2, 67.6, 60.0, 57.5, 55.4, 43.5, 21.2 ppm; EIMS [m/z (%)] 287 (M$^+$, 71), 245 (100); HRMS (EI) calcd for C$_{14}$H$_{17}$NO$_2$$^{56}$Fe: 287.0608. Found 287.0606. Anal. Calcd for C$_{14}$H$_{17}$NO$_2$Fe: C, 58.56; H, 5.97. Found: C, 58.56; H, 5.97.

Example 5

Preparation of 2-Dimethylamino-3-trimethylsilanyl-ferrocenecarboxaldehyde (15) from (12a)

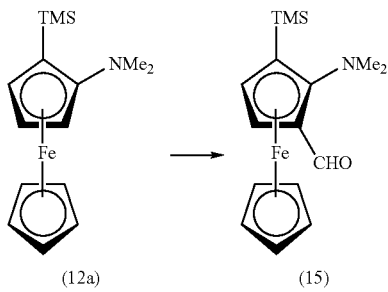

To a solution of dimethylaminoferrocene 12a (81 mg, 0.27 mmol) in THF (2.5 mL) at 0° C. under argon was added BF$_3$.OEt$_2$ (35 μL, 0.28 mmol). After stirring for 15 min, the yellow solution was cooled to −78° C., treated with n-BuLi (0.28 mL, 2.00 M, 0.56 mmol) and immediately warmed to −40° C. for 1 h. The reaction mixture was then cooled back to −78° C. before addition of DMF (52 μL, 0.67 mmol) and allowed to warm slowly to room temperature. Standard workup followed by gradient column chromatography (silica gel, 96:2:2 to 88:10:2 hexane/Et$_2$O/Et$_3$N) gave 15 (53 mg, 60%) as a dark red oil; IR (KBr) $v_{max}$ 3096, 2955, 2926, 2853, 2780, 1669 cm$^{-1}$; $^1$H NMR (300 MHz, CDCl$_3$) 10.23 (s, 1H), 4.78 (s, 1H), 4.36 (s, 1H), 4.28 (s, 5H), 2.78 (s, 6H), 0.29 (s, 9H) ppm; $^{13}$C NMR (75.5 MHz, CDCl$_3$) 193.7, 120.5, 76.4, 75.5, 74.4, 70.3, 68.4, 47.3, 0.3 ppm; EIMS [m/z (%)] 329 (M$^+$, 100); HRMS (EI) calcd for C$_{16}$H$_{23}$NOSi$^{56}$Fe: 329.0898. Found 329.0893.

Example 6

Preparation of 4-Phenylacetophenone (17) from 4-Chloroacetophenone (16) Using (12f) as a Ligand in a Metal Catalyzed Cross Coupling

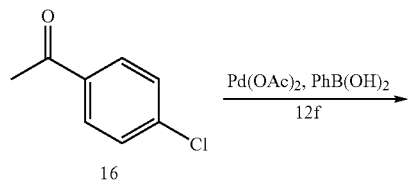

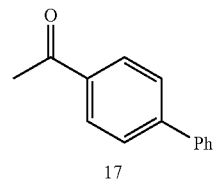

An oven-dried reaction tube under argon containing a mixture of phenylboronic acid (91 mg, 0.75 mmol), CsF (228 mg, 1.50 mmol) and Pd(OAc)$_2$ (2 mg, 0.01 mmol) in dioxane (2.5 mL) was treated with 4-chloroacetophenone (16) (65 μL, 0.50 mmol) and stirred at room temperature for 5 min. The mixture was heated to reflux for 22 h then cooled to room temperature, diluted with Et$_2$O (7 mL) and filtered through a pipette containing a plug of silica gel while eluting with additional Et$_2$O. Evaporation of the solvent under reduced pressure and recrystallization of the crude product from hexane containing a small amount of EtOAc gave 17 as a colorless crystalline solid (86 mg, 88%); mp 123-125° C. (hexane/EtOAc; lit. 116-117° C.); $^1$H NMR (300 MHz, CDCl$_3$) 8.05 (d, 2H, J=8.4 Hz), 7.69 (d, 2H, J=8.4 Hz), 7.63 (d, 2H, J=7.2 Hz), 7.50-7.40 (m, 3H), 2.64 (s, 3H) ppm; $^{13}$C NMR (75.5 MHz, CDCl$_3$) 197.7, 145.8, 139.8, 135.8, 128.93, 128.89, 128.2, 127.24, 127.20, 26.6 ppm.

Example 6

Preparation of N-(4-Acetylphenyl)morpholine (18) from 4-Chloroacetophenone (16) Using (12f) as a Ligand in a Metal Catalyzed Cross Coupling

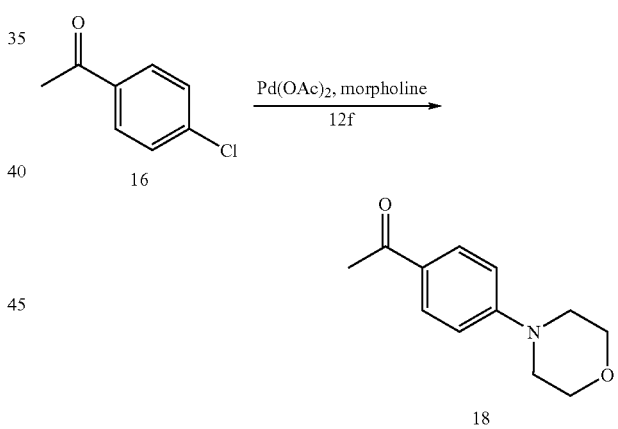

An oven-dried reaction tube under argon containing a mixture of Pd$_2$(dba)$_3$.CHCl$_3$ (10 mg, 0.01 mmol) and NaOt-Bu (67 mg, 0.70 mmol) in PhMe (2.5 mL) was treated with 4-chloroacetophenone (16) (65 μL, 0.50 mmol) and morpholine (52 μL, 0.60 mmol). The resulting green-brown mixture was heated at 100° C. for 22 h. After cooling to room temperature, the reaction mixture was diluted with Et$_2$O (5 mL) and filtered through a pipette containing a plug of silica gel while eluting with additional Et$_2$O. Evaporation of the solvent under reduced pressure and column chromatography of the pre-adsorbed crude material (silica gel, 83:2:15 to 78:2:20 hexane/Et$_3$N/EtOAc, R$_f$=0.38) gave 18 (76 mg, 74%) as a pale yellow solid; mp 99-100° C. (Et$_2$O/hexanes); $^1$H NMR (300 MHz, CDCl$_3$) 7.90 (d, 2H, J=9.0 Hz), 6.87 (d, 2H, J=9.0 Hz), 3.86 (t, 4H, J=4.8 Hz), 3.31 (t, 4H, J=5.1 Hz), 2.53 (s, 3H) ppm; $^{13}$C NMR (75.5 MHz, CDCl$_3$) 196.4, 154.2, 130.3, 128.1, 113.2, 66.5, 47.5, 26.1 ppm.

Example 7

General Procedure for the Asymmetric Lithiation-Dimethylformamide Addition of (11) Using n-BuLi and Chiral Diamine Ligands[9,23,24]

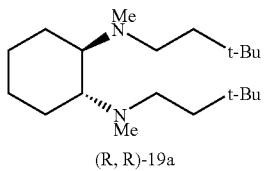

(R, R)-19a

A solution of ligand (R,R)-19a (324 mg, 1.05 mmol) in t-BuOMe (2 mL) was cooled to −40° C., treated with n-BuLi (0.59 mL, 1.77 M, 1.05 mmol) and stirred for 20 min. The solution was transferred by cannula to a mixture of 11.BF$_3$ (11 complexed with BF$_3$) at −78° C., prepared according to the Example 2 [11 (115 mg, 0.50 mmol), BF$_3$.OEt$_2$ (66 µL, 0.53 mmol), t-BuOMe (5 mL)]. After stirring for 10 min, the mixture was warmed to −40° C. for 2 h. After cooling back to −78° C., DMF (96 µL, 1.25 mmol) was added, and the mixture was allowed to warm to room temperature. Standard workup followed by gradient column chromatography (93:5:2 to 88:10:2 hexanes/Et$_2$O/Et$_3$N) gave (−)-12d (91 mg, 71%); [α]$^{20}_{633}$ −14.7 (c 0.85, acetone); CSP HPLC analysis (Chiralpak AS-H; eluent: 80:20 hexanes/i-PrOH, 1.0 mL/min) determined 61:39 er, 22% ee [t$_R$(major)=12.48 min, t$_R$(minor)=26.38 min]. The results for the various chiral diamines are shown in Table 1.

Example 8

General Procedure for Asymmetric Lithiation-Dimethylformamide Addition of 11 Using Ligand (R,R)-19a, (R,R)-19b or (S,S)-19c and Various Lithiating Reagents A solution of (R,R)-19a (324 mg, 1.05 mmol) in t-BuOMe (2 mL) was cooled to −40° C., treated with i-PrLi (0.59 mL, 1.77 M, 1.05 mmol) and stirred for 20 min at that temperature. The solution was transferred by cannula to a mixture of 11.BF$_3$ at −78° C. [prepared by addition of BF$_3$.OEt$_2$ (66 µL, 0.53 mmol) to a solution of 11 (115 mg, 0.50 mmol) in t-BuOMe (5 mL) at 0° C. and stirring for 10 min]. The resulting reaction mixture was allowed to warm slowly to −40° C. over 2 h and then held at that temperature for an additional hour. After cooling back to −78° C., DMF (96 µL, 1.25 mmol) was added and the mixture was allowed to warm to room temperature. The reaction mixture was diluted with Et$_2$O and worked-up by addition of a saturated solution of aqueous NaHCO$_3$. The aqueous layer was extracted with Et$_2$O (2×10 mL) and the combined organic extract was washed with H$_2$O (1×10 mL), saturated NaCl solution (1×10 mL), dried over anhydrous Na$_2$SO$_4$ and concentrated under reduced pressure on a rotary evaporator. Gradient flash column chromatography (95:5 then 90:10 CH$_2$Cl$_2$/Et$_2$O) gave sequentially recovered starting material (11) and aldehyde 12d (71 mg, 55%); CSP HPLC analysis (Chiralpak AS-H; eluent: 80:20 hexanes/i-PrOH, 1.0 mL/min) determined the enantiomeric ratio (er) of 12d. The results for the various lithiating reagents, as well as the equivalents of the lithiating reagent used are shown in Table 2. As seen in Table 2, using 2.1 equivalents (lithiating reagent and ligand) of isopropyllithium resulted in the highest enantiomeric ratio of 12d.

Example 9

General Procedure for the Asymmetric Lithiation-Dimethylformamide Addition of 11 Using Ligand (R,R)-19a, (R,R)-19b or (S,S)-19c plus 2-dimethylaminoethanol or LDA and Various Lithiating Agents A solution of (S,S)-19c (134 mg, 0.53 mmol) in t-BuOMe (4 mL) was cooled to −40° C. and treated with i-PrLi (1.18 mL, 1.34 M, 1.58 mmol) and 2-dimethylaminoethanol (47 mg, 0.53 mmol), and stirred for 20 min at that temperature. The solution was transferred by cannula to a mixture of 11.BF$_3$ at −78° C. [prepared by addition of BF$_3$.OEt$_2$ (66 µL, 0.53 mmol) to a solution of 11 (115 mg, 0.50 mmol) in t-BuOMe (5 mL) at 0° C. and stirring for 10 min]. The resulting reaction mixture was allowed to warm slowly to −40° C. over 2 h and then held at that temperature for an additional hour. After cooling back to −78° C., DMF (96 µL, 1.25 mmol) was added and the mixture was allowed to warm to room temperature. The reaction mixture was diluted with Et$_2$O and worked-up by addition of a saturated solution of aqueous NaHCO$_3$. The aqueous layer was extracted with Et$_2$O (2×10 mL) and the combined organic extract was washed with H$_2$O (1×10 mL), saturated NaCl solution (1×10 mL), dried over anhydrous Na$_2$SO$_4$ and concentrated under reduced pressure on a rotary evaporator. Gradient flash column chromatography (95:5 then 90:10, then 80:20 CH$_2$Cl$_2$/Et$_2$O) gave, sequentially, recovered starting material (11) aldehyde 12d and dialdehyde 12dd; CSP HPLC analysis (Chiralpak AS-H; eluent: 80:20 hexanes/i-PrOH, 1.0 mL/min) determined the enantiomeric ratio (er) of 12d. The results for the various lithiating reagents, as well as the equivalents of the lithiating reagent used are shown in Table 3. As seen in Table 3, using 2.1 equivalents (lithiating reagent: ligand) of isopropyllithium resulted in the highest enantiomeric ratio of 12d. As noted in Tables 1, 2 and 3 above, either enantiomeric form of ortho substituted products can be obtained since both enantiomers of ligands 19a, 19b and 19c are readily available by known resolution methods. The procedures of Examples 10-13, 15, and 16 describe the use of various electrophiles. In an embodiment of the disclosure, the methyl stannane (12h) serves as a precursor to all other products via transmetalation with MeLi.

Example 10

Preparation of (S)-2-Dimethylamino-1-ferrocenecarboxaldehyde [(S)-12d] and (S)-2-Dimethylamino-1,1'-ferrocene-di-carboxaldehyde [(S)-12dd]

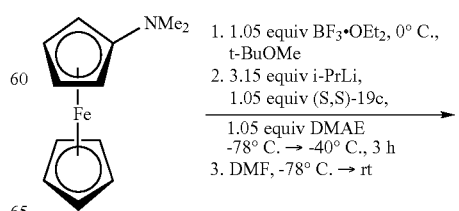

11

-continued

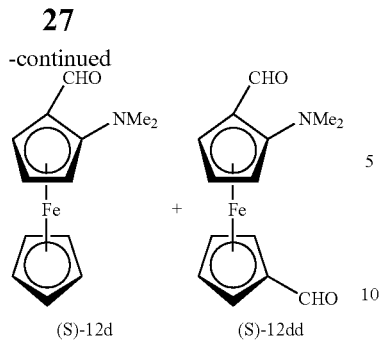

(S)-12d       (S)-12dd

A solution of (S,S)-19c (134 mg, 0.53 mmol) in t-BuOMe (4 mL) was cooled to −40° C., treated with i-PrLi (1.18 mL, 1.34 M, 1.58 mmol) and as solution of dimethylaminoethanol (DMAE, 47 mg, 0.53 mmol) in t-BuOMe (1 mL), and the mixture was stirred for 20 min. This solution was transferred by cannula to a mixture of 11.BF$_3$ at −78° C. [prepared by addition of BF$_3$.OEt$_2$ (66 μL, 0.53 mmol) to a solution of 11 (115 mg, 0.50 mmol) in t-BuOMe (5 mL) at 0° C. and stirring for 10 min]. After stirring for 10 min, the mixture was allowed to warm slowly to −40° C. over 2 h and then held at that temperature for an additional hour. After cooling back to −78° C., the electrophile DMF (96 μL, 1.25 mmol) was added and the mixture was allowed to warm to room temperature over 16 h. The reaction mixture was diluted with Et$_2$O and worked-up by addition of a saturated solution of aqueous NaHCO$_3$. The aqueous layer was extracted with Et$_2$O (2×10 mL) and the combined organic extract was washed with H$_2$O (1×10 mL), saturated NaCl solution (1×10 mL), dried over anhydrous Na$_2$SO$_4$ and concentrated under reduced pressure on a rotary evaporator. Gradient flash column chromatography (95:5 to 90:10 to 80:20 CH$_2$Cl$_2$/Et$_2$O) gave, sequentially 11 (22 mg, 19%), (S)-12d (78 mg, 61%) as a red oil and (S)-12dd (13 mg, 9%) as a red oil. (S)-12d. $[\alpha]^{20}_{633}$+28.8 (c 0.85, acetone); CSP HPLC analysis (Chiralpak AS-H; eluent: 80:20 hexanes/i-PrOH, 1.0 mL/min) determined an enantiomeric ratio (er) of 91:9 (82% ee) [t$_R$(minor)=12.48 min, t$_R$(major)=26.38 min]. All other spectroscopic data matched racemic 12d (vide supra). Data for (S)-12dd. dark red film; $[\alpha]^{20}_D$ (c CHCl$_3$); CSP HPLC analysis (Chiralpak AS-H; eluent: 60:40 hexanes/i-PrOH, 1.0 mL/min) determined an enantiomeric ratio (er) of 91.5:8.5 (83% ee) [t$_R$(minor)=28.19 min, t$_R$(major)=40.3 min] IR (KBr): v$_{max}$ 3113, 3099, 2959, 2870, 2806, 1644, 1522, 1233, 1034 cm$^{-1}$; $^1$H NMR (300 MHz, CDCl$_3$) 10.13 (s, 1H), 9.93 (s, 1H), 4.90-4.89 (m, 1H), 4.86-4.85 (m, 1H), 4.70-4.66 (m, 2H), 4.43 (t, 1H, J=2.7 Hz), 4.27 (dd, 1H, J=2.7, 1.8 Hz), 2.73 (s, 6H) ppm; $^{13}$C NMR (75.5 MHz, CDCl$_3$) 192.8, 192.1, 119.6, 80.2, 74.1, 73.5, 70.65, 70.60, 70.4, 68.5, 67.3, 60.1, 44.6 ppm; EIMS (m/z, (%)): 285 (M-BAr$_F$, (100)). HRMS (EI; m/z): calcd for C$_{12}$H$_{15}$NO$_2$$^{56}$Fe 285.0452. Found 285.0446. Anal. calcd for C$_{12}$H$_{15}$NO$_2$Fe: C, 58.98; H, 5.30. Found C, 58.89; H, 5.12.

Example 11

Preparation of (R)-2-Dimethylamino-1-(N-phenyl-ferrocenecarboxamide) [(R)-12c]

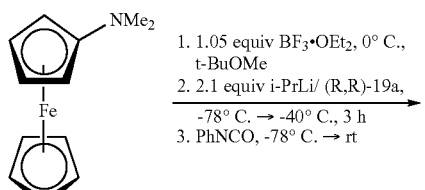

1. 1.05 equiv BF$_3$•OEt$_2$, 0° C., t-BuOMe
2. 2.1 equiv i-PrLi/ (R,R)-19a, −78° C. → −40° C., 3 h
3. PhNCO, −78° C. → rt

11

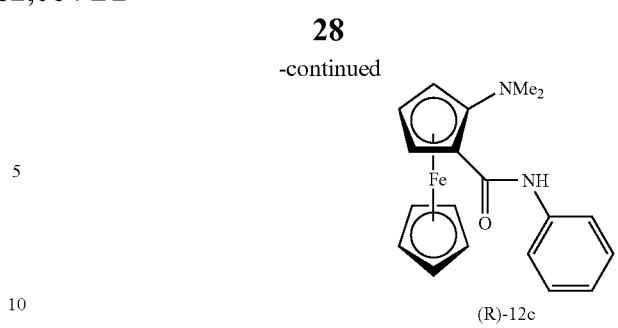

(R)-12c

A solution of (R,R)-19a (327 mg, 1.05 mmol) in t-BuOMe (3 mL) was cooled to −40° C., treated with i-PrLi (1.05 mL, 1.00 M, 1.05 mmol), and the mixture was stirred for 20 min. This solution was transferred by cannula to a mixture of 11.BF$_3$ at −78° C. [prepared by addition of BF$_3$.OEt$_2$ (66 μL, 0.53 mmol) to a solution of 11 (115 mg, 0.50 mmol) in t-BuOMe (5 mL) at 0° C. and stirring for 10 min]. After stirring for 10 min, the mixture was allowed to warm slowly to −40° C. over 2 h and then held at that temperature for an additional hour. After cooling back to −78° C., the phenylisocyanate (0.14 mL, 1.25 mmol) was added and the mixture was allowed to warm to room temperature over 16 h. The reaction mixture was diluted with Et$_2$O and worked-up by addition of a saturated solution of aqueous NaHCO$_3$. The aqueous layer was extracted with Et$_2$O (2×10 mL) and the combined organic extract was washed with H$_2$O (1×10 mL), saturated NaCl solution (1×10 mL), dried over anhydrous Na$_2$SO$_4$ and concentrated under reduced pressure on a rotary evaporator. Flash column chromatography (88:10:2 hexanes/EtOAc/Et$_3$N) gave (R)-12c (172 mg, 72%) as a dark orange oil. (R)-12c. $[\alpha]^{20}_D$ +113 (c 1.00, CHCl$_3$); CSP HPLC analysis (Chiralcel OD-H; eluent: 99:1 hexanes/i-PrOH, 1.0 mL/min) determined an enantiomeric ratio (er) of 88:12 (76% ee) [t$_R$(minor)=17.60 min, t$_R$(major)=18.80 min]. All other spectroscopic data matched racemic 12c (vide supra).

Example 12

Preparation of (R)-2-Trimethylstannyl-1-dimethylaminoferrocene [(R)-12h)]

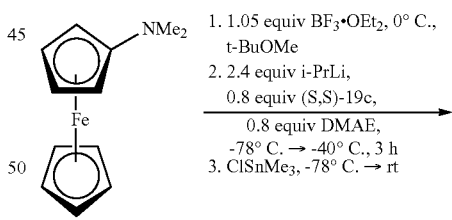

1. 1.05 equiv BF$_3$•OEt$_2$, 0° C., t-BuOMe
2. 2.4 equiv i-PrLi, 0.8 equiv (S,S)-19c, 0.8 equiv DMAE, −78° C. → −40° C., 3 h
3. ClSnMe$_3$, −78° C. → rt

11

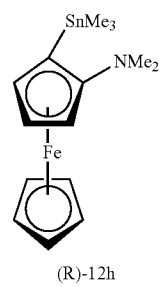

(R)-12h

A solution of (S,S)-19c (102 mg, 0.40 mmol) in t-BuOMe (4 mL) was cooled to −40° C., treated with i-PrLi (0.90 mL, 1.34 M, 1.20 mmol) and as solution of dimethylaminoethanol (DMAE, 36 mg, 0.40 mmol) in t-BuOMe (1 mL), and the mixture was stirred for 20 min. This solution was transferred by cannula to a mixture of 11.BF$_3$ at −78° C. [prepared by addition of BF$_3$.OEt$_2$ (66 μL, 0.53 mmol) to a solution of 11 (115 mg, 0.50 mmol) in t-BuOMe (5 mL) at 0° C. and stirring for 10 min]. After stirring for 10 min, the mixture was allowed to warm slowly to −40° C. over 2 h and then held at that temperature for an additional hour. After cooling back to −78° C., chlorotrimethylstannane (1 mL, 1.0 M solution in hexane, 1.0 mmol) was added and the mixture was allowed to warm to room temperature over 16 h. The reaction mixture was diluted with Et$_2$O and worked-up by addition of a saturated solution of aqueous NaHCO$_3$. The aqueous layer was extracted with Et$_2$O (2×10 mL) and the combined organic extract was washed with 10% aqueous potassium fluoride solution (2×10 mL), H$_2$O (1×10 mL) and saturated NaCl solution (1×10 mL), dried over anhydrous Na$_2$SO$_4$ and concentrated under reduced pressure on a rotary evaporator. Gradient flash column chromatography (98:2 to 95:5 hexane/EtOAc) gave, (R)-12h (83 mg, 42%) as a red oil. All other spectroscopic data of (R)-12h matched racemic 12h (vide supra).

Transmetalation-substitution of (R)-12h. The enantiomeric purity of (R)-12h was determined by conversion of the stannane to the aldehyde by transmetalation-DMF quench. A solution of (R)-12h (13 mg, 0.033 mmol) in THF (1 mL) at ±40° C. was treated with methyllithium (61 μL, 1.15 M in Et$_2$O, 0.053 mmol) and stirred for 1 h. Dimethylformamide (6 μL, 0.077 mmol) was added and the mixture was left to warm slowly to room temperature. The reaction mixture was diluted with Et$_2$O and worked-up by addition of a saturated solution of aqueous NaHCO$_3$. The aqueous layer was extracted with Et$_2$O (2×10 mL) and the combined organic extract was washed with 10% aqueous potassium fluoride solution (2×10 mL), H$_2$O (1×10 mL) and saturated NaCl solution (1×10 mL), dried over anhydrous Na$_2$SO$_4$ and concentrated under reduced pressure on a rotary evaporator. The mixture was filtered through a pad of silica gel, eluting with Et$_2$O to give (S)-12d (8 mg, 94%) as a red oil. $[\alpha]^{20}_D$ −41.9 (c 1.00, CHCl$_3$); CSP HPLC analysis (Chiralpak AS-H; eluent: 80:20 hexanes/i-PrOH, 1.0 mL/min) determined an enantiomeric ratio (er) of 91:9 (82% ee) [$t_R$(minor)=13.9 min, $t_R$(major)=29.2 min].

Example 13

Preparation of (R)-2-Iodo-1-dimethylaminoferrocene [(R)-12i)]

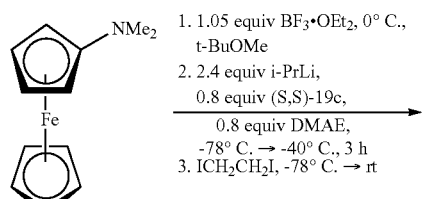

1. 1.05 equiv BF$_3$•OEt$_2$, 0° C., t-BuOMe
2. 2.4 equiv i-PrLi, 0.8 equiv (S,S)-19c, 0.8 equiv DMAE, −78° C. → −40° C., 3 h
3. ICH$_2$CH$_2$I, −78° C. → rt

11

-continued

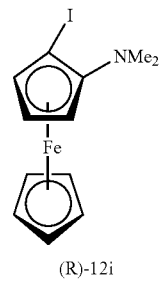

(R)-12i

A solution of (S,S)-19c (204 mg, 0.80 mmol) in t-BuOMe (5 mL) was cooled to −40° C., treated with i-PrLi (1.79 mL, 1.34 M, 2.40 mmol) and as solution of dimethylaminoethanol (DMAE, 71 mg, 0.80 mmol) in t-BuOMe (1 mL), and the mixture was stirred for 20 min. This solution was transferred by cannula to a mixture of 11.BF$_3$ at −78° C. [prepared by addition of BF$_3$.OEt$_2$ (0.13 mL, 1.05 mmol) to a solution of 11 (229 mg, 1.00 mmol) in t-BuOMe (8 mL) at 0° C. and stirring for 10 min]. After stirring for 10 min, the mixture was allowed to warm slowly to −40° C. over 2 h and then held at that temperature for an additional hour. After cooling back to −78° C., a solution of 1,2-diiodoethane (705 mg, 2.5 mmol) in t-BuOMe (5 mL) was added over 2 min and the mixture was allowed to warm to room temperature over 16 h. The reaction mixture was diluted with Et$_2$O and worked-up by addition of a saturated solution of aqueous NaHCO$_3$. The aqueous layer was extracted with Et$_2$O (2×10 mL) and the combined organic phase was washed with saturated sodium thiosulfate solution (2×10 mL), water (2×10 mL), brine (1×10 mL), dried over anhydrous Na$_2$SO$_4$ and concentrated under reduced pressure on a rotary evaporator. The reaction mixture was dissolved in 95:5 pentane/Et$_2$O and filtered through a pad of silica gel. Concentration of the filtrate in vacuo gave (R)-12i (168 mg, 47%); $[\alpha]^{20}_D$ −28.7 (c 1.00, CHCl$_3$); Spectroscopic data of (R)-12i matched racemic 121 (vide supra).

Enantiomeric purity assay of (R)-12i. The enantiomeric purity of (R)-12i was determined by conversion of the iodide to the acetate. A solution of (R)-12i (11 mg, 0.031 mmol) in absolute EtOH (0.5 mL) was treated with Cu(OAc)$_2$.H$_2$O (8 mg, 0.039 mmol) and heated at reflux for 10 min to give a dark mixture. After cooling to room temperature, the mixture was concentrated under reduced pressure. The residue was dissolved in Et$_2$O and filtered through a pipette of silica gel and the filtrate was concentrated to give (R)-14 (7 mg, 78%) as a yellow film; $[\alpha]^{20}_D$ +43.3 (c 0.82, CHCl$_3$); CSP HPLC analysis (Chiralcel OD-H; eluent: 95:5: hexanes/i-PrOH, 1.0 mL/min) determined an enantiomeric ratio (er) of 88:12 (76% ee) [$t_R$(minor)=8.4 min, $t_R$(major)=10.4 min]. All other spectroscopic data of (R)-14 matched racemic 14 (vide supra).

Example 14

Preparation of N,N,N",N"-Tetramethyl-2,2"-diamino-1,1"-biferrocene (13) from (12i)[21]

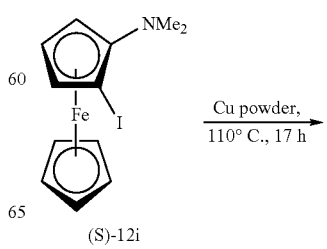

(S)-12i

Cu powder,
110° C., 17 h

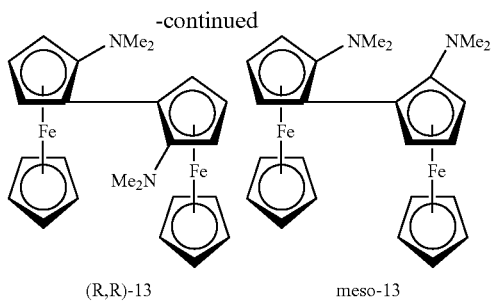

(R,R)-13  meso-13

A mixture of (S)-12i (96 mg, 0.27 mmol), dichloromethane (5 mL) and purified Cu powder (860 mg, 13.5 mmol) was concentrated to dryness under reduced pressure. The resulting solid mass was heated under argon at 110° C. for 17 h. After cooling to room temperature, the solid mass was taken up in dichloromethane (20 mL) and filtered through Celite in a sintered funnel. Concentration of the filtrate under reduced pressure and gradient column chromatography (neutral alumina, 99:1 to 95:5 hexanes/Et$_2$O) gave, sequentially, meso-13 (11 mg, 18%) as red-orange solid, and (R,R)-13 (35 mg, 56%) as a yellow-orange solid;

(R,R)-13: mp 115-116° C.; $[\alpha]_D^{20}$ −517 (c=1, CHCl$_3$). Two recrystallizations from isopropanol afforded (R,R)-13 with the following physical data: mp=143-145° C. (isopropanol); $[\alpha]_D^{20}$ −695 (c=1 CHCl$_3$). All other spectroscopic data of (R,R)-13 matched that of rac-13 (vide supra).

Example 15

Preparation of (R)-2-pyrrolidinyl-1-ferrocenecarboxaldehyde (R)-21

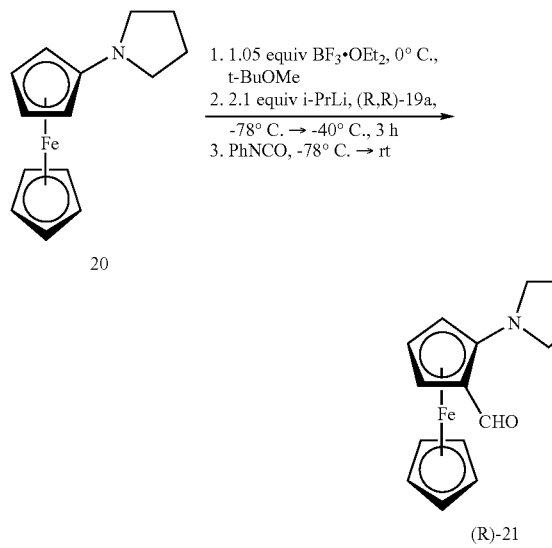

A solution of ligand (R,R)-19a (256 mg, 0.82 mmol) in t-BuOMe (2.5 mL) was cooled to −40° C., treated with i-PrLi (0.82 mL, 1.00 M, 0.82 mmol) and stirred for 20 min at that temperature. The solution was transferred by cannula to a mixture of 20.BF$_3$ at −78° C. [prepared by addition of BF$_3$.OEt$_2$ (52 μL, 0.41 mmol) to a solution of 20 (100 mg, 0.39 mmol) in t-BuOMe (4 mL) at 0° C. and stirring for 10 min]. After stirring for 10 min, the mixture was allowed to warm slowly to −40° C. over 2 h and then held at that temperature for an additional hour. After cooling back to −78° C., DMF (75 μL, 0.98 mmol) was added and the reaction mixture was allowed to warm to room temperature over 16 h. The reaction mixture was diluted with Et$_2$O and worked-up by addition of a saturated solution of aqueous NaHCO$_3$. The aqueous layer was extracted with Et$_2$O (1×10 mL) and the combined organic extract was washed with H$_2$O (1×10 mL), saturated NaCl solution (1×10 mL), dried over anhydrous Na$_2$SO$_4$ and concentrated under reduced pressure on a rotary evaporator. Flash column chromatography (silica gel 95:5 CH$_2$Cl$_2$/Et$_2$O. R$_f$=0.32) gave, aldehyde (R)-21 (43 mg, 39%) as a red oil that crystallized on standing; mp 78-80° C. (hexane); CSP HPLC analysis (Chiralpak AS-H; eluent: 80:20 hexanes/i-PrOH, 1.0 mL/min) determined an enantiomeric ratio (er) of 13:87 (74% ee) [t$_R$(major)=21.42 min, t$_R$(minor)=27.32 min]; IR (KBr) max 3442, 2956, 2875, 2823, 1648 cm$^{-1}$; $^1$H NMR (600 MHz, acetone-d$_6$) 10.23 (s, 1H), 4.59 (s, 1H), 4.37 (s, 1H), 4.28 (s, 6H), 3.26 (m, 2H) 3.16 (m, 2H), 1.99-1.96 (m, 4H); $^{13}$C NMR (150.9 MHz, acetone-d$_6$) 193.8, 115.7, 69.34, 69.29, 68.3, 65.9, 61.8, 53.5, 26.1; EIMS [m/z (%)] 283 (M+, 100), 145 (53); HRMS (EI) calcd for C$_{15}$H$_{17}$NO$^{56}$Fe: 283.0660. Found 283.0659.

Example 16

Preparation of (S)-[2-(Diphenylphosphinothioyl) ferrocenyl]-1-dimethylamine [(S)-23]

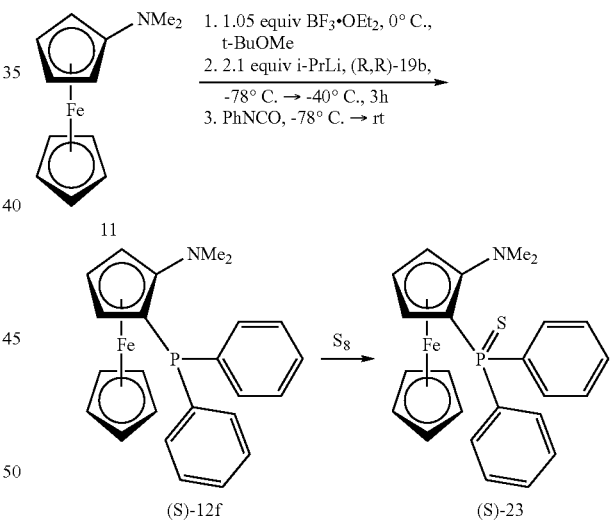

A solution of (R,R)-19b (390 mg, 1.38 mmol) in t-BuOMe (3 mL) was cooled to −40° C., treated sequentially with i-PrLi (2.23 mL, 1.85 M in pentane, 4.13 mmol) and dimethylaminoethanol (124 mg, 1.39 mmol) in t-BuOMe (3 mL), and stirred for 20 min at that temperature. The solution was transferred by cannula to a pre-formed mixture of 11.BF$_3$ at −78° C. [prepared by addition of BF$_3$.OEt$_2$ (175 μL, 1.39 mmol) to a solution of FcNMe$_2$ (300 mg, 1.31 mmol) in t-BuOMe (13 mL) at 0° C. and stirring for 10 min]. After stirring for 10 min at −78° C., the mixture was allowed to warm slowly to −40° C. over 2 h and then held at that temperature for an additional hour. After cooling back to −78° C., ClPPh$_2$ (600 μL, 3.27 mmol) was added and the mixture was allowed to warm slowly to room temperature. The reaction mixture was diluted with Et$_2$O and worked-up by addition of a saturated solution of aqueous NaHCO$_3$. The aqueous layer was extracted with Et$_2$O (3×15 mL) and the combined organic extract was washed with H$_2$O (1×15 mL), brine (1×15 mL), dried over anhydrous Na$_2$SO$_4$ and concentrated under reduced pressure on a rotary evaporator to afford the crude aminophosphine. To the crude mixture in a dry round bottom flask was added sulfur powder (1.59 g, 49.6 mmol) under argon. Toluene (25 mL) was added and the reaction mixture heated at 40° C. for 2 h. The reaction mixture was gravity filtered to remove excess sulfur and pre-adsorbed on silica gel. Flash column chromatography (90:10 pentane/diethyl ether) gave (S)-23 (285 mg, 50%) as an orange foam. $[\alpha]^{20}_D$ +55.2 (c 1.00, CHCl$_3$); CSP HPLC analysis (Chiralpak OD-H; eluent: 99:1 hexanes/i-PrOH, 1.0 mL/min) determined a 88.5:11.5 er (77% ee) [$t_R$(minor)=6.74 min, $t_R$(major)=7.23 min]; IR (KBr) $v_{max}$ 3394, 2950, 2788, 1494, 1419 cm$^{-1}$; $^{31}$P NMR (121.5 MHz, CDCl$_3$) 44.2 ppm; $^1$H NMR (300 MHz, CDCl$_3$) 8.00-7.88 (m, 2H), 7.79-7.71 (m, 2H), 7.48-7.36 (m, 6H), 4.33 (s, 5H), 4.29 (s, 1H), 4.13 (s, 1H), 3.81 (s, 1H), 2.50 (s, 6H) ppm; $^{13}$C NMR (75 MHz, CDCl$_3$) 135.4 (d, J=87.5 Hz), 133.5 (d, J=86.8 Hz), 132.6 (d, J=10.6 Hz), 131.8 (d, J=10.6 Hz), 131.1 (d, J=2.3 Hz), 130.8 (d, J=2.3 Hz), 127.9 (d, J=12.8 Hz), 117.2 (d, J=9.1 Hz), 72.3 (d, J=13.6 Hz), 69.9, 67.1 (d, J=92.8 Hz), 65.3 (d, J=11.3 Hz), 61.8 (d, J=8.3 Hz), 46.0 ppm; EIMS [m/z (%)] 445 (M$^+$, 100), 413 (32); HRMS (EI) calcd for C$_{24}$H$_{24}$NP$^{56}$Fe: 445.07161. Found 445.07158. Anal. Calcd for C$_{24}$H$_{24}$NPSFe: C, 64.73; H, 5.43. Found: C, 64.79; H, 5.44.

Example 17

(S)-[2-(Diphenylphosphinothioyl)ferrocenyl]-1-dimethylammonium tetrafluoroborate [(S)-24]

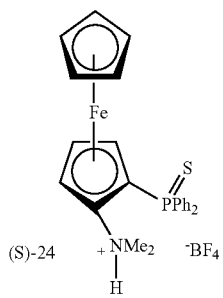

A solution of aminophosphine sulfide (S)-23 (131 mg, 294 mmol) in diethyl ether (13 mL) at 0° C. was treated with tetrafluoroboric acid-diethyl ether complex (50 μL, 367 mmol). An immediate change in color from orange to yellow was observed, and a yellow powder precipitated out of solution. The solid was collected by suction filtration, washed with cold Et$_2$O, and dried in vacuo to afford ammonium salt (S)-24 as a yellow powder (155 mg, 99%); $[\alpha]^{20}_D$ -76.1 (c 0.52, CHCl$_3$); IR (KBr) $v_{max}$ 3449, 3369, 3051, 2923, 1436, 1100, 1053, 751, 714 cm$^{-1}$; $^{31}$P NMR (121.5 MHz, CDCl$_3$) 37.7 ppm; $^1$H NMR (300 MHz, CDCl$_3$) 11.03 (s, 1H), 7.94-7.87 (m, 2H), 7.68-7.55 (m, 6H), 7.52-7.50 (m, 2H), 5.52 (s, 1H), 4.73 (s, 6H), 4.31 (s, 6H), 3.63 (d, 3H, J=5.4 Hz), 2.90 (d, 3H, J=5.1 Hz) ppm; FABMS [m/z (%)] 446 (M$^+$, 100), 229 (87) HRMS (FAB) calcd for C$_{24}$H$_{25}$NPS$^{56}$Fe: 446.0795. Found 446.0794. Recrystallization via vapor-liquid diffusion of Et$_2$O into a solution of (S)-24 in CH$_2$Cl$_2$ rendered the salt enentiomerically pure in 98% ee after two recrystallizations (vide infra); mp>225° C. (decomp); $[\alpha]^{20}_D$ -83.1 (c 0.52, CHCl$_3$);

Enantiomeric purity assay of (S)-24. A biphasic suspension of salt (S)-24 in sat. aqueous NaHCO$_3$ and diethyl ether was gently stirred until all the solid dissolved. The layers were separated and the aqueous phase was washed one more time with diethyl ether. The combined ethereal layer was washed with water, brine, dried over anhydrous Na$_2$SO$_4$, filtered and concentrated in vacuo to give (S)-23 in quantitative yield; $[\alpha]^{20}_D$ +39.6 (c 1.00, CHCl$_3$); CSP HPLC analysis of (S)-23 (mp 118-122° C.) Chiralpak OD-H; eluent: 99:1 hexanes/i-PrOH, 1.0 mL/min determined a 99:1 er (98% ee) [$t_R$(minor) 6.68 min, $t_R$(major) 7.47 min].

Determination of absolute stereochemistry by X-Ray diffraction analysis of salt (S)-24. Because the asymmetric synthesis of 12c, d, f, h, and i must involve an asymmetric deprotonation step, all products prepared with a specific enantiomerically pure diamine additive [(R,R)- or (S,S)-19a, b,c] during lithiation will have the same relative stereochemistry after electrophile quench. To determine whether the prochiral R or S proton was preferentially abstracted in 11 when (R,R)-19b was used as the chiral diamine for lithiation with i-PrLi, an X-ray diffraction study was performed on an orange block-shaped crystal of (S)-24 (0.33×0.23×0.21 mm$^3$), which was obtained by crystallization from CH$_2$Cl$_2$ by vapor diffusion with diethyl ether. The salient data for this crystal structure are as follows: C$_{24}$H$_{25}$BF$_4$ FeNPS: M=533.14 g/mol, orthorhombic, P2$_1$2$_1$2$_1$, a=10.3605(13) Å, b=12.6260(16) Å, c=17.967(2) Å, V=2350.3(5) Å$^3$, α=β=γ=90°, Z=4, D$_c$=1.507 g/cm$^3$, F(000)=1096, T=100(2) K. Data were collected on a Bruker APEX CCD system with graphite monochromated Mo Kα radiation (λ=0.71073 Å); 35112 data were collected. The structure was solved by Direct Methods (SHELXTL) and refined by full-matrix least squares on F$^2$ resulting in final R, R$_W$ and GOF [for 6435 data with F>2σ(F)] of 0.0238, 0.0578 and 1.02, respectively, for solution using the S enantiomer model [Flack parameter=0.000(7)]. The xray crystalgraph is shown in FIG. 1 and is an ORTEP plot of (S)-24. Thermal ellipsoids shown at the 50% probability level. All hydrogen atoms except H1a are omitted for clarity.

Based on this result, the pro-R-proton in 11 is lithitated preferentially when the reaction is mediated by (R,R)-19a and (R,R)-19b, while (S,S)-19c results in pro-S-lithiation of 11, as summarized in Table 2 and Table 3.

Example 18

Desulfurization to (S)-2-Diphenylphosphino-1-dimethylaminoferrocene ((S)-12f)

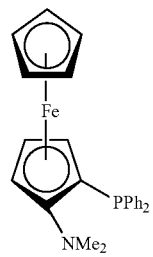

Ni—Al catalyst (1.73 g) was activated by portion-wise addition of 6 M NaOH solution (25 mL) and heating at 50° C.

for 1 h. The catalyst was washed with H$_2$O (7×25 mL), MeOH (3×25 mL), Et$_2$O (2×25 mL) and acetonitrile (2×25 mL). A solution of aminophosphine sulfide (S)-23 (185 mg, 98% ee) in acetonitrile (10 mL) was added to a stirred suspension of the catalyst in acetonitrile (10 mL) under argon, and the mixture was heated to 60° C. for 75 min. The reaction mixture was allowed to cool to room temperature and filtered through a pad of Celite, washing with acetonitrile. The filtrate was evaporated to dryness on a rotary evaporator, re-dissolved in Et$_2$O and filtered through a pad of silica gel, eluting with additional Et$_2$O. Removal of the solvent in vacuo afforded the free aminophosphine (S)-12f (145 mg, 84%) as an orange semisolid that had spectroscopic data in accord with the racemate; $[\alpha]^{20}_D$ −242 (c 1.00, CHCl$_3$).

Example 19(a)

(S)-2-Diphenylphosphino-1-dimethylaminoferrocene iridium (COD) BAr$_F$ [(S)-32]

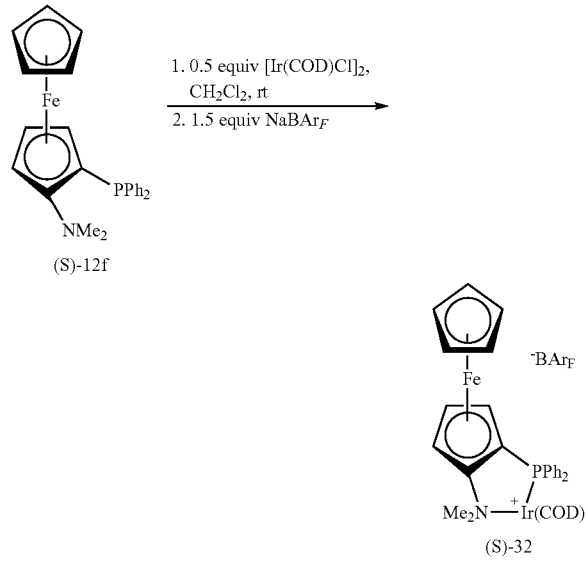

A mixture of ligand (S)-12f (96 mg, 0.23 mmol) and [Ir(COD)Cl]$_2$ (78 mg, 0.12 mmol) in CH$_2$Cl$_2$ (5 mL) was stirred under argon at reflux for 2 h. Sodium tetrakis(3,5-bis(trifluoromethyl)phenyl)borate (NaBAr$_F$, 310 mg, 0.35 mmol) and water (5 mL) were then added, at which time the color changed from orange to red. The solution was allowed to stir for 15 minutes after which the layers were separated. The aqueous layer was washed with CH$_2$Cl$_2$ (3×5 mL) and the combined organic phase was washed with water. The solution was concentrated almost to dryness on a rotary evaporator and then passed through a plug of silica gel, eluting with additional CH$_2$Cl$_2$. Removal of the solvent in vacuo afforded (S)-32 as orange flakes (360 mg, 98%). mp: 168-172° C.; $[\alpha]^{20}_D$ −1.39 (c 1.01, CHCl$_3$); IR (KBr): $v_{max}$ 2958, 2925, 2891, 1610, 1439, 1356, 1279, 1169, 1126 cm$^{-1}$; $^{31}$P NMR (121.5 MHz, CDCl$_3$) 14.95 ppm; $^{19}$F NMR (282.4 MHz, CDCl$_3$): 62.34 pp; $^1$H NMR (300 MHz, CDCl$_3$) 7.72 (m, 10H), 7.55-7.42 (m, 12H), 5.04 (m, 1H), 4.90 (t 1H, J=2.7 Hz), 4.56 (m, 1H), 4.41 (m, 1H), 4.31 (m, 1H), 4.08 (s, 5H), 4.05 (m, 1H), 3.51 (m, 1H), 3.13 (s, 3H), 2.69 (s, 3H), 2.39-2.24 (m, 4H), 2.05 (m, 1H), 1.90 (d, 2H, J=9.3 Hz), 1.75 (m, 1H) ppm; $^{13}$C NMR (75.5 MHz, CDCl$_3$) 161.9 (q, $J^{13}_{C\text{-}^{31}B}$=49.8 Hz), 135.0, 133.1, 132.7 (d, $J^{13}_{C\text{-}^{31}P}$=11.3 Hz), 132.4, 132.3 (d, J=2.3 Hz), 131.9 (d, J=1.5 Hz), 130.1, 129.8 (d, $J^{13}_{C\text{-}^{31}P}$=11.3 Hz), 129.5 (d, $J^{13}_{C\text{-}^{31}P}$=10.6 Hz), 129.0 (q, $J^{13}_{C\text{-}^{19}F}$=29.4 Hz), 127.2, 124.7 (q, $J^{13}_{C\text{-}^{19}F}$=272.4 Hz), 124.3 (d, $J^{13}_{C\text{-}^{31}P}$=22.7 Hz), 117.6, 92.9, 92.7, 91.5, 91.3, 74.8 (d, $J^{13}_{C\text{-}^{31}P}$=6.0 Hz), 72.2, 70.4 (d, $J^{13}_{C\text{-}^{31}P}$=57.4 Hz), 65.7, 61.0, 60.7, 58.6, 58.5, 57.8, 50.7, 32.44, 32.40, 29.7, 29.54, 29.51 ppm; FABMS (m/z, (%)): 712 (M-BAr$_F$, (100)). HRMS (FAB; m/z): calcd for C$_{32}$H$_{34}$NPFeIr 712.1402. Found 712.1407. Anal. calcd for C$_{64}$H$_{48}$BF$_{24}$FeNPIr: C, 48.75; H, 3.07. Found C, 48.79; H, 2.98.

Example 19(b)

2-Diphenylphosphino-1-dimethylaminoferrocene palladium dichloride

Figure 2:
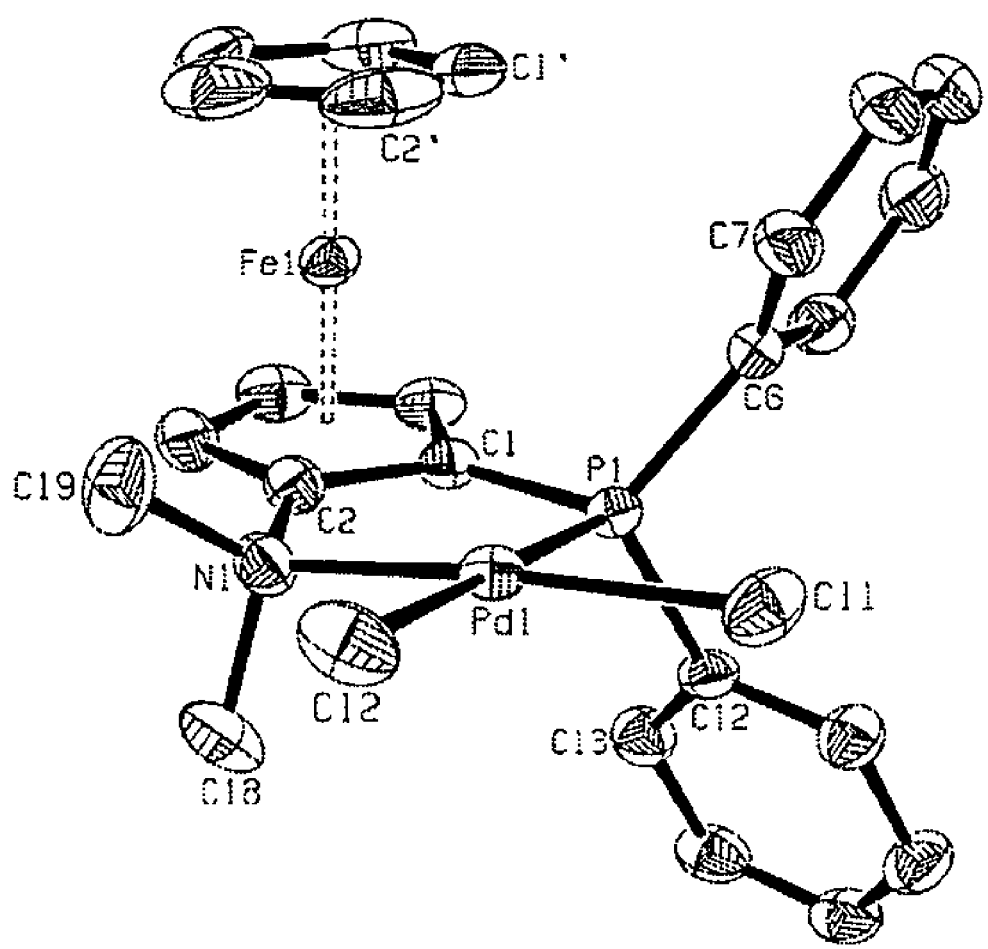
FIG. 2 is an ORTEP plot of 2-diphenylphosphino-1-dimethylaminoferrocene palladium dichloride with all hydrogen atoms omitted for clarity.

Representative Procedure: A solution of aminophosphine 12f (94 mg, 0.30 mmol) and Pd(MeCN)$_2$Cl$_2$ (58 mg, 0.30 mmol) in CH$_2$Cl$_2$ (2 mL) was stirred at room temperature in a dry flask under argon until TLC indicated consumption of the aminophosphine (75 min). The reaction mixture was then filtered through a pad of silica gel, eluting with 97:3 CH$_2$Cl$_2$/MeOH, and concentrated. Recrystallization from acetonitrile at −20° C. gave the product (154 mg, 87%) as a light orange powder in two crops. mp>225° C. (decomp. at 210° C.); IR (KBr): $v_{max}$ 3448, 1460, 1434 cm$^{-1}$; $^{31}$P NMR (243 MHz, CDCl$_3$): δ 25.3; $^1$H NMR (600 MHz, CDCl$_3$): δ 8.11-8.05 (m, 2H), 7.63-7.58 (m, 1H), 7.58-7.52 (m, 4H), 7.51-7.46 (m, 1H), 7.39-7.34 (m, 2H), 4.74 (t, 1H J=2.3 Hz), 4.53 (s, 1H), 4.21 (s, 1H), 4.00 (s, 5H), 3.46 (s, 3H), 3.09 (s, 3H); $^{13}$C NMR (150 MHz, CDCl$_3$) δ 134.6 (d, $J^{13}_{C\text{-}^{31}P}$=11.6 Hz), 132.2 (d, $J^{13}_{C\text{-}^{31}P}$=2.2 Hz), 131.8 (d, $J^{13}_{C\text{-}^{31}P}$=10.1 Hz), 131.4 (d, $J^{13}_{C\text{-}^{31}P}$=57.8 Hz), 131.4 (d, $J^{13}_{C\text{-}^{31}P}$=3.1 Hz), 129.4 (d, $J^{13}_{C\text{-}^{31}P}$=67.7 Hz), 128.9 (d, $J^{13}_{C\text{-}^{31}P}$=11.6 Hz), 128.6 (d, $J^{13}_{C\text{-}^{31}P}$=12.1 Hz), 126.9 (d, $J^{13}_{C\text{-}^{31}P}$=24.6 Hz), 75.2 (d, $J^{13}_{C\text{-}^{31}P}$=6.1 Hz), 72.8 (d, $J^{13}_{C\text{-}^{31}P}$=56.1 Hz), 63.9, 60.3 (d, $J^{13}_{C\text{-}^{31}P}$=12.3 Hz), 58.2, 54.5. FABMS (m/z (%)): 591 (M$^+$, 14), 554 (90), 518 (84), 413 (77), 292 (73), 229 (85), 214 (81), 108 (100). Anal. calcd for C$_{24}$H$_{24}$NPCl$_2$FePd: C, 48.81; H, 4.10. Found: C, 49.04; H, 4.09. An x-ray crystalgraph is shown in FIG. 2.

Example 19(c)

2-Dicyclohexylphosphino-1-dimethylaminoferrocene palladium dichloride

Prepared on a 0.22 mmol scale in a manner analogous to Example 19b to give the product (121 mg, 91%) as rust-colored crystals after recrystallization from acetonitrile at −20° C. mp>225° C. (decomp. at 195° C.); IR (KBr): $v_{max}$ 2931, 2850, 1446 cm$^{-1}$; $^{31}$P NMR (121.5 MHz, CDCl$_3$): δ 51.1; $^1$H NMR (300 MHz, CDCl$_3$): δ 4.71 (s, 1H), 4.59 (s, 1H), 4.46 (s, 5H), 4.00 (s, 1H), 3.47 (s, 3H), 3.12 (s, 3H), 2.72-2.54 (m, 1H), 2.52-2.33 (m, 1H), 2.33-2.16 (m, 2H), 2.16-1.88 (m, 5H), 1.87-1.31 (m, 10H), 1.31-1.05 (m, 3H); $^{13}$C NMR (75.5 MHz, CDCl$_3$): δ 128.0 (d, $J^{13}_{C\text{-}^{31}P}$=20.9 Hz), 74.6 (d, $J^{13}_{C\text{-}^{31}P}$=5.6 Hz), 73.8, 73.3, 63.1, 60.4 (d, $J^{13}_{C\text{-}^{31}P}$=10.6 Hz), 58.5, 56.7, 37.7 (d, $J^{13}_{C\text{-}^{31}P}$=30.2 Hz), 35.1 (d, $J^{13}_{C\text{-}^{31}P}$=30.2 Hz), 29.0 (d, $J^{13}_{C\text{-}^{31}P}$=2.0 Hz), 28.7, 28.1, 28.0, 26.9 (d, $J^{13}_{C\text{-}^{31}P}$=2.0 Hz), 26.7, 26.6 (d, $J^{13}_{C\text{-}^{31}P}$=2.9 Hz), 26.5, 26.4, 25.8, 25.4; FABMS (m/z (%)): 603 (M$^+$, 8), 566 (81), 229 (100); Anal. calcd for C$_{24}$H$_{36}$NPCl$_2$FePd: C, 47.83; H, 6.02. Found: C, 47.77; H, 6.20.

Example 19(d)

2-Diphenylphosphino-1-dimethylaminoferrocene platinum dichloride

Figure 3:
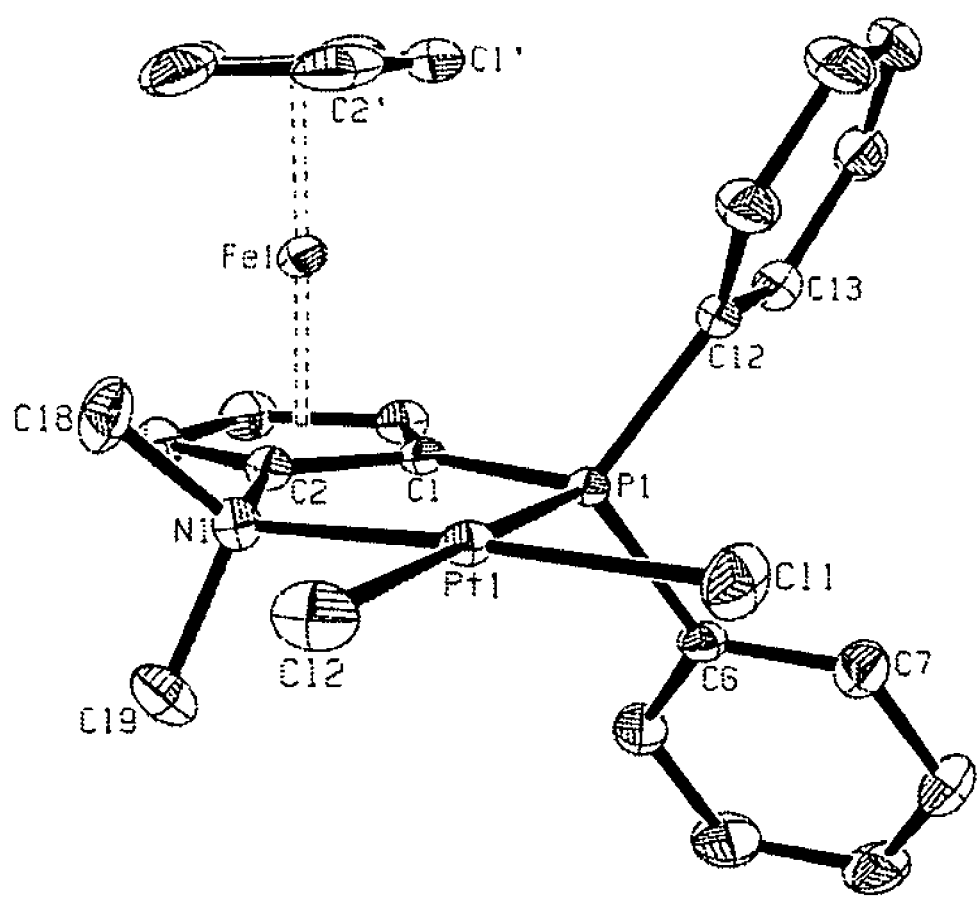
FIG. 3 is an ORTEP plot of 2-diphenylphosphino-1-dimethylaminoferrocene platinum dichloride with all hydrogen atoms omitted for clarity.

Representative procedure. A suspension of aminophosphine 12f (100 mg, 0.24 mmol) and Pt(COD)Cl$_2$ (90 mg, 0.24 mmol) in PhMe (2.5 mL) was heated at reflux until TLC indicated consumption of the aminophosphine (1.5 h). The solvent was removed on a rotary evaporator, the residue redissolved in CH$_2$Cl$_2$, filtered through a pad of silica gel eluting with 97:3 CH$_2$Cl$_2$/MeOH, and concentrated again under reduced pressure. Recrystallization from acetone at −20° C. gave the product (82 mg, 50%) as fine orange crystals. mp>225° C. (decomp. at 210° C.); IR (KBr): $v_{max}$ 3469, 3421, 3048, 2925, 1435 cm$^{-1}$; $^{31}$P NMR (243 MHz, CDCl$_3$): δ 2.01 (t, $J^{31}{}_{P\text{-}}{}^{195}{}_{Pt}$=1982 Hz); $^1$H NMR (300 MHz, CDCl$_3$): δ 8.18-8.06 (m, 2H), 7.63-7.40 (m, 6H), 7.39-7.30 (m, 2H), 4.92 (t, 1H, J=2.6 Hz), 4.53 (s, 1H), 4.29 (t, 1H, J=1.0 Hz), 3.94 (s, 5H), 3.65 (t, 3H, J=16.6 Hz), 3.24 (t, 3H, J=15.1 Hz); $^1$H NMR (600 MHz, acetone-d$_6$): δ 8.24-8.17 (m, 2H), 7.70-7.60 (m, 3H), 7.59-7.53 (m, 2H), 7.53-7.48 (m, 1H), 7.45-7.39 (m, 2H), 5.08 (t, 1H, J=2.3 Hz), 4.94 (s, 1H), 4.62 (t, 1H, J=1.1 Hz), 4.01 (s, 5H), 3.66 (s, 3H), 3.22 (s, 3H); $^{13}$C NMR (150 MHz, CDCl$_3$) δ 134.5 (d, $J^{13}{}_{C\text{-}}{}^{31}{}_{P}$=11.9 Hz), 132.1 (d, $J^{13}{}_{C\text{-}}{}^{31}{}_{P}$=2.2 Hz), 131.5 (d, $J^{13}{}_{C\text{-}}{}^{31}{}_{P}$=10.3 Hz), 131.1 (d, $J^{13}{}_{C\text{-}}{}^{31}{}_{P}$=68.8 Hz), 130.9 (d, $J^{13}{}_{C\text{-}}{}^{31}{}_{P}$=2.7 Hz), 129.1 (d, $J^{13}{}_{C\text{-}}{}^{31}{}_{P}$=21.6 Hz), 128.9 (d, $J^{13}{}_{C\text{-}}{}^{31}{}_{P}$=73.8 Hz), 128.8 (d, $J^{13}{}_{C\text{-}}{}^{31}{}_{P}$=11.4 Hz), 128.6 (d, $J^{13}{}_{C\text{-}}{}^{31}{}_{P}$=12.3 Hz), 74.9 (d, $J^{13}{}_{C\text{-}}{}^{31}{}_{P}$=6.4 Hz), 74.0 (d, $J^{13}{}_{C\text{-}}{}^{31}{}_{P}$=66.7 Hz), 63.2, 59.7, 59.4 (d, $J^{13}{}_{C\text{-}}{}^{31}{}_{P}$=10.6 Hz), 55.6; FABMS (m/z (%)): 679 (M$^+$, 6), 643 (100), 605 (30), 486 (22); Anal. calcd for C$_{24}$H$_{24}$NPCl$_2$FePt: C, 42.44; H, 3.56. Found: C, 42.67; H, 3.56. An x-ray crystalgraph is shown in FIG. 3.

Example 19(e)

2-Dicyclohexylphosphino-1-dimethylaminoferrocene platinum dichloride

Prepared on a 0.19 mmol scale in a manner analogous to Example 19d to give the product (101 mg, 79%) as orange crystals after recrystallization from CH$_2$Cl$_2$/EtOAc at −20° C. mp>225° C. (decomp. at 210° C.); IR (KBr): $v_{max}$ 3448, 1460, 1434 cm$^{-1}$; $^{31}$P NMR (121 MHz, CDCl$_3$): δ 21.7 (t, $J^{31}{}_{P}{}^{195}{}_{Pt}$=1898 Hz); $^1$H NMR (600 MHz, CDCl$_3$): δ 4.86 (t, 1H, J=2.5 Hz), 4.57 (s, 1H), 4.46 (s, 5H), 4.00 (s, 1H), 3.65 (t, 3H, J=14.8 Hz), 3.26 (t, 3H, J=14.3 Hz), 2.77-2.61 (m, 1H), 2.57-2.39 (m, 1H), 2.31-2.17 (m, 1H), 2.14-1.75 (m, 8H), 1.74-1.53 (m, 4H), 1.50-1.30 (m, 3H), 1.30-1.05 (m, 4H); $^{13}$C NMR (150 MHz, CDCl$_3$) δ 129.9 (d, $J^{13}{}_{C\text{-}}{}^{31}{}_{P}$=17.8 Hz), 74.5 (d, $J^{13}{}_{C\text{-}}{}^{31}{}_{P}$=52.6 Hz), 74.3 (d, $J^{13}{}_{C\text{-}}{}^{31}{}_{P}$=4.8 Hz), 71.5, 62.44, 59.4, 59.2 (d, $J^{13}{}_{C\text{-}}{}^{31}{}_{P}$=8.9 Hz), 58.0, 36.1 (d, $J^{13}{}_{C\text{-}}{}^{31}{}_{P}$=36.9 Hz), 33.0 (d, $J^{13}{}_{C\text{-}}{}^{31}{}_{P}$=37.6 Hz), 28.9, 28.0, 27.6 (d, $J^{13}{}_{C\text{-}}{}^{31}{}_{P}$=4.4 Hz), 27.0 (d, $J^{13}{}_{C\text{-}}{}^{31}{}_{P}$=11.6 Hz), 26.8 (d, $J^{13}{}_{C\text{-}}{}^{31}{}_{P}$=8.0 Hz), 26.6 (d, $J^{13}{}_{C\text{-}}{}^{31}{}_{P}$=6.1 Hz), 26.5 (d, $J^{13}{}_{C\text{-}}{}^{31}{}_{P}$=11.9 Hz), 26.1, 25.5; FABMS (m/z (%)): 691 (M$^+$, 8), 655 (100), 616 (59), 55 (76). Anal. calcd for C$_{24}$H$_{24}$NPCl$_2$FePd: C, 48.81; H, 4.10. Found: C, 49.04; H, 4.09.

Example 20

General Procedure for Hydrogenation of Olefins 33-38

A solution of olefin substrate (~0.15-0.3 mmol) and iridium catalyst (S)-32 or rac-32 (2 mol %) in dry CH$_2$Cl$_2$ (0.1 M) in a capped with a venting needle was sealed in a Parr bomb. The bomb was evacuated and back-filled with H$_2$ (×3), pressurized to 62 bar of H$_2$ and placed on a magnetic stirrer. The reaction mixture was stirred for 72 h at room temperature, after which the pressure was released. The solvent was removed in vacuo and the crude mixture was passed through a plug of silica gel eluting with 9:1 hexane/EtOAc to remove catalyst residue. The solvent was removed in vacuo to yield the saturated product. Products obtained in this manner were sufficiently pure as determined by melting point and/or spectroscopic analysis. Enantiomeric excesses were determined using CSP HPLC or GC for reactions using (S)-32.

Example 20(a)

(−)-1,2-Diphenylpropane (33)

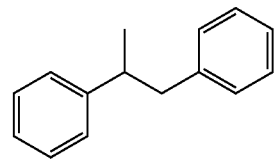

33

According to the general procedure, a solution of methyl stilbene (57 mg, 0.29 mmol) and iridium catalyst (S)-32 (9.4 mg, 0.0060 mmol, 2.0 mol %) in CH$_2$Cl$_2$ (3 mL) was hydrogenated. Removal of the solvent in vacuo and standard purification gave 33 (54 mg, 94%) as a colorless oil; $[\alpha]^{20}{}_D$ −55.2 (c 1.00, CHCl$_3$); Chiral GC analysis (Chirasil DEX-CB; program: 100° C. for 5 min, the 0.5° C./min to 140° C. for 5 min, then 2° C./min to 180° C. for 10 min) determined a 86:14 er (72% ee) [t$_R$(minor) 66.26 min, t$_R$(major) 66.66 min]; $^1$H NMR (300 MHz, CDCl$_3$) 7.37-7.30 (m, 3H), 7.24-7.20 (m, 2H), 7.14 (d, 2H, J=7.2 Hz), 3.13-2.98 (m, 2H), 2.82 (q, 1H, J=7.8 Hz), 1.31 (d, 3H, J=6.6 Hz) ppm; $^{13}$C NMR (75 MHz, CDCl$_3$) 147.0, 140.8, 129.1, 128.3, 128.1, 127.0, 126.0, 125.8, 45.0, 41.8, 21.1 ppm.

Example 20(b)

(−)-Ethyl 3-phenylbutanoate (34)

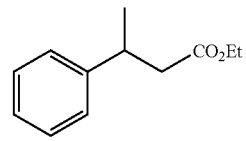

34

According to the general procedure, a solution of ethyl 3-phenylbut-2-enoate (57 mg, 0.29 mmol) and iridium catalyst (S)-32 (9.4 mg, 0.0060 mmol, 2 mol %) in CH$_2$Cl$_2$ (3 mL) was hydrogenated. Removal of the solvent in vacuo and standard purification gave 34 (54 mg, 94%) as a colorless oil. $[\alpha]^{20}{}_D$ −55.2 (c 1.00, CHCl$_3$); CSP HPLC analysis (Chiralcel OB-H; eluent: 99.5:0.5 hexanes/i-PrOH, 0.5 mL/min) determined a 95:5 er (90% ee) [t$_R$(major) 11.99 min, t$_R$(minor) 14.09 min]; $^1$H NMR (300 MHz, CDCl$_3$) 7.33-7.17 (m, 5H), 4.08 (q, 2H, J=6.9 Hz), 3.35-3.23 (sextet, 1H, J=7.2 Hz), 2.66-2.50 (m, 2H), 1.31 (d, 3H, J=6.9 Hz), 1.19 (t, 3H, J=6.9 Hz) ppm; $^{13}$C NMR (75 MHz, CDCl$_3$) 172.4, 145.7, 128.4, 126.7, 126.3, 60.2, 43.0, 36.5, 21.8, 14.1 ppm.

Example 20(c)

(−)-Ethyl 3-(4-methoxyphenyl)butanoate (35)

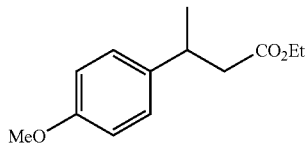

According to the general procedure, a solution of ethyl 3-(4-methoxyphenyl)but-2-enoate (58 mg, 0.26 mmol) and iridium catalyst (S)-32 (8.4 mg, 0.0053 mmol, 2 mol %) in CH$_2$Cl$_2$ (3 mL) was hydrogenated. Removal of the solvent in vacuo and standard purification gave 35 (58 mg, 99%) as a colorless oil; $[\alpha]^{20}_D$ −26.7 (c 1.00, CHCl$_3$); CSP HPLC analysis (Chiralcel OB-H; eluent: 99.5:0.5 hexanes/i-PrOH, 0.5 mL/min) determined a 96:4 er (92% ee) [$t_R$(major) 21.73 min, $t_R$(minor) 28.91 min]; $^1$H NMR (300 MHz, CDCl$_3$) 7.14 (d, 2H, J=8.4 Hz), 6.84 (d, 2H, J=8.7 Hz), 4.07 (q, 2H, J=6.9 Hz), 3.78 (s, 3H), 3.24 (sextet, 1H, J=7.2 Hz), 2.61-2.46 (m, 2H), 1.27 (d, 3H, J=6.9 Hz), 1.18 (t, 3H, J=7.2 Hz) ppm; $^{13}$C NMR (75 MHz, CDCl$_3$) 172.4, 158.0, 137.8, 131.4, 127.6, 113.8, 60.1, 55.1, 43.2, 35.7, 21.9, 14.1 ppm.

Example 20(d)

(+)-Ethyl 2-methyl-3-phenylpropanoate (36)

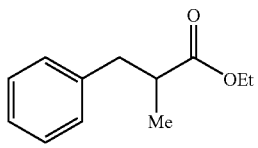

According to the general procedure, a solution of ethyl 2-methyl-3-phenylacrylate (34 mg, 0.18 mmol) and iridium catalyst (S)-32 (5.7 mg, 0.0036 mmol, 2.0 mol %) in CH$_2$Cl$_2$ (1.8 mL) was hydrogenated. Removal of the solvent in vacuo and standard purification gave 36 (30 mg, 88%) as a colorless oil. $[\alpha]^{20}_D$ +28.4 (c 1.0, CHCl$_3$); CSP HPLC analysis (Chiralcel OB-H; eluent: 99.5:0.5 hexanes/i-PrOH, 0.5 mL/min) determined a 91:9 er (82% ee) [$t_R$(minor) 8.52 min, $t_R$(major) 10.10 min]; $^1$H NMR (300 MHz, CDCl$_3$) 7.31-7.16 (m, 5H), 4.09 (q, 2H, J=6.9 Hz), 3.08-2.98 (m, 1H), 2.79-2.64 (m, 2H), 1.21 (d, 3H, J=7.2 Hz), 1.16 (d, 3H, J=6.3 Hz) ppm; $^{13}$C NMR (75 MHz, CDCl$_3$) 176.1, 139.4, 128.9, 128.3, 126.2, 60.2, 41.4, 39.7, 16.7, 14.1 ppm.

Example 20(e)

(+Ethyl 3-(4-methoxyphenyl)-2-methylpropanoate (37)

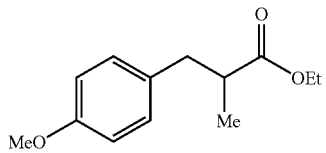

According to the general procedure, a solution of ethyl 3-(4-methoxyphenyl)-2-methylacrylate (30 mg, 0.14 mmol) and iridium catalyst (S)-32 (4.5 mg, 0.0029 mmol, 2.0 mol %) in CH$_2$Cl$_2$ (1.4 mL) was hydrogenated. Removal of the solvent in vacuo and standard purification gave 37 (30 mg, 96%) as a colorless oil. $[\alpha]^{20}_D$ +24.5 (c 1.25, CHCl$_3$); CSP HPLC analysis (Chiralcel OB-H; eluent: 99.5:0.5 hexanes/i-PrOH, 0.5 mL/min) determined a 90:10 er (80% ee) [$t_R$(minor) 9.01 min, $t_R$(major) 9.76 min]; $^1$H NMR (300 MHz, CDCl$_3$) 7.08 (d, 2H, J=8.7 Hz), 6.81 (d, 2H, J=8.7 Hz), 4.09 (q, 2H, J=7.2 Hz), 3.78 (s, 3H), 3.01-2.90 (m 1H), 2.73-2.57 (m, 2H), 1.19 (t, 3H, J=7.2 Hz), 1.13 (d, 3H, J=6.6 Hz) ppm; $^{13}$C NMR (75 MHz, CDCl$_3$) 176.2, 158.1, 131.4, 129.9, 113.7, 60.2, 55.2, 41.7, 38.8, 16.7, 14.2 ppm.

Example 20(f)

(−)-Ethyl 3-(naphthalen-2-yl)-butanoate (38)

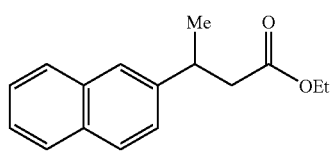

According to the general procedure, a solution of ethyl 3-(naphthalen-2-yl)-but-2-enoate) (70 mg, 0.29 mmol) and iridium catalyst (S)-32 (9.2 mg, 0.0058 mmol, 2.0 mol %) in CH$_2$Cl$_2$ (3 mL) was hydrogenated. Removal of the solvent in vacuo and standard purification gave 38 (70 mg, 99%) as a colorless oil. $[\alpha]^{20}_D$ −25.9 (c 1.02, CHCl$_3$); CSP HPLC analysis (Chiralcel OD-H; eluent: 99.5:0.5 hexanes/i-PrOH, 1.0 ml/min) determined a 89.5:10.5 er (79% ee) [$t_R$(minor) 12.34 min, $t_R$(major) 14.19 min]; $^1$H NMR (300 MHz, CDCl$_3$) 7.82 (d, 3H, J=8.4 Hz), 7.69 (s, 1H), 7.51-7.39 (m, 3H), 4.11 (q, 2H, J=7.2 Hz), 3.50 (sextet, 1H, J=7.5 Hz), 2.81-2.62 (m, 2H), 1.42 (d, 3H, J=6.9 Hz), 1.19 (t, 3H, J=7.2 Hz) ppm; $^{13}$C NMR (75 MHz, CDCl$_3$) 172.3, 143.1, 135.5, 132.3, 128.1, 127.6, 127.5, 125.9, 125.4, 125.3, 124.9, 60.2, 42.8, 42.6, 36.6, 21.7, 14.1 ppm.

Example 20(g)

1,2-Diphenylethane (39)

According to the general procedure, a solution of trans-stilbene (50 mg, 0.28 mmol) and rac-32 (8.8 mg, 0.0056 mmol, 2.0 mol %) in CH$_2$Cl$_2$ (3 mL) was pressurized with H$_2$ to 62 bar and stirred for 48 h. Filtration of the reaction mixture and evaporation of the solvent gave 39 (50 mg, 97%). mp 48-50° C. (lit.[1] 47-49° C.) $^1$H NMR (300 MHz, CDCl$_3$): δ 7.39-7.25 (m, 10H), 3.01 (s, 4H); $^{13}$C NMR (75.5 MHz, CDCl$_3$): δ 141.9, 128.6, 128.5, 126.0, 38.1.

Example 20(h)

Methyl 3-phenylpropanoate (40)

According to the general procedure, a solution of methyl trans cinnamate (49 mg, 0.30 mmol) and rac-32 (9.8 mg, 0.0062 mmol, 2.0 mol %) in CH$_2$Cl$_2$ (3 mL) was pressurized with H$_2$ to 62 bar and stirred for 48 h. Filtration of the reaction mixture and evaporation of the solvent gave 40 as a clear oil (48 mg, 95%). $^1$H NMR$^{26}$ (300 MHz, CDCl$_3$): δ 7.33-7.19 (m, 5H), 3.68 (s, 3H), 2.97 (t, 2H, J=8.1 Hz), 2.65 (t, 2H, J=7.8 Hz); $^{13}$C NMR (75.5 MHz, CDCl$_3$): δ 173.4, 140.6, 128.6, 128.4, 126.4, 51.7, 35.8, 31.0.

Example 20(i)

1,3-Diphenylpropan-1-one (41)

According to the general procedure, a solution of chalcone (50 mg, 0.24 mmol) and rac-32 (7.4 mg, 0.0047 mmol, 2.0 mol %) in CH$_2$Cl$_2$ (3 mL) was pressurized with H$_2$ to 62 bar and stirred for 96 h. Filtration of the reaction mixture and evaporation of the solvent gave 41 as a colorless solid (50 mg, 99%). mp 69-70° C. (lit.$^2$ 70-72° C.); $^1$H NMR$^{27}$ (300 MHz, CDCl$_3$): δ 7.98 (d, 2H, J=7.2 Hz), 7.6-7.2 (m, 8H), 3.33 (t, 2H, J=7.8 Hz), 3.10 (t, 2H, J=7.2 Hz); $^{13}$C NMR (75.5 MHz, CDCl$_3$): δ 199.3, 141.4, 136.9, 133.2, 128.7, 128.6, 128.5, 128.1, 126.2, 40.5, 30.2.

Example 20(j)

N-(1-Phenylethyl)aniline (42)

According to the general procedure, a solution of N-(1-phenylethylidene)aniline (50 mg, 0.26 mmol) and rac-32 (7.8 mg, 0.0050 mmol, 1.9 mol %) in CH$_2$Cl$_2$ (3 mL) was pressurized with H$_2$ to 62 bar and stirred for 72 h. Filtration of the reaction mixture and evaporation of the solvent gave 42 as a clear oil (41 mg, 81%). $^1$H NMR$^{28}$ (300 MHz, CDCl$_3$): δ 7.50-7.35 (m, 4H), 7.30-7.25 (m, 1H), 7.15 (t, 2H, J=7.5 Hz), 6.70 (t, 1H, J=7.5 Hz), 6.59 (d, 2H, J=7.5 Hz), 4.56 (quin, 1H, J=6.6 Hz), 4.08 (bs, 1H), 1.56 (d, 3H, J=6.6 Hz); $^{13}$C NMR (75.5 MHz, CDCl$_3$): δ 147.4, 145.4, 129.3, 128.8, 127.0, 126.0, 117.4, 113.4, 53.6, 25.2.

Example 20(k)

N-Benzyl-1-phenylethanamine (43)

According to the general procedure, a solution of 1-phenyl-N-(1-phenylethylidene)methanamine (50 mg, 0.24 mmol) and rac-32 (7.5 mg, 0.0048 mmol, 2.0 mol %) in CH$_2$Cl$_2$ (3 mL) was pressurized with H$_2$ to 62 bar and stirred for 72 h. Filtration of the reaction mixture and evaporation of the solvent gave 43 as a clear oil (45 mg, 88%). $^1$H NMR$^{29}$ (300 MHz, CDCl$_3$): δ 7.35-7.27 (m, 10H), 3.85 (q, 1H, J=6.6 Hz), 3.66 (ABq, 2H, J=13.2 Hz), 1.59 (bs, 1H), 1.39 (d, 3H, J=6.6 Hz); $^{13}$C NMR (75.5 MHz, CDCl$_3$): δ 145.7, 140.8, 128.6, 128.5, 128.3, 127.0, 126.95, 126.8, 57.6, 51.8, 24.7.

Example 20(l)

3,7-Dimethyloctan-1-ol (44)

According to the general procedure, a solution of geraniol (52 μL, 0.29 mmol) and rac-32 (9.0 mg, 0.0057 mmol, 2.0 mol %) in CH$_2$Cl$_2$ (3 mL) was pressurized with H$_2$ to 62 bar and stirred for 24 h. Filtration of the reaction mixture and evaporation of the solvent gave 44 as a clear liquid (47 mg, 98%). $^1$H NMR$^{30}$ (300 MHz, CDCl$_3$): δ 3.68 (m, 2H), 1.61-1.17 (m, 10H), 0.90 (s, 9H); $^{13}$C NMR (75.5 MHz, CDCl$_3$): δ 61.4, 30.1, 39.4, 37.5, 29.7, 28.1, 24.8, 22.8, 22.7, 19.8.

Example 20(m)

Pyrrolidine-2,5-dione (45)

According to the general procedure, a solution of maleimide (32 mg, 0.33 mmol) and rac-32 (10.4 mg, 0.0066 mmol, 2.0 mol %) in CH$_2$Cl$_2$ (3 mL) was pressurized with H$_2$ to 62 bar and stirred for 96 h. Filtration of the reaction mixture and evaporation of the solvent gave 45 as a colorless solid (27 mg, 82%). mp 125-127° C. (lit.$^{31}$ 125-127° C.). $^1$H NMR$^4$ (300 MHz, acetone-d$_6$): δ 2.68 (s, 4H), 9.88 (bs, 1H); $^{13}$C NMR$^{32}$ (75.5 MHz, acetone-d$_6$): δ 178.9, 30.2.

Example 20(n)

Cyclohexanone (46)

According to the general procedure, a solution of cyclohexenone (30 μL, 0.31 mmol) and rac-32 (9.8 mg, 0.0062 mmol, 2.0 mol %) in CH$_2$Cl$_2$ (3 mL) was pressurized with H$_2$ to 62 bar and stirred for 48 h. Filtration of the reaction mixture and evaporation of the solvent gave 46 as a clear liquid (26 mg, 84%). $^1$H NMR$^{32}$ (300 MHz, CDCl$_3$): δ 2.31 (t, 4H, J=6.9 Hz), 1.85-1.81 (m, 4H), 1.70-1.69 (m, H); $^{13}$C NMR$^{32}$ (75.5 MHz, CDCl$_3$): δ 212.2, 40.1, 27.1, 25.1.

Example 20(o)

2,3-Dihydronaphthalene-1,4-dione (47)

According to the general procedure, a solution of naphthoquinone (50 mg, 0.31 mmol) and rac-32 (10.0 mg, 0.0063 mmol, 2.0 mol %) in CH$_2$Cl$_2$ (3 mL) was pressurized with H$_2$ to 62 bar and stirred for 72 h. Filtration of the reaction mixture and evaporation of the solvent gave the crude product, which was purified by column chromatography (30% EtOAc in hexane, silica gel) to give 47 (45 mg, 89%) as a 2:1 mixture of 2,3-dihydronaphthalene-1,4-dione and 1,4-dihydronaphtha-lene-1,4-diol. $^1$H NMR (300 MHz, acetone-d$_6$, 2,3-dihydronaphthalene-1,4-dione$^{33}$): δ 8.00-7.97 (m, 2H), 7.83-7.81 (m, 2H), 3.11 (s, 4H); 1,4-(dihydronaphthalene-1,4-diol$^{34}$): δ 8.32 (bs, 2H), 8.18-8.15 (m, 2H), 7.47-7.43 (m, 2H), 6.73 (s, 2H).

Example 20(p)

Chroman-4-one (48)

According to the general procedure, a solution of chromone (45 mg, 0.31 mmol), Hünig's base (540 μL) and rac-32 (9.8 mg, 0.0062 mmol, 2.0 mol %) in PhMe (3 mL) was pressurized with H$_2$ to 100 bar and stirred for 48 h. Filtration of the reaction mixture and evaporation of the solvent gave the crude product, which was purified by column chromatography (30% EtOAc in hexane, silica gel) to give 48 (30 mg, 66%) as a colorless oil. $^1$H NMR$^{35}$ (300 MHz, CDCl$_3$): δ 7.90 (dd, 1H J=7.8, 1.5 Hz), 7.50-7.45 (m, 1H), 7.05-6.96 (m, 2H), 4.54 (t, 2H, J=6.6 Hz), 2.82 (t, 2H, J=6.3 Hz); $^{13}$C NMR (75.5 MHz, CDCl$_3$): δ 192.0, 162.0, 136.1, 127.3, 121.5, 118.0, 67.1, 37.9.

Example 20(q)

5-Isopropyl-2-methylcyclohex-2-enone (49)

According to the general procedure, a solution of carvone (45 μL, 0.29 mmol) and rac-32 (8.0 mg, 0.0051 mmol, 1.8 mol %) in CH$_2$Cl$_2$ (3 mL) was pressurized with H$_2$ to 62 bar and stirred for 48 h. Filtration of the reaction mixture and evaporation of the solvent gave 49 as a colorless oil (43 mg, 96%). $^1$H NMR$^{36}$ (300 MHz, CDCl$_3$): δ 6.72-6.69 (m, 1H), 2.53-2.47 (m, 1H), 2.37-2.27 (m, 1H), 2.13-1.99 (m, 2H), 1.85-1.78 (m, 1H), 1.73-1.72 (m, 3H), 1.54 (quin, 1H, J=6.6

Hz), 0.87 (dd, 6H, J=6.9 Hz, 0.9 Hz); $^{13}$C NMR (75.5 MHz, CDCl$_3$): δ 200.6, 145.2, 135.2, 42.0, 41.9, 31.9, 29.8, 19.5, 19.4 15.6.

Example 21

Palladium Catalyzed Suzuki-Miyaura and Buchwald-Hartwig Coupling Using 12f as a Ligand General Procedure A (Suzuki-Miyaura Couplings). An oven-dried reaction tube under argon containing a mixture of phenylboronic acid (91 mg, 0.75 mmol), CsF (228 mg, 1.50 mmol), Pd(OAc)$_2$ (2 mg, 0.01 mmol) and 12f (8 mg, 0.02 mmol) in dioxane (2.5 mL) was treated with an aryl halide 50a-g (0.50 mmol) and stirred at room temperature for 5 min before heating to reflux for 22 h. After cooling to room temperature and diluting with Et$_2$O (7 mL), the mixture was filtered through a pipette containing a plug of silica gel and eluted with additional Et$_2$O. Evaporation of the solvent under reduced pressure and recrystallization or column chromatography gave the purified products 51a-g. The results are shown in Table 4.

Example 21(a)

4-Trifluoromethylbiphenyl

According to General Procedure A, a mixture of 4-chloro trifluoromethylbenzene (0.07 mL, 0.50 mmol), phenylboronic acid (91 mg, 0.75 mmol), CsF (228 mg, 1.50 mmol), Pd(OAc)$_2$ (2 mg, 0.01 mmol) and 12f (8 mg, 0.02 mmol) in 1,4-dioxane (2.5 mL) was heated to reflux, cooled and filtered. Column chromatography (2% EtOAc in hexane, silica gel) gave 51a (104 mg, 94%) as a colorless crystalline solid. mp 66-69° C. (95% EtOH) (66-68° C.). $^1$H NMR (300 MHz, CDCl$_3$) δ 7.70 (s, 4H), 7.60 (d, 2H, J=7.2 Hz), 7.50-7.41 (m, 3H).

Example 21(b)

4-Phenylacetophenone (51b)

According to General Procedure A, a mixture of 4-chloroacetophenone (65 μL, 0.50 mmol), phenylboronic acid (91 mg, 0.75 mmol), CsF (228 mg, 1.50 mmol), Pd(OAc)$_2$ (2 mg, 0.01 mmol) and ligand 12f (8 mg, 0.02 mmol) in 1,4-dioxane (2.5 mL) was heated to reflux, cooled and filtered. After evaporation of the solvent, recrystallization from hexane containing a small amount of EtOAc gave 51b (86 mg, 88%) as colorless crystals. $^1$H NMR (300 MHz, CDCl$_3$) δ 8.05 (d, 2H, J=8.4 Hz), 7.69 (d, 2H, J=8.4 Hz), 7.63 (d, 2H, J=7.2 Hz), 7.50-7.40 (m, 3H), 2.64 (s, 3H); $^{13}$C NMR (75.5 MHz, CDCl$_3$) δ 197.7, 145.8, 139.8, 135.8, 128.93, 128.89, 128.2, 127.24, 127.20, 26.6.

Example 21(c)

4-Cyanobiphenyl (51c)

According to General Procedure A, a mixture 4-chlorobenzonitrile (69 mg, 0.50 mmol), phenylboronic acid (91 mg, 0.75 mmol), CsF (228 mg, 1.50 mmol), Pd(OAc)$_2$ (2 mg, 0.01 mmol) and 12f (8 mg, 0.02 mmol) in 1,4-dioxane (2.5 mL) was heated to reflux, cooled and filtered. Evaporation of the solvent under reduced pressure and column chromatography of the pre-adsorbed crude material (5% Et$_2$O in hexanes, silica gel) gave 51c (83 mg, 92%) as a colorless solid. $^1$H NMR (300 MHz, CDCl$_3$) δ 7.69 (q, 4H, J=6 Hz), 7.61-7.57 (m, 2H), 7.52-7.40 (m, 3H); $^{13}$C NMR (75.5 MHz, CDCl$_3$) δ 145.6, 139.1, 132.5, 129.0, 128.6, 127.6, 127.1, 118.8, 110.8.

Example 21(d)

2-Nitrobiphenyl (51d)

According to General Procedure A, a mixture of o-chloronitrobenzene (79 mg, 0.50 mmol), phenylboronic acid (91 mg, 0.75 mmol), CsF (228 mg, 1.50 mmol), Pd(OAc)$_2$ (2 mg, 0.01 mmol) and 12f (8 mg, 0.02 mmol) in 1,4-dioxane (2.5 mL) has heated to reflux, cooled and filtered. Evaporation of the solvent under reduced pressure and column chromatography of the pre-adsorbed crude material (1% Et$_2$O in hexane, silica gel) gave 51d (73 mg, 73%) as a bright yellow oil. $^1$H NMR (300 MHz, CDCl$_3$) δ 7.86 (d, 1H, J=8.0 Hz), 7.62 (t, 1H, J=7.5 Hz), 7.51-7.40 (m, 5H), 7.34-7.31 (m, 2H); $^{13}$C NMR (75.5 MHz, CDCl$_3$) δ 149.3, 137.4, 136.3, 132.2, 131.9, 128.7, 128.2, 128.1, 127.9, 124.0.

Example 21(e)

4-Methoxybiphenyl (51e)

According to General Procedure A, a mixture of 4-chloroanisole (0.06 mL, 0.50 mmol), phenylboronic acid (91 mg, 0.75 mmol), CsF (228 mg, 1.50 mmol), Pd(OAc)$_2$ (2 mg, 0.01 mmol) and 12f (8 mg, 0.02 mmol) in 1,4-dioxane (2.5 mL) was heated to reflux, cooled and filtered. Evaporation of the solvent under reduced pressure and column chromatography of the pre-adsorbed crude material (0.5-1.0% isopropanol/hexane, silica gel) gave 51e (64 mg, 70%) as a colorless solid. $^1$H NMR (300 MHz, CDCl$_3$) δ 7.54 (t, 4H, J=6.8 Hz), 7.42 (t, 2H, J=6.8 Hz), 7.32-7.26 (m, 1H), 6.99 (d, 2H, J=8.7 Hz), 3.86 (s, 3H); $^{13}$C NMR (75.5 MHz, CDCl$_3$) δ 159.1, 140.8, 133.8, 128.7, 128.1, 126.7, 126.6, 114.2, 55.3.

Example 21(f)

4-Methylbiphenyl (51f)

According to General Procedure A, a mixture of 4-chlorotoluene (59 μL, 0.50 mmol), phenylboronic acid (91 mg, 0.75 mmol), CsF (228 mg, 1.50 mmol), Pd(OAc)$_2$ (2 mg, 0.01 mmol) and 12f (8 mg, 0.02 mmol) in 1,4-dioxane (2.5 mL) was heated to reflux, cooled and filtered. Evaporation of the solvent under reduced pressure and column chromatography of the pre-adsorbed crude material (1% Et$_2$O in hexane silica gel) gave 51f (47 mg, 56%) as a colorless solid. $^1$H NMR (300 MHz, CDCl$_3$) δ 7.59 (d, 2H, J=7.8 Hz), 7.51 (d, 2H, J=7.8 Hz), 7.44 (d, 2H, J=7.8 Hz), 7.35-7.24 (m, 3H), 2.41 (s, 3H); $^{13}$C NMR (75.5 MHz, CDCl$_3$) δ 141.1, 138.3, 137.0, 129.5, 128.7, 127.0, 126.9, 21.1.

Example 21(g)

5,7-Diphenyl-8-aminoquinoline (51g)

According to General Procedure A, a mixture of 5,7-dibromo-8-aminoquinoline (14 g, 100 mg, 0.33 mmol), phenylboronic acid (60 mg, 0.50 mmol), CsF (150 mg, 0.99 mmol), Pd(OAc)$_2$ (1.3 mg, 0.007 mmol) and ligand 12f (5.3 mg, 0.013 mmol) in 1,4-dioxane (2.5 mL) was heated to reflux, cooled and filtered. After evaporation of the solvent, recrystallization from Et$_2$O/hexane gave 51g (86 mg, 88%) as colorless crystals. mp: 100-102° C. (Et$_2$O/hexane). IR (KBr):

$\nu_{max}$ 3450, 3347, 3050, 3023, 1583 cm$^{-1}$. $^1$H NMR (300 MHz, CDCl$_3$): δ 8.85-8.80 (m, 1H), 8.28 (dd, 1H, J=8.4, 1.5 Hz), 7.66-7.63 (m, 2H), 7.54-7.44 (m, 6H), 7.42-7.34 (m, 4H), 5.32 (s, 2H). $^{13}$C NMR (75.5 MHz, CDCl$_3$): δ 147.5, 140.2, 139.9, 138.3, 134.2, 130.2, 130.0, 129.2, 129.0, 128.4, 128.2, 127.2, 126.8, 126.1, 121.7, 121.2. EIMS (m/z, (%)): 296 (72), 219 (24), 86 (100), 47 (85). HRMS (EI; m/z): calcd for C$_{21}$H$_{16}$N$_2$: 296.1314. Found 296.1312.

Example 21(h)

General Procedure B (Buchwald-Hartwig Couplings). An oven-dried reaction tube under argon containing a mixture of Pd$_2$(dba)$_3$.CHCl$_3$ (10 mg, 0.01 mmol), 12f (8 mg, 0.02 mmol) and NaOt-Bu (67 mg, 0.70 mmol) in PhMe (2.5 mL) was treated with an aryl halide (0.50 mmol) and morpholine (52 μL, 0.60 mmol). The resulting green-brown mixture was heated at 100° C. for 22 h. After cooling to room temperature, the reaction mixture was diluted with Et$_2$O (5 mL) and filtered through a pipette containing a plug of silica gel while eluting with additional Et$_2$O. Evaporation of the solvent under reduced pressure and recrystallization or column chromatography of crude material gave products. The results are shown in Table 4.

N-(4-Trifluoromethylphenyl)morpholine (52a)

According to General Procedure B, a mixture of 4-chloro trifluoromethylbenzene (67 μL, 0.50 mmol), morpholine (52 μL, 0.60 mmol), NaOt-Bu (67 mg, 0.70 mmol), Pd$_2$(dba)$_3$.CHCl$_3$ (10 mg, 0.01 mmol) and 12f (8 mg, 0.02 mmol) in PhMe (2.5 mL) was heated, cooled and filtered. Evaporation of the solvent under reduced pressure and column chromatography of the pre-adsorbed crude material (20% Et$_2$O in hexane, silica gel) gave 52a (89 mg, 77%) as off-white crystals. $^1$H NMR (300 MHz, CDCl$_3$) δ 7.50 (d, 2H, J=8.7 Hz), 6.92 (d, 2H, J=8.7 Hz), 3.87 (t, 4H, J=4.8 Hz), 3.24 (t, 4H, J=5.1 Hz); $^{13}$C NMR (75.5 MHz, CDCl$_3$) δ 153.3, 126.4 (q, J=3 Hz), 124.6 (q, J=271 Hz), 120.9 (q, J=33 Hz) 114.3, 66.6, 48.1.

Example 21(i)

N-(4-Acetylphenyl)morpholine (52b)

According to General Procedure B, a mixture of 4-chloroacetophenone (65 μL, 0.50 mmol), morpholine (52 μL, 0.60 mmol), NaOt-Bu (67 mg, 0.70 mmol), Pd$_2$(dba)$_3$.CHCl$_3$ (10 mg, 0.01 mmol) and 12f (8 mg, 0.02 mmol) in PhMe (2.5 mL) was heated, cooled and filtered. Evaporation of the solvent under reduced pressure and column chromatography of the pre-adsorbed crude material (83:2:15 to 78:2:20 hexane/Et$_3$N/EtOAc, silica gel) gave 52b (76 mg, 74%) as a pale yellow solid. $^1$H NMR (300 MHz, CDCl$_3$) δ 7.90 (d, 2H, J=9.0 Hz), 6.87 (d, 2H, J=9.0 Hz), 3.86 (t, 4H, J=4.8 Hz), 3.31 (t, 4H, J=5.1 Hz), 2.53 (s, 3H); $^{13}$C NMR (75.5 MHz, CDCl$_3$) 196.4, 154.2, 130.3, 128.1, 113.2, 66.5, 47.5, 26.1.

Example 21(j)

N-(2-Nitrophenyl)morpholine (52d)

According to General Procedure B, a mixture of 2-nitro chlorobenzene (79 mg, 0.50 mmol), morpholine (52 μL, 0.60 mmol), NaOt-Bu (67 mg, 0.70 mmol), Pd$_2$(dba)$_3$.CHCl$_3$ (10 mg, 0.01 mmol) and 12f (0.4 mL of 0.05 M solution in PhMe) in PhMe (2.5 mL) was heated, cooled and filtered. Evaporation of the solvent under reduced pressure and column chromatography of the pre-adsorbed crude material (40% Et$_2$O in hexane, silica gel) gave 52d (45 mg, 43%) as a yellow oil. $^1$H NMR (300 MHz, CDCl$_3$) δ 7.79 (d, 1H, J=8.1 Hz), 7.52-7.47 (m, 1H), 7.15 (d, 1H, J=8.3 Hz), 7.10-7.06 (m, 1H), 3.85-3.83 (m, 4H), 3.07-3.04 (m, 4H); $^{13}$C NMR (75.5 MHz, CDCl$_3$) δ 145.8, 143.7, 133.5, 125.9, 122.3, 120.9, 66.8, 52.1.

Example 21(k)

N-(4-Methoxyphenyl)morpholine (52e)

According to General Procedure B, a mixture of 4-bromoanisole (63 μL, 0.50 mmol), morpholine (52 μL, 0.60 mmol), NaOt-Bu (67 mg, 0.70 mmol), Pd$_2$(dba)$_3$.CHCl$_3$ (10 mg, 0.01 mmol), and 12f (8 mg, 0.02 mmol) in PhMe (2.5 mL) was heated, cooled and filtered. Evaporation of the solvent under reduced pressure and column chromatography of the pre-adsorbed crude material (2:50:48 Et$_3$N/Et$_2$O/hexane, silica gel) gave 52e (64 mg, 67%) as an off-white solid. $^1$H NMR (300 MHz, CDCl$_3$) δ 6.92-6.84 (m, 4H), 3.86 (t, 4H, J=4.8 Hz), 3.77 (s, 3H), 3.06 (t, 4H, J=4.8 Hz); $^{13}$C NMR (75.5 MHz, CDCl$_3$) δ 153.9, 145.5, 117.7, 114.4, 66.9, 55.5, 50.7.

Example 21(h)

N-Phenylmorpholine (52h)

According to General Procedure B, a mixture of bromobenzene (53 μL, 0.50 mmol), morpholine (52 μL, 0.60 mmol), NaOt-Bu (67 mg, 0.70 mmol), Pd$_2$(dba)$_3$.CHCl$_3$ (10 mg, 0.01 mmol) and 12f (8 mg, 0.02 mmol) in PhMe (2.5 mL), was heated, cooled and filtered. Column chromatography (6:1:93 Et$_2$O/Et$_3$N/hexane, silica gel) gave 52h (67 mg, 82%) as a colorless solid. $^1$H NMR (600 MHz, CDCl$_3$) δ 7.32 (t, 2H, J=4.2 Hz), 6.97-6.91 (m, 3H), 3.90 (t, 4H, J=2.4 Hz), 3.19 (t, 4H, J=2.4 Hz); $^{13}$C NMR (150.9 MHz, CDCl$_3$) δ 151.3, 129.2, 120.1, 115.7, 67.0, 49.4.

Example 22

2-Benzyl-3-methyl-2-aza-spiro[4.5]decane (54)

A solution of aminoalkene 53 (135 mg, 0.55 mmol) and S-32 (22 mg, 2.5 mol %) in dioxane (2 mL) under argon was heated to reflux for 22 h. After cooling to room temperature, the solvent was removed on a rotary evaporator. The residue was taken up in Et$_2$O and filtered through a pipette of silica gel and concentrated again in vacuo. The crude product mixture was dissolved in THF (2 mL), treated with Ac$_2$O (63 μL, 1.2 equiv), Et$_3$N (0.23 mL, 3.0 equiv) and DMAP (3 mg, 0.05 equiv), and heated at 45° C. for 16 h to acylate any remaining secondary amines. The reaction mixture was then diluted with Et$_2$O and extracted with 1 M aq. HCl (3×5 mL) and the combined acidic extracts were made alkaline (pH 12) by addition of 6 M aq. NaOH. The aqueous phase was back-extracted with Et$_2$O (3×5 mL), washed with brine, dried over anhyd. Na$_2$SO$_4$, filtered and concentrated in vacuo to give 54 (87 mg, 64%) as a pale yellow oil. $^1$H NMR (300 MHz, CDCl$_3$): δ 7.38-7.22 (m, 5H), 4.04 (d, 1H, J=13.2 Hz), 3.12 (d, 1H, J=13.2 Hz), 2.81 (d, 1H, J=9.3 Hz), 2.58-2.46 (m, 1H), 1.90 (d, 1H, J=9.3 Hz), 1.78 (ABq, 1H, J=12.6, 6.9 Hz), 1.50-1.25 (m, 11H), 1.17 (d, 3H, J=6.0 Hz). The results are shown in Table 5.

Example 23

Other Derivatives of 12i and 12h (a) (±)-2-Phenyl-1-dimethylaminoferrocene (55)

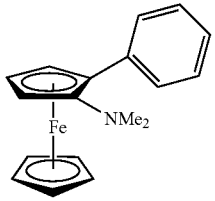

Racemic iodide 12i (89 mg, 0.25 mmol), PhB(OH)$_2$ (34 mg, 0.28 mmol) and Pd(PPh$_3$)$_4$ (29 mg, 2.51×10$^{-2}$ mmol) were added to a dry Schlenk flask, followed by dimethoxyethane (DME, 2 mL) and an aqueous solution of 3 M NaOH (0.17 mL, 0.50 mmol). Argon was bubbled through the resulting mixture for 10 minutes, and the system was heated at 55° C. for 14 h. The reaction was allowed to cool to room temperature, diluted with Et$_2$O, washed with water (1×5 mL), brine (1×5 mL), dried over Na$_2$SO$_4$, filtered, and all volatiles were removed in vacuo. Flash column chromatography (silica gel, 98:2 hexane/EtOAc) afforded 55 (61 mg, 80%) as an orange oil: R$_f$ 0.45 (90:10 hex/EtOAc); IR (KBr, CHCl$_3$) $v_{max}$ 3091, 2941, 2852, 2779, 1601, 1491, 1444, 1416 cm$^{-1}$; $^1$H NMR (300 MHz, CDCl$_3$) δ 7.80-7.74 (m, 2H), 7.36-7.19 (m, 3H), 4.28-4.25 (m, 1H), 4.18 (s, 5H), 4.15-4.11 (m, 1H), 4.05 (t, 1H, J=2.7 Hz), 2.53 (s, 6H); $^{13}$C NMR (75 MHz, CDCl$_3$) δ 139.1, 128.4, 127.8, 125.9, 112.5, 78.1, 69.2, 66.5, 62.4, 58.0, 44.6; EIMS [m/z (%)] 305 (M$^+$, 100); HRMS (EI) calcd for C$_{18}$H$_{19}$N$^{56}$Fe: 305.0867. Found 305.0864.

(b) (±)-2-(3-Methylphenyl)-1-dimethylaminoferrocene (56)

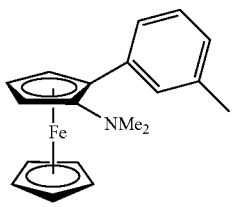

Racemic iodide 12i (102 mg, 0.29 mmol), PhB(OH)$_2$ (78 mg, 0.57 mmol) and Pd(PPh$_3$)$_4$ (33 mg, 2.86×10$^{-2}$ mmol) were added to a dry Schlenk flask, followed by DME (3 mL) and an aqueous solution of 3 M aqueous NaOH (0.25 mL, 0.70 mmol). Argon was bubbled through the resulting mixture for 10 minutes, and the system was heated at reflux for 17 h. The reaction was allowed to cool to room temperature, diluted with Et$_2$O, washed with water (1×5 mL), brine (1×5 mL), dried over Na$_2$SO$_4$, filtered, and all volatiles were removed in vacuo. Flash column chromatography (silica gel, 98:2 hexane/EtOAc) afforded 56 (85 mg, 93%) as an orange oil: R$_f$ 0.41 (90:10 hexane/EtOAc); IR (KBr, CHCl$_3$) $v_{max}$ 3093, 2940, 2848, 2778, 1605, 1487, 1452, 1416 cm$^{-1}$; $^1$H NMR (300 MHz, CDCl$_3$) δ 7.61 (d, 1H, J=7.8 Hz), 7.49 (s, 1H), 7.23 (t, 1H, J=7.5 Hz), 7.04 (d, 1H, J=7.5 Hz), 4.23 (s, 1H), 4.18 (s, 5H), 4.11 (s, 1H), 4.02 (t, 1H, J=2.7 Hz), 2.52 (s, 6H), 2.39 (s, 3H); $^{13}$C NMR (75 MHz, CDCl$_3$) δ 139.0, 137.1, 129.0, 127.7, 126.7, 125.7, 112.4, 77.9, 69.1, 66.7, 62.2, 58.1, 44.6, 21.5; EIMS [m/z (%)] 319 (M$^+$, 100); HRMS (EI) calcd for C$_{19}$H$_{21}$N$^{56}$Fe: 319.1023. Found 319.1025.

(c) (±)-2-(2-Methoxyphenyl)-1-dimethylaminoferrocene (57)

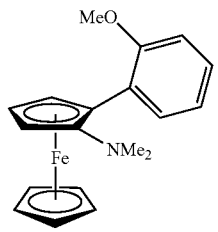

Racemic iodide 12i (101 mg, 0.28 mmol), 2-methoxyphenylboronic acid (86 mg, 0.57 mmol) and Pd(PPh$_3$)$_4$ (33 mg, 2.86×10$^{-2}$ mmol) were added to a dry Schlenk flask, followed by DME (3 mL) and an aqueous solution of 3 M aqueous NaOH (0.24 mL, 0.70 mmol). Argon was bubbled through the resulting mixture for 10 minutes, and the system was heated to reflux for 14 h. The reaction mixture was allowed to cool to room temperature, diluted with Et$_2$O, washed with water (1×5 mL), brine (1×5 mL), dried over Na$_2$SO$_4$, filtered, and all volatiles were removed in vacuo. Gradient flash column chromatography (silica gel, 98:2→95:5 hexane/EtOAc) afforded 57 (83 mg, 87%) as an orange oil that solidified on standing: R$_f$ 0.19 (95:5 hexane/EtOAc); mp 92-93° C. (hexane); IR (KBr) $v_{max}$ 3082, 2941, 2833, 2776, 1597, 1450, 1411 cm$^{-1}$; $^1$H NMR (300 MHz, CDCl$_3$) δ 8.09 (dd, 1H, J=7.5, 1.8 Hz), 7.26 (td, 1H, J=7.8, 1.8 Hz), 7.02 (td, 1H, J=7.5, 0.9 Hz), 6.87 (d, 1H, J=8.4 Hz), 4.27 (t, 1H, J=3.6 Hz), 4.24 (s, 5H), 4.09 (t, 1H, J=2.1 Hz), 4.05 (t, 1H, J=2.7 Hz), 3.79 (s, 3H), 2.47 (s, 6H); $^{13}$C NMR (75 MHz, CDCl$_3$) δ 157.5, 132.6, 127.5, 127.0, 120.0, 113.1, 110.5, 75.5, 68.9, 66.8, 62.0, 56.8, 55.6, 44.1; EIMS [m/z (%)] 335 (M$^+$, 100), 229 (24); HRMS (EI) calcd for C$_{19}$H$_{21}$NO$^{88}$Fe: 335.0972. Found 335.0978.

(d) (±)-2-(2-Bromophenyl)-1-dimethylaminoferrocene (58)

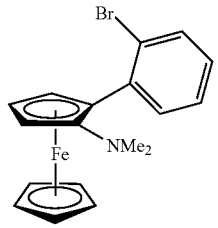

Racemic iodide 12i (355 mg, 1.00 mmol), 2-bromophenylboronic acid (210 mg, 1.05 mmol) and Pd(PPh$_3$)$_4$ (115 mg, 0.10 mmol) were added to a dry Schlenk flask, followed by DME (10 mL) and an aqueous solution of 3 M aqueous NaOH (0.50 mL, 1.50 mmol). Argon was bubbled through the resulting mixture for 10 minutes, and the system was heated at reflux for 15 h. The reaction mixture was allowed to cool to room temperature, diluted with Et$_2$O, washed with water (1×5 mL), brine (1×5 mL), dried over Na$_2$SO$_4$, filtered, and all volatiles were removed in vacuo. Gradient flash column chromatography (silica gel, 97:3→95:5 t-BuOMe/hexane) afforded 58 (177 mg, 46%) as an orange oil: R$_f$ 0.38 (90:10 hex/EtOAc); IR (KBr, CHCl$_3$) ν$_{max}$ 3091, 2947, 2846, 2783, 1587, 1502, 1485, 1416 cm$^{-1}$; $^1$H NMR (300 MHz, CDCl$_3$) δ 8.12 (dd, 1H, J=7.7, 1.5 Hz), 7.26 (dd, 1H, J=8.1, 1.2 Hz), 7.34 (td, 1H, J=7.5, 1.2 Hz), 7.13 (td, 1H, J=7.8, 1.8 Hz), 4.32 (s, 5H), 4.13 (t, 1H, J=1.8 Hz), 4.10-4.05 (m, 2H), 2.41 (s, 6H); $^{13}$C NMR (75 MHz, CDCl$_3$) δ 157.5, 132.6, 127.5, 127.0, 120.0, 113.1, 110.5, 75.5, 68.9, 66.8, 62.0, 56.8, 55.6, 44.1; EIMS [m/z (%)] 385 ($^{81}$BrM$^+$, 91), 383 (79BrM$^+$, 100), 182 (62); HRMS (EI) calcd for C$_{18}$H$_{18}$N$^{56}$Fe$^{79}$Br: 382.9972. Found 382.9974.

(e) (±)-2-(2-Diphenylphosphinophenyl)-1-dimethylaminoferrocene (60)

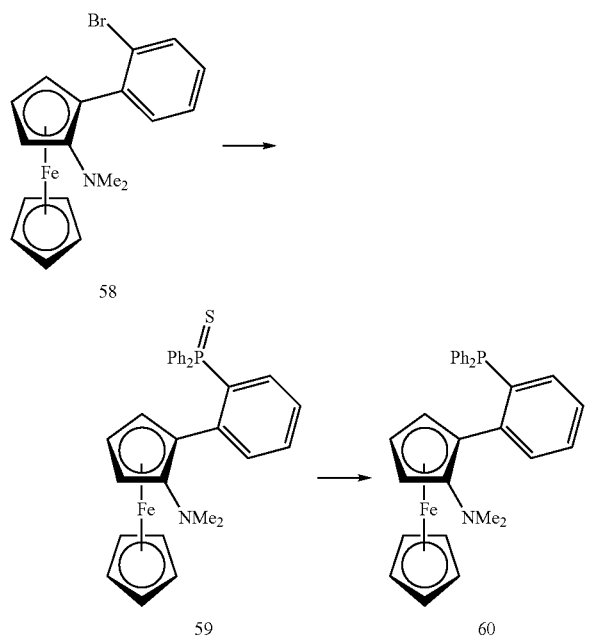

A solution of bromide 58 (194 mg, 0.51 mmol) in THF (5 mL) in a Schlenk tube under argon was cooled to −78° C. and treated with a solution of n-BuLi (0.28 mL, 0.56 mmol, 2.00 M in hexanes). After 10 minutes, ClPPh$_2$ (0.11 mL, 0.61 mmol) was added and the reaction mixture allowed to warm to room temperature over 2.5 h. The reaction mixture was diluted with Et$_2$O, washed with a saturated solution of NaHCO$_3$ (1×10 mL), water (1×10 mL), brine (1×10 mL), dried over Na$_2$SO$_4$, filtered, and all volatiles were removed in vacuo. The crude was dissolved in 75:25 Et$_2$O/pentane, filtered through a pad of silica, eluting with 75:25 Et$_2$O/pentane and evaporation of the filtrate afforded the crude product. For convenience of purification, the phosphine was treated with sulfur (19 mg, 0.60 mmol) in PhMe (5 mL) at 40° C. for 15 h. After cooling to room temperature, the mixture was pre-adsorbed on silica gel and loaded on a column. Flash column chromatography (silica gel, 85:15 pentane/Et$_2$O) afforded phosphine sulfide 59 (274 mg, 96%) as an orange-red oil: R$_f$ 0.18 (90:10 hexane/EtOAc); IR (KBr, CHCl$_3$) ν$_{max}$ 2918, 2848, 2779, 1481, 1437, 1097 cm$^{-1}$; $^1$H NMR (600 MHz, CDCl$_3$) δ 8.56-8.51 (m, 1H), 7.87-7.81 (m, 2H), 7.69-7.63 (m, 2H), 7.50 (t, 1H, J=3.6 Hz), 7.47-7.42 (m, 1H), 7.41-7.36 (m, 2H), 7.35-7.30 (m, 1H), 7.28-7.09 (m, 4H), 4.28 (s, 1H), 4.08 (s, 5H), 3.72 (s, 1H), 3.62 (t, 1H, J=1.2 Hz), 2.39 (s, 6H); $^{13}$C NMR (150 MHz, CDCl$_3$) δ 142.1 (d, $J^{13}_{C}$-$^{31}_{P}$=9.0 Hz), 135.9 (d, $J^{13}_{C}$-$^{31}_{P}$=10.5 Hz), 134.1 (d, $J^{13}_{C}$-$^{31}_{P}$=84.0 Hz), 133.8 (d, $J^{13}_{C}$-$^{31}_{P}$=12.0 Hz), 133.4 (d, $J^{13}_{C}$-$^{31}_{P}$=58.5 Hz), 132.26 (d, $J^{13}_{C}$-$^{31}_{P}$=6.0 Hz), 132.22 (d, $J^{13}_{C}$-$^{31}_{P}$=27.0 Hz), 131.8 (d, $J^{13}_{C}$-$^{31}_{P}$=6.0 Hz), 131.3 (d, $J^{13}_{C}$-$^{31}_{P}$=3.0 Hz), 130.99 (d, $J^{13}_{C}$-$^{31}_{P}$=10.5 Hz), 130.91 (d, $J^{13}_{C}$-$^{31}_{P}$=3.0 Hz), 130.55 (d, $J^{13}_{C}$-$^{31}_{P}$=3.0 Hz), 130.27 (d, $J^{13}_{C}$-$^{31}_{P}$=1.5 Hz), 128.5 (d, $J^{13}_{C}$-$^{31}_{P}$=12.0 Hz), 128.03 (d, $J^{13}_{C}$-$^{31}_{P}$=12.0 Hz), 127.84 (d, $J^{13}_{C}$-$^{31}_{P}$=12.0 Hz), 126.0 (d, $J^{13}_{C}$-$^{31}_{P}$=13.5 Hz), 113.7, 81.8 (d, $J^{13}_{C}$-$^{31}_{P}$=4.5 Hz), 77.2, 76.9 (d, $J^{13}_{C}$-$^{31}_{P}$=31.5 Hz), 61.5, 55.8, 44.2; $^{31}$P NMR (243 MHz, CDCl$_3$) δ 43.6; EIMS [m/z (%)] 521 (M$^+$, 50), 489 (10), 456 (39), 218 (100); HRMS (EI) calcd for C$_{30}$H$_{28}$NPS$^{56}$Fe: 521.1029. Found 521.1027.

A portion of 59 (63 mg, 0.12 mmol) in MeCN (2 mL) was added to a suspension of activated Ni—Al catalyst [518 mg, 6.04 mmol, pre-activated by digesting with an aqueous solution of 6 M NaOH for 1 h at 50° C. (caution: exothermic); after cooling to room temperature, the Ni—Al catalyst was washed successively with H$_2$O (10×3 mL), MeOH (4×3 mL) and MeCN (3×3 mL)]. The resulting mixture was heated at 60° C. under argon for 18 h. After cooling to room temperature, the mixture was filtered through a pad of Celite, eluting with MeCN, and all volatiles were removed in vacuo. The mixture was dissolved in 95:5 hexanes/EtOAc and carefully filtered through a pad of silica gel, eluting with 95:5 hexanes/EtOAc, to afford 60 (43 mg, 73%) as a yellow-orange oil: R$_f$ 0.35 (silica, 90:10 hex/EtOAc); IR (KBr, CHCl$_3$) ν$_{max}$ 3070, 3051, 2948, 2849, 2781, 1499, 1480, 1434 cm$^{-1}$; $^1$H NMR (600 MHz, CDCl$_3$) δ 8.20-8.16 (m, 1H), 7.42-7.38 (m, 1H), 7.31-7.25 (m, 6H), 7.23-7.15 (m, 5H), 7.02-6.99 (m, 1H), 4.28 (s, 5H), 4.05 (t, 1H, J=1.8 Hz), 3.94 (t, 1H, J=3.0 Hz), 3.85 (t, 1H, J=1.2 Hz), 2.29 (s, 6H); $^{13}$C NMR (150 MHz, CDCl$_3$) δ 143.8 (d, $J^{13}_{C}$-$^{31}_{P}$=28.5 Hz), 138.4 (d, $J^{13}_{C}$-$^{31}_{P}$=13.5 Hz), 138.1 (d, $J^{13}_{C}$-$^{31}_{P}$=13.5 Hz), 135.7, 133.91, 133.76, 133.62, 133.53, 133.40, 132.84 (d, $J^{13}_{C}$-$^{31}_{P}$=6.0 Hz), 128.38, 128.15, 128.11, 128.04, 128.01, 128.00, 126.7, 125.5, 113.8, 80.93 (d, $J^{13}_{C}$-$^{31}_{P}$=10.5 Hz), 69.36 (d, $J^{13}_{C}$-$^{31}_{P}$=7.5 Hz), 68.5, 61.5, 56.8, 43.9; $^{31}$P NMR (243 MHz, CDCl$_3$) δ −13.9; EIMS [m/z (%)] 489 (M$^+$, 2), 242 (40), 199 (100); HRMS (EI) calcd for C$_{30}$H$_{28}$NP$^{56}$Fe: 489.1308. Found 489.1309.

(f) (±)-2-Hydroxymethyl-1-dimethylaminoferrocene (61)

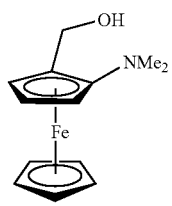

A stirred mixture of NaBH$_4$ (130 mg, 3.45 mmol) in H$_2$O (3.5 mL) was added to an ice-cold solution of racemic aldehyde 12d (443 mg, 1.72 mmol) in MeOH (10 mL) that was open to the air. After addition, a gradual colour change from red to orange was observed and the reaction mixture was allowed to warm to room temperature over 20 h. The reaction mixture was poured into an ice-cooled saturated solution of aqueous NH$_4$Cl (10 mL) and subsequently made weakly alkaline (pH 8) by addition of a saturated solution of aqueous NaHCO$_3$. The resulting mixture was extracted with Et$_2$O (2×20 mL). The combined organic extract was washed with H$_2$O (1×10 mL), brine (1×10 mL), dried over Na$_2$SO$_4$, filtered, and all volatiles were removed in vacuo. The crude product was dissolved in Et$_2$O and filtered through a pad of silica gel, eluting with Et$_2$O. Evaporation of the filtrate afforded alcohol 61 (415 mg, 93%) as an orange oil: $R_f$=0.12 (silica, 50:50 hex/EtOAc); IR (KBr, neat) $v_{max}$ 3369, 2943, 2851, 2785, 1485, 1455, 1422 cm$^{-1}$; $^1$H NMR (300 MHz, CDCl$_3$) δ 4.46 (AB q, 1H, J=12.3, 12.3 Hz), 4.21 (s, 5H), 4.12-3.98 (m, 1H), 3.97-3.94 (m, 1H), 3.93 (t, 1H, J=2.4 Hz), 3.48 (br s, 1H), 2.60 (s, 6H); $^{13}$C NMR (75 MHz, CDCl$_3$) δ 112.1, 81.7, 68.7, 65.4, 62.8, 60.3, 56.2, 45.1; EIMS [m/z (%)] 259 (M$^+$, 25), 121 (66), 86 (65), 84 (100); HRMS (EI) calcd for C$_{13}$H$_{17}$NO$^{56}$Fe: 259.0659. Found 259.0658.

(g) (±)-2-Acetoxymethyl-1-dimethylaminoferrocene (62)

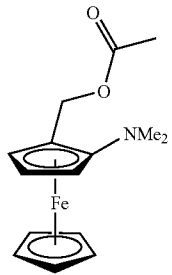

A solution of 61 (407 mg, 1.57 mmol), DMAP (19 mg, 0.16 mmol) and Et$_3$N (0.65 mL, 4.70 mmol) in THF (8 mL) was treated with Ac$_2$O (0.22 mL, 2.35 mmol) and allowed to stir at room temperature for 16 h. The reaction mixture was diluted with Et$_2$O, washed with H$_2$O (2×10 mL), brine (1×10 mL), dried over Na$_2$SO$_4$, filtered, and all volatiles were removed in vacuo. The crude product was taken up in hexanes and filtered through a pad of silica gel, eluting with 60:40 hexane/EtOAc. Evaporation of the filtrate afforded acetate 62 (413 mg, 88%) as a dark orange oil: $R_f$=0.44 (silica, 50:50 hex/EtOAc); IR (KBr, neat) $v_{max}$ 3095, 3014, 2947, 2848, 2783, 1736, 1486, 1454 cm$^{-1}$; $^1$H NMR (300 MHz, CDCl$_3$) δ 5.03 (AB q, 2H, J=12.0, 12.0 Hz), 4.16 (s, 5H), 4.10 (t, 1H, J=1.8 Hz), 4.02-3.93 (m, 2H), 2.61 (s, 6H), 2.03 (s, 1H), $^{13}$C NMR (75 MHz, CDCl$_3$) δ 170.9, 114.4, 68.7, 67.7, 63.5, 61.9, 56.6, 45.2, 21.0; EIMS [m/z (%)] 301 (M$^+$, 33), 121 (100); HRMS (EI) calcd for C$_{15}$H$_{19}$NO$_2$$^{56}$Fe: 301.0765. Found 301.0766.

(h) (±)-2-Imidazolylmethyl-1-dimethylaminoferrocene (63)

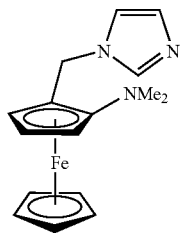

Alcohol 61 (60 mg, 0.23 mmol) and carbonyl diimidazole (47 mg, 0.29) were added to a round bottom flask equipped with a reflux condenser under argon. CH$_2$Cl$_2$ (3 mL) was added, and the stirred mixture was heated at reflux for 16 h. After cooling to room temperature, the mixture was pre-adsorbed on silica gel and loaded onto a column. Gradient flash column chromatography (silica gel, 98:0:2→93:5:2 EtOAc/MeOH/Et$_3$N) afforded imidazole 63 as a yellow-brown oil (38 mg, 53%): $R_f$=0.25 (silica, 93:5:2 EtOAc/MeOH/Et$_3$N); IR (KBr, neat) $v_{max}$ 3100, 2949, 2848, 2784, 1504, 1421 cm$^{-1}$; $^1$H NMR (300 MHz, CDCl$_3$) δ 7.50 (s, 1H), 7.00 (s, 1H), 6.92 (s, 1H), 5.11 (d, 1H, J=14.1 Hz), 4.83 (d, 1H, J=14.4 Hz), 4.16 (s, 5H), 4.10 (t, 1H, J=1.8 Hz), 4.02-3.93 (m, 2H), 2.61 (s, 6H), 2.03 (s, 1H); $^{13}$C NMR (75 MHz, CDCl$_3$) δ 136.7, 129.1, 118.9, 113.4, 75.2, 68.9, 66.6, 63.5, 57.4, 45.5, 45.3; EIMS [m/z (%)] 309 (M$^+$, 48), 121 (100); HRMS (EI) calcd for C$_{16}$H$_{19}$N$_3$$^{56}$Fe: 309.0928. Found 309.0930.

(i) (±)-2-Diethylaminomethyl-1-dimethylaminoferrocene (64)

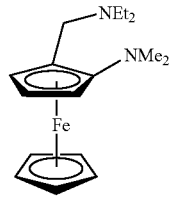

A stirred solution of alcohol 61 (90 mg, 0.35 mmol) and NaI (104 mg, 0.69 mmol) in MeCN (3 mL) under argon at room temperature was treated with ClSiMe$_3$ (0.11 mL, 0.87 mmol), resulting in the formation of fine precipitate. After stirring for 10 minutes, Et$_2$NH (0.14 mL, 1.39 mmol) was added and the reaction mixture was left to stir for a further 15 h. CH$_2$Cl$_2$ (10 mL) was added and the mixture washed with H$_2$O (3×5 mL), brine (1×5 mL), dried over Na$_2$SO$_4$, filtered, and all volatiles were removed in vacuo. The crude product was dissolved in EtOAc and filtered through a pad of silica gel, eluting with 95:3:2 EtOAc/i-PrOH/Et$_3$N. Evaporation of the filtrate afforded amine 64 (103 mg, 95%) as an orange oil: $R_f$=0.25 (silica, 95:3:2 EtOAc/i-PrOH/Et$_3$N); IR (KBr, neat) $v_{max}$ 3093, 2968, 2937, 2819, 2780, 1487, 1452, 1421 cm$^{-1}$; $^1$H NMR (300 MHz, CDCl$_3$) δ 4.13 (s, 5H), 3.97 (t, 1H, J=1.8 Hz), 3.89 (t, 1H, J=2.0 Hz), 3.86 (t, 1H, J=2.4 Hz), 3.75 (AB d, 1H, J=13.2 Hz), 3.12 (AB d, 1H, J=12.9 Hz), 2.68 (s, 6H), 2.61 (dq, 2H, J=13.8, 6.9 Hz), 2.41 (dq, 2H, J=13.0, 7.1 Hz), 0.98 (t, 6H, J=7.2); $^{13}$C NMR (75 MHz, CDCl$_3$) δ 113.7, 76.6, 68.5, 68.3, 61.7, 56.9, 52.2, 45.9, 44.9, 11.2; EIMS [m/z (%)] 314 (M$^+$, 100), 241 (39), 121 (38); HRMS (EI) calcd for C$_{17}$H$_{26}$N$_2$$^{56}$Fe: 314.1445. Found 314.1445.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

TABLE 1

Lithiation of 11 using Chiral Diamines

11 BF₃ → ent-12d
1. n-BuLi/Ligand
2. DMF

| Ligand | Yield, %, ent-12d | Enantiomeric Ratio (% ee) ent-12d |
|---|---|---|
| (−)-sparteine | 43 | 44:56 (12% ee) |
| (S,S)-N,N,N',N'-tetramethylcyclohexane-1,2-diamine (TMCDA) | 64 | 45:55 (10% ee) |
| (R,R)-19a | 71 | 61:39 (22% ee) |

TABLE 2

Lithiation of 11 using Ligand (R,R)-19a, (R,R)-19b and (S,S)-19c and Various Lithiating Reagents 11 →
1. 1.05 equiv BF₃·OEt₂, 0° C., t-BuOMe
2. 1.1 OR 2.1 equiv RLi/19a, b, or c, −78° C. → −40° C., 3 h
3. DMF, −78° C. → rt (R)-(−)-12d + (S)-(+)-12d (R,R)-(−)-19a

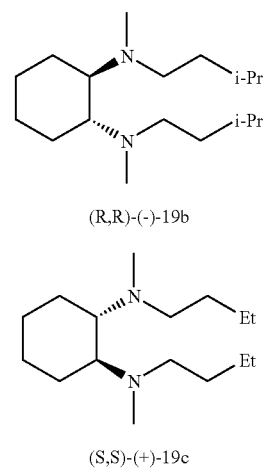

(R,R)-(−)-19b (S,S)-(+)-19c

| equiv RLi | ligand | Yield, %, 12d | R:S 12d (% ee); | recovered 11 (%) |
|---|---|---|---|---|
| 1.1 n-BuLi | (R,R)-19a | 14[1] | 81.0:19.0 (62) | 18 |
| 1.1 n-BuLi | (R,R)-19a | 13 | 72.0:28.0 (44) | n.d. |
| 2.1 n-BuLi | (R,R)-19a | 16[2] | n.d. | n.d. |
| 2.1 n-BuLi | (R,R)-19a | 71[3] | 60.5:39.5 (21) | n.d. |
| 1.6 n-BuLi | (R,R)-19a | n.d.[4] | 63.5:36.5 (27) | n.d. |
| 1.6 n-BuLi | (R,R)-19a | n.d.[5] | 61.0:39.0 (22) | n.d. |
| 1.6 n-BuLi | (R,R)-19a | n.d.[6] | 59.5:40.5 (19) | 32 |
| 1.6 n-BuLi | (R,R)-19a | n.d.[7] | 59.0:41.0 (18) | 73 |
| 1.1 n-BuLi | (R,R)-19a | 13[8] | 66.0:34.0 (32) | 73 |
| 1.1 s-BuLi | (R,R)-19a | 22 | 83.0:17.0 (66) | 70 |
| 2.1 s-BuLi | (R,R)-19a | 35[9] | 80.0:20.0 (60) | 25 |
| 1.1 i-PrLi | (R,R)-19a | 36 | 86.5:13.5 (73) | 47 |
| 2.1 i-PrLi | (R,R)-19a | 56 | 86.0:14.0 (72) | 20 |
| 1.1 i-PrLi | (R,R)-19a | 0[10] | n.d. | n.d. |
| 2.1 i-PrLi | (R,R)-19a | 0[10] | n.d. | n.d. |
| 2.1 i-PrLi | (R,R)-19a | 71[11] | 85.5:14.5 (71) | 19 |
| 1.1 t-BuLi | (R,R)-19a | 7 | 54.5:45.5 (9) | 79 |
| 2.1 t-BuLi | (R,R)-19a | 10 | 53.5:46.5 (7) | 79 |
| 1.1 cyclo-pentLi | (R,R)-19a | 24 | 79.5:20.5 (59) | 75 |
| 2.1 cyclo-pentLi | (R,R)-19a | 56[12] | 22.0:78.0 (56) | 40 |
| 2.1 i-PrLi | (R,R)-19a | 48[13] | 85.5:14.5 (71) | 35 |
| 2.1 n-BuLi | (S,S)-19c | 69 | 22.0:78.0 (56) | 18 |
| 2.1 i-PrLi | (S,S)-19c | 44 | 11.0:89.0 (78) | 37 |
| 2.1 i-PrLi | (S,S)-19c | 55[14] | 10.5:89.5 (79) | 26 |
| 2.1 i-PrLi | (R,R)-19b | 43 | 87.0:13.0 (74) | 24 |
| 2.1 s-BuLi | (R,R)-19b | 30 | 85.5:14.5 (71) | 52 |
| 2.1 cyclo-pentLi | (R,R)-19b | 48 | 78.0:22.0 (56) | 28 |

| | | | | | |
|---|---|---|---|---|---|
| 2.1 i-PrLi | (R,R)-19b | 60[15] | 89.5:10.5 (79) | 4 | |
| 2.1 i-PrLi | (R,R)-19b | 45[16] | 90.5:9.5 (81) | 10 | |
| 2.1 i-PrLi | (R,R)-19b | 47[17] | 90.5:9.5 (81) | 10 | |
| 2.1 i-PrLi | (R,R)-19b | 42[18] | 90.0:10.0 (80) | 42 | |
| 2.1 i-PrLi | (R,R)-19b | 56[19] | 90.0:10.0 (80) | 28 | |
| 2.1 i-PrLi | (R,R)-19b | 60[120] | 50.5:49.5 (1) | 23 | |
| 2.1 i-PrLi | (S,S)-19c | 55 | 10.5:89.5 (79) | 26 | |
| 2.1 i-PrLi | (R,R)-19a | 48 | 85.5:14.5 (71) | 35 | |

(1) Warmed from −78 to −15° C. during lithiation.

(2) Carried out at −78° C. for duration of lithiation.

(3) Desired product contaminated with ligand-NMR yield of 63%.

(4) Warmed from −78 to −60° C. during lithiation. Desired product 12d contaminated with ligand.

(5) Allowed liquid nitrogen cold bath to warm from −78 to −40° C. over 35 min during lithiation. Desired product 12d contaminated with ligand.

(6) 2.1 equiv (R,R)-19a used [(R,R)-19a:n-BuLi = 3:2]. Desired product 12d contaminated with ligand.

(7) 1.5 equiv (R,R)-19a used ((R,R)-19a:n-BuLi = 3:2). Desired product contaminated with ligand.

(8) 1:1:2 RLi:(R,R)-19a:LiCl used.

(9) Desired product contaminated with ligand; NMR yield of 35% for 12d.

(10) Reaction carried out in i-Pr$_2$O instead of t-BuOMe.

(11) 2.1 equiv (R,R)-19a used ((R,R)-19a:RLi = 3:2).

(12) Desired product contaminated with ligand; NMR yield of 24% for 12d.

(13) Lithiation carried out in Et$_2$O.

(14) Lithiation carried out in Et$_2$O.

(15) Lithiation carried out in 1:1 t-BuOMe:Et$_2$O as solvent.

(16) Lithiation carried out in 1:1 t-BuOMe:PhMe; competetive benzylic deprotonation of toluene suspected.

(17) Lithiation carried out in 1:1 t-BuOMe:cumene as solvent.

(18) Lithiation carried out at −60° C.; still cooled to −78° C. for DMF quench.

(19) Lithiation carried out in Et$_2$O with (R,R)-19b:i-PrLi = 3:2.

(20) Lithiation carried out in THF.

TABLE 3

Lithiation of 11 using Ligand (R,R)-19b or (S,S)-19c, plus 2-dimethylaminoethanol or diisopropylamine additives and Various Alkyllithium Reagents

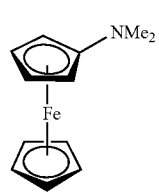

| equiv RLi | additive | ligand | yield, %, 12d | R:S 12d (% ee) | yield, %, 12dd | recovered 11 (%) |
|---|---|---|---|---|---|---|
| 1.65 i-PrLi | DMAE | (R,R)-19b | 43 | 88.0:12.0 (76) | 7 | 48 |
| 3.15 i-PrLi | DMAE | (R,R)-19b | 41 | 89.0:11.0 (78) | 21 | 9 |
| 1.65 i-PrLi | DMAE | (S,S)-19c | 43 | 10.5:89.5 (79) | <5 | 32 |
| 3.15 i-PrLi | DMAE | (S,S)-19c | 61 | 9.0:91.0 (82) | 9 | 19 |
| 1.65 n-BuLi | DMAE | (S,S)-19c | 16 | 23.5:76.5 (53) | 0 | 76 |
| 3.15 n-BuLi | DMAE | (S,S)-19c | 67 | 23.5:76.5 (53) | <5 | 13 |
| 3.15 i-PrLi | DMAE | (S,S)-19c | 45 | 11.0:89.0 (78) | <5 | 45 |
| 3.15 n-BuLi | DIPA | (S,S)-19c | 64 | 22.5:77.5 (55) | 0 | 24 |
| 3.15 i-PrLi | DIPA | (S,S)-19c | 59 | 10.0:90.0 (80) | <5 | 26 |
| 3.15 n-BuLi | DIPA | (R,R)-19b | 52 | 72.5:27.5 (45) | 0 | 33 |
| 3.15 i-PrLi | DIPA | (R,R)-19b | 24 | 89.0:11.0 (78) | 9 | 26 |
| 3.15 i-PrLi | DMAE | (S,S)-19c | 46 | 10.0:90.0 (80) | n.d. | 6 |

TABLE 4

Palladium and Iridium catalyzed Suzuki-Miyaura and Buchwald-Hartwig coupling using 12f as a ligand

| 50a-g | G | X | yield, %, 51a-g | 50a, b, d, e, h | G | X | yield, %, 52a, b, d, e, h |
|---|---|---|---|---|---|---|---|
| a | 4-CF$_3$ | Cl | 94 | a | 4-CF$_3$ | Cl | 77 |
| b | 4-COMe | Cl | 88 | b | 4-COMe | Cl | 74 |
| c | 4-CN | Cl | 92 | d | 2-NO$_2$ | Cl | 43 |
| d | 2-NO$_2$ | Cl | 73 | e | 4-MeO | Br | 67 |
| e | 4-MeO | Cl | 70 | h | H | Br | 82 |
| f | 4-Me | Cl | 56 | | | | |
| g |  | — | 88 | | | | |

TABLE 5

Platinum or Iridium catalyzed intramolecular hydroamination using 12f as a ligand.

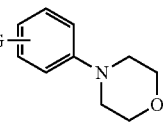

| conditions | yield, % |
|---|---|
| 5 mol % PtCl$_2$, 10 mol % 12f, diethylene glycol, 100° C., 48 h | 27 |
| 2.5 mol % rac-32, dioxane, reflux, 22 h | 64 |

FULL CITATIONS FOR DOCUMENTS REFERRED TO IN THE SPECIFICATION (1) Togni, A. *Angew. Chem., Int. Ed.* 1996, 35, 1475.
(2) Richards, C. J.; Locke, A. J. *Tetrahedron: Asymmetry* 1998, 9, 2377.
(3) Reviews: (a) Arraya's, R. G.; Adrio, J.; Carretero, J. C. *Angew. Chem., Int. Ed.* 2006, 45, 7674. (b) Dai, L.-X.; Tu, T.; You, S.-L.; Deng, W.-P.; Hou, X.-L. *Acc. Chem. Res.* 2003, 36, 659. (c) Colacot, T. J. *Chem. Rev.* 2003, 103, 3101. (d) Miyake, Y.; Nishibayashi, Y.; Uemura, S. *Synlett* 2008, n/a, 1747.
(4) Togni, A.; Deschenaus, R.; Goodby, J. W.; Gonsalves, K. E.; Chen, X. In *Ferrocenes: Homogeneous Catalysis, Organic Synthesis, Materials Science*; Togni, A., Hayashi, T., Eds.; VCH: Weinheim, 1995; pp 433-530.
(5) Marquarding, D.; Klusacek, H.; Gokel, G.; Hoffmann, P.; Ugi, I. *J. Am. Chem. Soc.* 1970, 92, 5389.
(6) (a) Richards, C. J.; Damalidis, T.; Hibbs, D. E.; Hursthouse, M. B. *Synlett* 1995, n/a, 74. (b) Uemura, S.; Nishibayashi, Y. *Synlett* 1995, n/a, 79. (c) Sammakia, T.; Lathman, H. A.; Schad, D. R. *J. Org. Chem.* 1995, 60, 10.
(7) Riant, O.; Samuel, O.; Kagan, H. B. *J. Am. Chem. Soc.* 1993, 115, 5835.
(8) Enders, D.; Peters, R.; Lochtman, R.; Runsink, J. *Synlett* 1997, n/a, 1462.
(9) Tsukazaki, M.; Tinkl, M.; Roglans, A.; Chapell, B. J.; Taylor, N. J.; Snieckus, V. *J. Am. Chem. Soc.* 1996, 118, 685.
(10) For a summary of these and other methods, see: (a) Perseghini, M.; Togni, A. In *Science of Synthesis*; Lautens, M., Ed.; Georg Thieme-Verlag K G: Stuttgart, Germany, 2001; Vol. 1, pp 889-929.
(11) (a) Rebiere, F.; Riant, O.; Ricard, L.; Kagan, H. B. *Angew. Chem., Int. Ed.* 1993, 32, 568. (b) Riant, O.; Argouarch, G.; Guillaneux, D.; Samuel, O.; Kagan, H. B. *J. Org. Chem.* 1998, 63, 3511.
(12) Bolm, C.; Kesselgruber, M.; Muniz, K.; Raabe, G. *Organometallics* 2000, 19, 1648.
(13) He'rault, D.; Aelvoet, K.; Blatch, A. J.; Al-Majid, A.; Smethurst, C. A.; Whiting, A. *J. Org. Chem.* 2007, 72, 71.
(14) Priego, J.; Mancheno, O. G.; Cabrera, S.; Carretero, J. C. *J. Org. Chem.* 2002, 67, 1346. For a related process starting from a ferrocenyl oxazoline, see: Salter, R.; Pickett, T. E.; Richards, C. J. *Tetrahedron:Asymmetry* 1998, 9, 4239.
(15) Bertogg, A.; Camponovo, F.; Togni, A. *Eur. J. Inorg. Chem.* 2005, n/a, 347.
(16) Bertogg, A.; Togni, A. *Organometallics* 2006, 25, 622.
(17) Burchat, A. F.; Chong, J. M.; Nielsen, N. J. Organomet. Chem. 1997, 542, 281.

(18) *Spectrometric Identification of Organic Compounds, Seventh Edition*, p. 200 and p. 240.

(19) Britton, W. E.; Kashyap, R.; El-Hashash, M.; El-Kady, M.; Herberhold, M. *Organometallics* 1986, 5, 1029.

(20) Prepared according to: (a) Sato, M.; Ebine, S. *Synthesis* 1981, n/a, 472.

(21) Fanta, P. E. *Synthesis* 1974, n/a, 9.

(22) Nesmeyanov, A. N.; Sazonova, V. A.; Drozd, V. N. *Chem. Ber.* 1960, 93, 2717.

(23) TMCDA-mediated asymmetric lithiation of (dimethylaminomethyl) ferrocene proceeds in 80% ee: Nishibayashi, Y.; Arikawa, Y.; Ohe, K.; Uemura, S. *J. Org. Chem.* 1996, 61, 1172.

(24) For improved TMCDA derivatives such as 26 in asymmetric organolithium chemistry, see: (a) Stead, D.; O'Brien, P.; Sanderson, A. *Org. Lett.* 2008, 10, 1409. (b) Cabello, N.; Kizirian, J.-C.; Gille, S.; Alexakis, A.; Bernardinelli, G.; Pinchard, L.; Caille, J.-C. *Eur. J. Org. Chem.* 2005, n/a, 483

(25) (a) Stead, D.; O'Brien, P.; Sanderson, A. *Org. Lett.* 2008, 10, 1409. (b) Mealey, M. J.; Luderer, M. R.; Bailey, W. F.; Sommer, M. B. *J. Org. Chem.* 2004, 69, 6042. (c) O'Brien, P. *Chem. Commun.* 2008, 655. (d). (b) Cabello, N.; Kizirian, J.-C.; Gille, S.; Alexakis, A.; Bernardinelli, G.; Pinchard, L.; Caille, J.-C. *Eur. J. Org. Chem.* 2005, 4835.

(26) Black, P. J.; Edwards, M. G.; Williams, J. M. J. *Eur. J. Org. Chem.* 2006, 19, 4367.

(27) Fox, D. J.; Pedersen, D. S.; Warren, S. *Org. Biomol. Chem.* 2006, 4, 3102.

(28) Storer, R. I.; Carrera, D. E.; Ni, Y.; MacMillan, D. W. C. *J. Am. Chem. Soc.* 2006, 128, 84.

(29) Samec, J. S. M.; Backvall, J. E. *Chem. Eur. J.* 2002, 8, 2955.

(30) Buszek, K. R.; Brown, N. *J. Org. Chem.* 2007, 72, 3125.

(31) Taherpour, A. A.; Mansuri, H. R. *Turk. J. Chem.* 2005, 29, 317.

(32) Spectral Database for Organic Compounds (SDBS) (http://riodb01.ibase.aist.go.jp/sdbs/cgi-bin/direct_frame_top.cgi).

(33) Kundig, E. P.; Garcia, A. E.; Lomberget, T.; Bernardinelli, G. *Angew. Chem., Int. Ed.* 2006, 45, 98.

(34) Pearson, M. S.; Jensky, B. J.; Greer, F. X.; Hagstrom, J. P.; Wells, N. M.; *J. Org. Chem.* 1978, 43, 4617.

(35) He, J.; Zheng, J.; Liu, J.; She, X.; Pan, X. *Org. Lett.* 2006, 8, 4637.

(36) Hareau, G. P. J.; Koiwa, M.; Hikichi, S.; Sato, F. *J. Am. Chem. Soc.* 1999, 121, 3640.

The invention claimed is:

1. A method for preparing an ortho-substituted aminoferrocene comprising:
   (i) reacting an aminoferrocene with a Lewis acid and a lithiating reagent in the presence of an electrophile under suitable conditions to produce the ortho-substituted aminoferrocene; or
   (ii) reacting an aminoferrocene with a Lewis acid and a lithiating reagent under suitable conditions to form a lithiated aminoferrocene and subsequently reacting the lithiated aminoferrocene with an electrophile under suitable conditions to produce the ortho-substituted aminoferrocene.

2. The method according to claim 1, wherein the aminoferrocene is a compound of the formula (I):

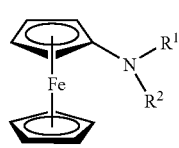

(I)

$R^1$ and $R^2$ are simultaneously or independently selected from $C_{1-10}$alkyl and $C_{3-10}$cycloalkenyl, the latter 2 groups being optionally substituted, or $R^1$ and $R^2$ are linked together to form an optionally substituted monocyclic or bicyclic, saturated ring having 4 or more atoms, including the nitrogen atom to which said groups are bonded;

the cyclopentadienyl ring of the ferrocene that does not contain the amino group is optionally substituted; and
the optional substituents are selected from one or more of fluoro, chloro, $C_{1-6}$alkyl and fluorosubstituted $C_{1-6}$alkyl.

3. The method according to claim 2 wherein $R^1$ and $R^2$ are simultaneously or independently $C_{1-6}$alkyl.

4. The method according to claim 3, wherein $R^1$ and $R^2$ are methyl.

5. The method according to claim 2, wherein $R^1$ and $R^2$ are linked together to form an optionally substituted 5-membered ring, including the nitrogen atom to which $R^1$ and $R^2$ are bonded.

6. The method according to claim 5, wherein $R^1$ and $R^2$ are linked together along with the nitrogen atom to which they are bonded to form a pyrrolidinyl group.

7. The method according to claim 1, wherein the cyclopentadienyl ring of the ferrocene that does not contain the amino group is unsubstituted.

8. The method according to claim 1, wherein the Lewis acid is selected from $BX_3$ and $AlX_3$, wherein X is halo.

9. The method according to claim 8, wherein the Lewis acid is $BF_3$ or $BCl_3$.

10. The method according to claim 9, wherein the Lewis acid is $BF_3$.

11. The method according to claim 1, wherein the lithiating reagent is an alkyl lithiating reagent.

12. The method according to claim 11, the alkyl lithiating reagent is n-butyl lithium, s-butyl lithium, cyclo-pentyl lithium, t-butyl lithium or iso-propyl lithium.

13. The method according to claim 1, wherein the electrophile is a carbon electrophile.

14. The method according to claim 13, wherein the carbon electrophile is a ketone, an isocyanate or an amide.

15. The method according to claim 1, wherein the electrophile is a heteroatom electrophile.

16. The method according to claim 15, wherein the heteroatom electrophile is a silane, a borate, a phosphine, a sulfide, a stannane or a alkyl halide.

17. The method according to any claim 16, wherein the phosphine is a compound of the formula (H):

$R^3R^4$—P-LG  (II)

$R^3$ and $R^4$ are simultaneously or independently selected from $C_{1-20}$alkyl, $C_{3-20}$cycloalkyl, $C_{6-14}$aryl and heteroaryl, the latter three groups being optionally substituted, or $R^3$ and $R^4$ are linked together to form an optionally substituted monocyclic or polycyclic, saturated, unsaturated and/or aromatic ring system having 4 or more atoms, including the phosphorous atom to which said groups are bonded, and in which one or more carbon atoms in said monocyclic or polycyclic ring system is optionally replaced with a heteromoiety selected from O, N, NH and N—$C_{1-6}$alkyl;

LG is any suitable leaving group; and the optional substituents are selected from one or more of halo, $C_{1-6}$alkyl, fluoro-substituted $C_{1-6}$alkyl, $C_{3-6}$cycloalkyl and $C_{6-14}$aryl.

18. The method according to claim 17, wherein $R^3$ and $R^4$ are simultaneously or independently selected from phenyl and $C_{1-6}$alkyl.

19. The method according to claim 17, wherein LG is halo, triflate, mesylate or tosylate.

20. The method according to claim 1, wherein further comprising the addition of a chiral ligand.

21. The method according to claim 20, wherein the chiral ligand is a chiral diamine.

22. The method according to claim 21, wherein the chiral diamine is (–)-sparteine, (S,S)—N,N,N',N'-tetramethylcyclohexane-1,2-diamine,

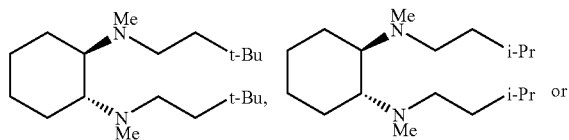

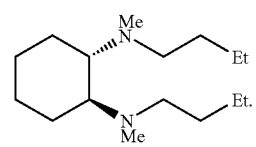

23. The method according to claim 1, wherein the method is repeated to form a tri-substituted aminoferrocene.

24. A method of performing a metal-catalyzed synthetic organic reaction comprising contacting suitable starting materials for the synthetic organic reaction with a metal catalyst comprising an ortho-substituted aminoferrocene obtained using the method according to claim 1 and reacting the starting materials and catalyst under suitable conditions to form the desired product.

25. The method according to claim 24, wherein the metal catalyzed synthetic organic reactions are selected from hydrogenation, transfer hydrogenation, hydroformylation, hydrosilylation, hydroboration, hydroamination, hydrovinylation, hydroarylation, hydration, oxidation, epoxidation, reduction, C—C and C—X bond formation, functional group interconversion, kinetic resolution, dynamic kinetic resolution, cycloaddition, Diels-Alder, retro-Diels-Alder, sigmatropic rearrangement, electrocyclic reactions, ring-opening and/or ring-closing olefin metathesis, carbonylation and aziridination.

26. The method according to claim 25, wherein the C—C and C—X bond formation reaction is selected from Heck, Suzuki-Miyaura, Negishi, Buchwald-Hartwig Amination, α-Ketone Arylation, N-Aryl Amination, Murahashi, Kumada, Negishi and Stille reactions.

27. A compound of the formula (A):

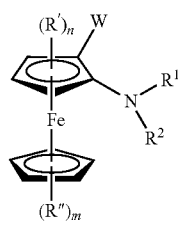

(A)

wherein $R^1$ and $R^2$ are simultaneously or independently selected from $C_{1-10}$alkyl and $C_{3-10}$cycloalkenyl, the latter 2 groups being optionally substituted, or $R^1$ and $R^2$ are linked together to form an optionally substituted monocyclic or bicyclic, saturated ring having 4 or more atoms, including the nitrogen atom to which said groups are bonded;

wherein each R' and R" is independently or simultaneously selected from H, fluoro, chloro, $(C_1-C_6)$-alkyl or fluoro-substituted-$(C_1-C_6)$-alkyl;

n is 1, 2 or 3;

m is 1, 2, 3, 4 or 5;

W is $PR^3R^4$, $P(Y)R^3R^4$, $SiR^5R^6R^7$, $SnR^5R^6R^7$, halo, S—$R^8$, borate esters, $CH_2$heteroaryl, $CH_2OR^9$, $C_{6-10}$aryl, $C_{6-10}$aryl substituted with one to three halo, $C_{1-10}$alkyl, $OR^3$ and/or $NR^5R^6$, C(O)H, C(OH)$R^5R^6$, $OR^9$, C(O)$NR^9R^{10}$ or $CH_2NR^9R^{10}$;

$R^3$ and $R^4$ are simultaneously or independently selected from $C_{1-20}$alkyl, $C_{3-20}$ cycloalkyl, $C_{6-14}$aryl and heteroaryl, the latter three groups being optionally substituted, or $R^3$ and $R^4$ are linked together to form an optionally substituted monocyclic or polycyclic, saturated, unsaturated and/or aromatic ring system having 4 or more atoms, including the phosphorous atom to which said groups are bonded, and in which one or more carbon atoms in said monocyclic or polycyclic ring system is optionally replaced with a heteromoiety selected from O, N, NH and N—$C_{1-6}$alkyl; $R^5$, $R^6$, $R^7$ and $R^8$ are simultaneously or independently selected from $C_{1-10}$alkyl, $C_{2-10}$alkenyl, $C_{3-10}$cycloalkyl and $C_{6-10}$aryl, each being optionally substituted with one to four substituents independently selected from halo, $C_{1-6}$alkyl, fluoro-substituted $C_{1-6}$alkyl, $C_{3-6}$cycloalkyl and phenyl;

$R^9$ and $R^{10}$ are simultaneously or independently selected from H, C(O)$R^8$, $C_{1-10}$alkyl, $C_{2-10}$alkenyl, $C_{3-10}$cycloalkyl and $C_{6-10}$aryl, each being optionally substituted with one to four substituents independently selected from halo, $C_{1-6}$alkyl, fluoro-substituted $C_{1-6}$alkyl, $C_{3-6}$cycloalkyl and phenyl;

Y is S or O; and heteroaryl is a 5- or 6-membered ring containing 1 to 5 heteromoieties selected from S, O, N, NH and N—$C_{1-6}$alkyl;

or any stereoisomer and/or enantiomer thereof, with the proviso that $R^9$ and $R^{10}$ are not simulataneously $C_{1-10}$alkyl.

28. The compound of claim 27, wherein $R^3$ and $R^4$ are simultaneously or independently selected from phenyl, $C_{1-6}$alkyl and $C_{3-6}$cycloalkyl.

29. The compound of claim 28, wherein $R^3$ and $R^4$ are simultaneously or independently selected from phenyl, methyl, ethyl, n-propyl, iso-propyl, sec-butyl, tert-butyl, n-butyl and cyclohexyl.

30. The compound of claim 27, wherein $R^5$, $R^6$, $R^7$ and $R^8$ are simultaneously or independently selected from phenyl, $C_{1-6}$alkyl, $C_{2-6}$alkenyl and $C_{3-6}$cycloalkyl.

31. The compound of claim 30, wherein $R^5$, $R^6$, $R^7$ and $R^8$ are selected from phenyl, phenyl, methyl, ethyl, n-propyl, iso-propyl, sec-butyl, tert-butyl, n-butyl and cyclohexyl.

32. The compound of claim 27, wherein halo is iodo.

33. The method of claim 18, $R^3$ and $R^4$ are simultaneously or independently selected from phenyl, methyl, ethyl, n-propyl, iso-propyl, sec-butyl, tert-butyl and n-butyl.

* * * * *

UNITED STATES PATENT AND TRADEMARK OFFICE
CERTIFICATE OF CORRECTION

PATENT NO. : 7,982,064 B2  Page 1 of 1
APPLICATION NO. : 12/624916
DATED : July 19, 2011
INVENTOR(S) : Costa Metallinos It is certified that error appears in the above-identified patent and that said Letters Patent is hereby corrected as shown below:

In the claims:
Column 60, line 57, Claim 17: "(H)" should read --(II)--.

Signed and Sealed this
Twenty-fifth Day of October, 2011

David J. Kappos
*Director of the United States Patent and Trademark Office*